United States Patent
Selby

(10) Patent No.: US 6,172,005 B1
(45) Date of Patent: Jan. 9, 2001

(54) HETEROARYL AZOLE HERBICIDES

(75) Inventor: Thomas P. Selby, Wilmington, DE (US)

(73) Assignee: E. I. du Pont de Nemours and Company, Wilmington, DE (US)

(*) Notice: Under 35 U.S.C. 154(b), the term of this patent shall be extended for 0 days.

(21) Appl. No.: 09/380,425

(22) PCT Filed: Mar. 9, 1998

(86) PCT No.: PCT/US98/04600
§ 371 Date: Sep. 1, 1999
§ 102(e) Date: Sep. 1, 1999

(87) PCT Pub. No.: WO98/40379
PCT Pub. Date: Sep. 17, 1998

Related U.S. Application Data

(60) Provisional application No. 60/039,544, filed on Mar. 11, 1997.

(51) Int. Cl.[7] ............... A01N 43/54; C07D 239/24; C07D 401/01

(52) U.S. Cl. ............... 504/239; 504/242; 504/243; 504/250; 504/252; 504/253; 544/320; 544/321; 544/323; 544/324; 546/256; 546/268.1; 546/268.4; 546/272.4; 546/274.1; 546/275.4; 546/276.1; 546/276.4; 546/278.4; 546/278.7

(58) Field of Search ............... 504/239, 242, 504/243, 250, 253; 514/236, 273, 340, 341, 343; 544/320, 321, 323, 324; 546/256, 268.1, 268.4, 272.4, 274.1, 275.4, 276.1, 276.4, 278.4, 278.7

(56) References Cited

U.S. PATENT DOCUMENTS

| 4,405,743 | * 9/1983 | Nishimura et al. ............... 424/321 |
| 5,750,470 | 4/1998 | Morimoto et al. ............... 504/253 |

FOREIGN PATENT DOCUMENTS

| 29 35 578 A1 | 4/1981 | (DE) . |
| 0 216 360 A2 | 9/1986 | (EP) . |
| 0 572 093 A1 | 5/1993 | (EP) . |
| 0 723 960 A1 | 1/1996 | (EP) . |
| WO 96/06096 | 2/1996 | (WO) . |
| WO 98/04550 | 2/1998 | (WO) . |
| WO 98/37079 | * 8/1998 | (WO) . |

* cited by examiner

*Primary Examiner*—Mukund J. Shah
*Assistant Examiner*—Ben Schroeder

(57) ABSTRACT

Compounds of Formula I, and their N-oxides and agriculturally suitable salts, are disclosed which are useful for controlling undesired vegetation

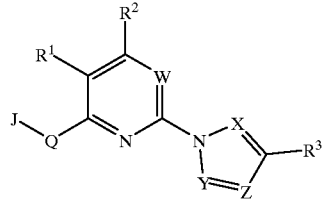

I wherein J is

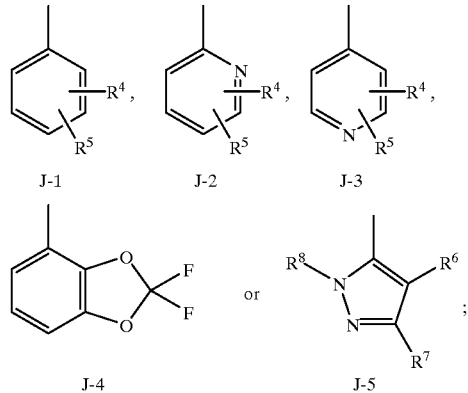

and Q, W, X, Y, Z, and $R^1$ through $R^8$ are as defined in the disclosure.

Also disclosed are compositions containing the compounds of Formula I and a method for controlling undesired vegetation which involves contacting the vegetation or its environment with an effective amount of a compound of Formula I.

9 Claims, No Drawings

HETEROARYL AZOLE HERBICIDES

CROSS REFERENCE TO RELATED APPLICATIONS

This application is a national stage entry under 35 U.S.C. 371 of PCT/US98/04600, filed Mar. 9, 1998 which claims the benefit of U.S. Provisional Application Ser. No. 60/039,544 filed Mar. 11, 1997.

BACKGROUND OF THE INVENTION

This invention relates to certain heteroaryl azoles, their N-oxides, agriculturally suitable salts, compositions thereof, and methods of their use for controlling undesirable vegetation.

The control of undesired vegetation is extremely important in achieving high crop efficiency. Achievement of selective control of the growth of weeds especially in such useful crops as rice, soybean, sugar beet, corn (maize), potato, wheat, barley, tomato and plantation crops, among others, is very desirable. Unchecked weed growth in such useful crops can cause significant reduction in productivity and thereby result in increased costs to the consumer. The control of undesired vegetation in noncrop areas is also important. Many products are commercially available for these purposes, but the need continues for new compounds which are more effective, less costly, less toxic, environmentally safer or have different modes of action.

WO 96/06096 discloses herbicidal substituted pyridines of the formula

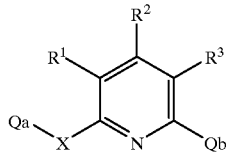

wherein, inter alia, $R^1$, $R^2$, and $R^3$ are each independently hydrogen, alkyl, alkoxy, cyano, nitro or halogen;

Qa is optionally substituted phenyl, pyrazolyl or pyridyl;

Qb is azolyl;

X is O, S or $NR^4$; and $R^4$ is H or alkyl.

The heteroaryl azoles of the present invention are not disclosed in this publication.

SUMMARY OF THE INVENTION

This invention is directed to compounds of Formula I including all geometric and stereoisomers, N-oxides, and agriculturally suitable salts thereof, as well as agricultural compositions containing them and a method of their use for controlling undesirable vegetation:

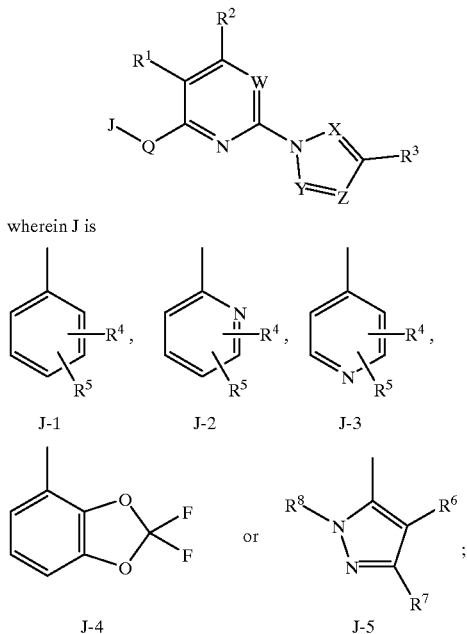

wherein J is

W is N or $CR^9$;

X, Y and Z are independently N, CH or $CR^9$, provided that only one of X, Y and Z is $CR^9$;

Q is O, $S(O)_n$ or $NR^{10}$;

$R^1$ and $R^2$ are independently H, halogen, cyano, $C_1$–$C_4$ alkoxy, $C_1$–$C_4$ haloalkoxy, $C_2$–$C_4$ alkoxyalkyl, $C_3$–$C_5$ dialkoxyalkyl, $C_1$–$C_4$ alkyl, $C_1$–$C_4$ haloalkyl, $C_2$–$C_4$ alkoxyalkyl, $C_3$–$C_4$ alkenyl, $C_3$–$C_4$ alkynyl, $C_3$–$C_4$ alkenyloxy, $C_3$–$C_4$ alkynyloxy, $S(O)_nR^8$, $C_2$–$C_4$ alkylthioalkyl, $C_2$–$C_4$ alkylsulfonylalkyl, $C_1$–$C_4$ alkylamino or $C_2$–$C_4$ dialkylamino;

$R^3$ is H, halogen, cyano, $C_1$–$C_4$ alkoxy, $C_1$–$C_4$ haloalkoxy, $C_1$–$C_4$ haloalkyl, $C_2$–$C_4$ alkoxyalkyl, $C_3$–$C_4$ alkenyl, $C_3$–$C_4$ alkynyl, $C_3$–$C_4$ alkenyloxy, $C_3$–$C_4$ alkynyloxy or $S(O)_nR^8$;

$R^4$ is halogen, cyano, $SF_5$, $C_1$–$C_4$ haloalkyl, $C_1$–$C_4$ alkoxy, $C_1$–$C_4$ haloalkoxy or $S(O)_nR^8$;

$R^5$ is H, halogen, cyano, $SF_5$, $C_1$–$C_4$ haloalkyl, $C_1$–$C_4$ alkoxy, $C_1$–$C_4$ haloalkoxy or $S(O)_nR^8$;

$R^6$ is H, halogen, cyano, $SF_5$, $C_1$–$C_4$ haloalkyl, $C_1$–$C_4$ alkoxy, $C_1$–$C_4$ haloalkoxy or $S(O)_nR^8$;

$R^7$ is halogen, cyano, $SF_5$, $C_1$–$C_4$ haloalkyl, $C_1$–$C_4$ alkoxy, $C_1$–$C_4$ haloalkoxy or $S(O)_nR^8$;

each $R^8$ is independently $C_1$–$C_4$ alkyl or $C_1$–$C_4$ haloalkyl;

each $R^9$ is independently halogen, cyano, $C_1$–$C_4$ alkoxy, $C_1$–$C_4$ haloalkoxy, $C_1$–$C_4$ alkyl, $C_1$–$C_4$ haloalkyl, $C_2$–$C_4$ alkoxyalkyl, $C_3$–$C_4$ alkenyl, $C_3$–$C_4$ alkynyl, $C_3$–$C_4$ alkenyloxy, $C_3$–$C_4$ alkynyloxy or $S(O)_nR^8$;

$R^{10}$ is H, $C_1$–$C_4$ alkyl or $C_1$–$C_4$ haloalkyl; and each n is independently 0, 1 or 2.

In the above recitations, the term "alkyl", used either alone or in compound words such as "alkylthio" or "haloalkyl" includes straight-chain or branched alkyl, such as, methyl, ethyl, n-propyl, i-propyl, or the different butyl, pentyl or hexyl isomers. The term "1-2 alkyl" indicates that one or two of the available positions for that substituent may be alkyl which are independently selected. "Alkenyl" includes straight-chain or branched alkenes such as ethenyl, 1-propenyl, 2-propenyl, and the different butenyl, pentenyl and hexenyl isomers. "Alkenyl" also includes polyenes such as 1,2-propadienyl and 2,4-hexadienyl. "Alkynyl" includes straight-chain or branched alkynes such as ethynyl, 1-propynyl, 2-propynyl and the different butynyl, pentynyl and hexynyl isomers. "Alkynyl" can also include moieties comprised of multiple triple bonds such as 2,5-hexadiynyl. "Alkoxy" includes, for example, methoxy, ethoxy, n-propyloxy, isopropyloxy and the different butoxy, pentoxy and hexyloxy isomers. "Alkoxyalkyl" denotes alkoxy substitution on alkyl. Examples of "alkoxyalkyl" include $CH_3OCH_2$, $CH_3OCH_2CH_2$, $CH_3CH_2OCH_2$, $CH_3CH_2CH_2CH_2OCH_2$ and $CH_3CH_2OCH_2CH_2$. "Alkenyloxy" includes straight-chain or branched alkenyloxy moieties. Examples of "alkenyloxy" include $H_2C=CHCH_2O$, $(CH_3)_2C=CHCH_2O$, $(CH_3)CH=CHCH_2O$, $(CH_3)CH=C(CH_3)CH_2O$ and $CH_2=CHCH_2CH_2O$. "Alkynyloxy" includes straight-chain or branched alkynyloxy moieties. Examples of "alkynyloxy" include $HC\equiv CCH_2O$, $CH_3C\equiv CCH_2O$ and $CH_3C\equiv CCH_2CH_2O$. "Alkylthio" includes branched or straight-chain alkylthio moieties such as methylthio, ethylthio, and the different propylthio, butylthio, pentylthio and hexylthio isomers. "Alkylthioalkyl" denotes alkylthio substitution on alkyl. Examples of "alkylthioalkyl" include $CH_3SCH_2$, $CH_3SCH_2CH_2$, $CH_3CH_2SCH_2$, $-CH_3CH_2CH_2CH_2SCH_2$ and $CH_3CH_2SCH_2CH_2$. "Alkylthioalkoxy" denotes alkylthio substitution on alkoxy. "Alkylsulfinyl" includes both enantiomers of an alkylsulfinyl group. Examples of "alkylsulfinyl" include $CH_3S(O)$, $CH_3CH_2S(O)$, $CH_3CH_2CH_2S(O)$, $(CH_3)_2CHS(O)$ and the different butylsulfinyl, pentylsulfinyl and hexylsulfinyl isomers. Examples of "alkylsulfonyl" include $CH_3S(O)_2$, $CH_3CH_2S(O)_2$, $CH_3CH_2CH_2S(O)_2$, $(CH_3)_2CHS(O)_2$ and the different butylsulfonyl, pentylsulfonyl and hexylsulfonyl isomers. "Cyanoalkyl" denotes an alkyl group substituted with one cyano group. Examples of "cyanoalkyl" include $NCCH_2$, $NCCH_2CH_2$ and $CH_3CH(CN)CH_2$. "Alkylamino", "dialkylamino", "alkenylthio", "alkenylsulfinyl", "alkenylsulfonyl", "alkynylthio", "alkynylsulfinyl", "alkynylsulfonyl", and the like, are defined analogously to the above examples.

One skilled in the art will appreciate that not all nitrogen containing heterocycles can form N-oxides since the nitrogen requires an available lone pair for oxidation to the oxide; one skilled in the art will recognize those nitrogen containing heterocycles which can form N-oxides. One skilled in the art will also recognize that tertiary amines can form N-oxides. Synthetic methods for the preparation of N-oxides of heterocycles and tertiary amines are very well known by one skilled in the art including the oxidation of heterocycles and tertiary amines with peroxy acids such as peracetic and m-chloroperbenzoic acid (MCPBA), hydrogen peroxide, alkyl hydroperoxides such as t-butyl hydroperoxide, sodium perborate, and dioxiranes such as dimethyldioxirane. These methods for the preparation of N-oxides have been extensively described and reviewed in the literature, see for example: T. L. Gilchrist in *Comprehensive Organic Synthesis*, vol. 7, pp 748–750, S. V. Ley, Ed., Pergamon Press; M. Tisler and B. Stanovnik in *Comprehensive Heterocyclic Chemistry*, vol. 3, pp 18–20, A. J. Boulton and A. McKillop, Eds., Pergamon Press; M. R. Grimmett and B. R. T. Keene in *Advances in Heterocyclic Chemistry*, vol. 43, pp 149–161, A. R. Katritzky, Ed., Academic Press; M. Tisler and B. Stanovnik in *Advances in Heterocyclic Chemistry*, vol. 9, pp 285–291, A. R. Katritzky and A. J. Boulton, Eds., Academic Press; and G. W. H. Cheeseman and E. S. G. Werstiuk in *Advances in Heterocyclic Chemistry*, vol. 22, pp 390–392, A. R. Katritzky and A. J. Boulton, Eds., Academic Press.

The term "halogen", either alone or in compound words such as "haloalkyl", includes fluorine, chlorine, bromine or iodine. The term "1-2 halogen" indicates that one or two of the available positions for that substituent may be halogen which are independently selected. Further, when used in compound words such as "haloalkyl", said alkyl may be partially or fully substituted with halogen atoms which may be the same or different. Examples of "haloalkyl" include $F_3C$, $ClCH_2$, $CF_3CH_2$ and $CF_3CCl_2$. The terms "haloalkenyl", "haloalkynyl", "haloalkoxy", "haloalkylthio", and the like, are defined analogously to the term "haloalkyl". Examples of "haloalkenyl" include $(Cl)_2C=CHCH_2$ and $CF_3CH_2CH=CHCH_2$. Examples of "haloalkynyl" include $HC\equiv CCHCl$, $CF_3C\equiv C$, $CCl_3C\equiv C$ and $FCH_2C\equiv CCH_2$. Examples of "haloalkoxy" include $CF_3O$, $CCl_3CH_2O$, $HCF_2CH_2CH_2O$ and $CF_3CH_2O$. Examples of "haloalkylthio" include $CCl_3S$, $CF_3S$, $CCl_3CH_2S$ and $ClCH_2CH_2CH_2S$. Examples of "haloalkylsulfinyl" include $CF_3S(O)$, $CCl_3S(O)$, $CF_3CH_2S(O)$ and $CF_3CF_2S(O)$. Examples of "haloalkylsulfonyl" include $CF_3S(O)_2$, $CCl_3S(O)_2$, $CF_3CH_2S(O)_2$ and $CF_3CF_2S(O)_2$. Examples of "haloalkoxyalkoxy" include $CF_3OCH_2O$, $ClCH_2CH_2OCH_2CH_2O$, $Cl_3CCH_2OCH_2O$ as well as branched alkyl derivatives.

The total number of carbon atoms in a substituent group is indicated by the "$C_i$–$C_j$" prefix where i and j are numbers from 1 to 5. For example, $C_1$–$C_3$ alkylsulfonyl designates methylsulfonyl through propylsulfonyl; $C_2$ alkoxyalkyl designates $CH_3OCH_2$; $C_3$ alkoxyalkyl designates, for example, $CH_3CH(OCH_3)$, $CH_3OCH_2CH_2$ or $CH_3CH_2OCH_2$; and $C_4$ alkoxyalkyl designates the various isomers of an alkyl group substituted with an alkoxy group containing a total of four carbon atoms, examples including $CH_3CH_2CH_2OCH_2$ and $CH_3CH_2OCH_2CH_2$. Examples of "alkylcarbonyl" include $C(O)CH_3$, $C(O)CH_2CH_2CH_3$ and $C(O)CH(CH_3)_2$. Examples of "alkoxycarbonyl" include $CH_3OC(=O)$, $CH_3CH_2OC(=O)$, $CH_3CH_2CH_2OC(=O)$, $(CH_3)_2CHOC(=O)$ and the different butoxy- or pentoxycarbonyl isomers. In the above recitations, when a compound of Formula I is comprised of one or more heterocyclic rings, all substituents are attached to these rings through any available carbon or nitrogen by replacement of a hydrogen on said carbon or nitrogen.

When a compound is substituted with a substituent bearing a subscript that indicates the number of said substituents can exceed 1, said substituents (when they exceed 1) are independently selected from the group of defined substituents. Further, when the subscript indicates a range, e.g. $(R)_{i-j}$, then the number of substituents may be selected from the integers between i and j inclusive.

When a group contains a substituent which can be hydrogen, for example $R^{10}$, then, when this substituent is taken as hydrogen, it is recognized that this is equivalent to said group being unsubstituted.

The compounds of this invention thus include compounds of Formula I, geometric and stereoisomers thereof, N-oxides thereof, and agriculturally suitable salts thereof. The compound of the invention can exist as one or more stereoisomers. The various stereoisomers include enantiomers, diastereomers, atropisomers and geometric isomers. One skilled in the art will appreciate that one stereoisomer may be more active and/or may exhibit beneficial effects when enriched relative to the other stereoisomer(s) or when separated from the other stereoisomer(s). Additionally, the skilled artisan knows how to separate, enrich, and/or to selectively prepare said stereoisomers. The compounds of the invention may be present as a mixture of stereoisomers, individual stereoisomers, or as an optically active form.

The salts of the compounds of the invention include acid-addition salts with inorganic or organic acids such as hydrobromic, hydrochloric, nitric, phosphoric, sulfuric, acetic, butyric, fumaric, lactic, maleic, malonic, oxalic, propionic, salicylic, tartaric, 4-toluenesulfonic or valeric acids. The salts of the compounds of the invention also include those formed with organic bases (e.g., pyridine, ammonia, or triethylamine) or inorganic bases (e.g., hydrides, hydroxides, or carbonates of sodium, potassium, lithium, calcium, magnesium or barium) when the compound contains an acidic group such as a carboxylic acid or phenol.

Preferred compounds of the invention for reasons of better activity and/or ease of synthesis are:

Preferred 1. Compounds of Formula I above, geometric and stereoisomers thereof, N-oxides thereof, and agriculturally-suitable salts thereof, wherein:

Q is 0;

$R^1$ and $R^2$ are independently H, $C_1$–$C_4$ alkyl or $C_1$–$C_4$ alkoxy; and $R^3$ is halogen, $C_1$–$C_4$ haloalkyl, $C_1$–$C_4$ haloalkoxy or $C_1$–$C_4$ haloalkylthio.

Preferred 2. Compounds of Preferred I wherein:

W is N;

Y is $CR^9$; and $R^5$ is H.

Preferred 3. Compounds of Preferred 2 wherein:

$R^2$ is H; and each $R^4$ is independently halogen, $C_1$–$C_4$ haloalkyl, $C_1$–$C_4$ haloalkoxy or $C_1$–$C_4$ haloalkylthio.

Most preferred are compounds of Formula I above selected from the group:

(a) 5-methyl-4-[3-(trifluoromethyl)phenoxy]-2-[3-(trifluoromethyl)-1H-pyrazol-1-yl]pyrimidine;

(b) 4-[3-(trifluoromethyl)phenoxy]-2-[3-(trifluoromethyl)-1H-pyrazol-1-yl]pyrimidine;

(c) 5-methyl-4-[3-(trifluoromethoxy)phenoxy]-2-[4-(trifluoromethyl)-1H-imidazol-1-yl]pyrimidine;

(d) 5-methyl-2-[3-(Triluoromethyl)-1H-pyrazol-1-yl]4-[[6-(trifluoromethyl)-2-pyridinyl]oxy]pyrimidine;

(e) 5-methyl-4-[3-(trifluoromethyl)phenoxy]-2-[3-(trifluoromethyl)-1H-1,2,4-triazol-1-yl]pyrimidine;

(f) 5-methyl-2-[4-(trifluoromethyl)-1H-imidazol-1-yl]-4-[3-(trifluoromethyl)phenoxy]pyrimidine;

(g) 5-ethyl4-[3-(trifluoromethyl)phenoxy]-2-[3-(trifluoromethyl)-1H-pyrazol-1-yl]pyrimidine;

(h) 5-ethyl4-[3-(trifluoromethoxy)phenoxy]-2-[3-(trifluoromethyl)-1H-pyrazol-1-yl]pyrimidine;

(i) 5-ethyl-2-[4-(trifluoromethyl)-1H-imidazol-1-yl]4-[3-(trifluoromethyl)phenoxy)pyrimidine; and (j) 5-ethyl-4-[3-(trifluoromethoxy)phenoxy]-2- [4-(trifluoromethyl)-1H-imidazol-1-yl]pyrimidine.

This invention also relates to herbicidal compositions comprising herbicidally effective amounts of the compounds of the invention and at least one of a surfactant, a solid diluent or a liquid diluent. The preferred compositions of the present invention are those which comprise the above preferred compounds.

This invention also relates to a method for controlling undesired vegetation comprising applying to the locus of the vegetation herbicidally effective amounts of the compounds of the invention (e.g., as a composition described herein). The preferred methods of use are those involving the above preferred compounds.

DETAILS OF THE INVENTION

The compounds of Formula I can be prepared by one or more of the following methods and variations as described in Schemes 1–5. The definitions of J, Q, W, X, Y, Z, $R^1$, $R^2$ and $R^3$ in the compounds of Formulae 1–4 below are as defined above in the Summary of the Invention.

Scheme 1 illustrates the preparation of compounds of Formula I wherein compounds of Formula 1 are allowed to react with compounds of Formula 2 and a suitable base such as potassium carbonate, potassium hydroxide or sodium hydride in a solvent such as NN-dimethylformamide, acetonitrile, or tetrahydrofuran at temperatures ranging from 0° C. to 130° C.

Scheme 1

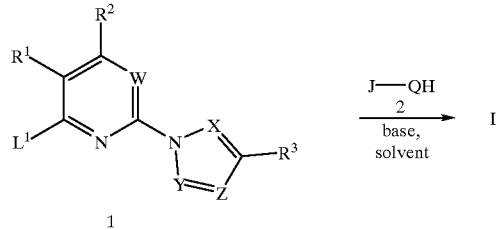

$L^1$ is a leaving group such as halogen or methylsulfonyl

Heterocycles of Formula 1 where $L^1$ is halogen can be prepared by reacting pyridines or pyrimidines of Formula 3 with azoles of Formula 4 in the presence of a base such as potassium carbonate, potassium hydroxide or sodium hydride in a solvent such as N,N-dimethylformamide, acetonitrile, or tetrahydrofuran at temperatures ranging from 0° C. to 130° C. (Scheme 2). This condensation generally gives rise to mixtures of products of Formula 1 and 1a which can be separated by silica gel chromatography.

Scheme 2

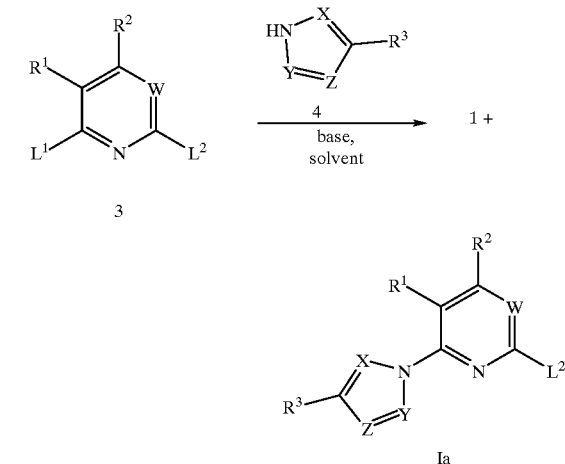

$L^1$ and $L^2$ are halogen

As shown in Scheme 3, heterocycles of Formula 1 where $L^1$ is methylsulfonyl can be prepared from compounds of Formula 5 by oxidation with m-chloroperoxybenzoic acid in a halogenated solvent such as dichloromethane or with Oxone® (potassium peroxymonosulfate) in an alcohol solvent such as methanol at temperatures ranging from 0° C. to 60° C. This type of oxidation reaction is well known in the art; for example, see March, J. *Advanced Organic Chemistry;* John Wiley: New York, 1992; 4$^{th}$ edition, pp 1201–1203.

Scheme 3

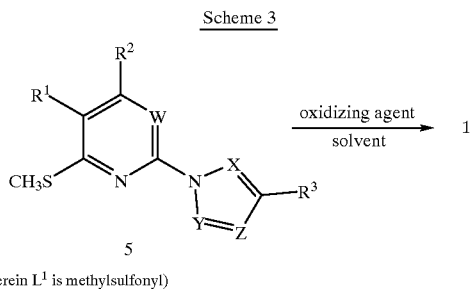

(wherein L$^1$ is methylsulfonyl)

Scheme 4 illustrates the preparation of compounds of Formula 5 wherein compounds of Formula 6 (where L$^2$ is halogen) are allowed to react with compounds of Formula 4 and a suitable base such as potassium carbonate, potassium hydroxide or sodium hydride in a solvent such as N,N-dimethylformamide or acetonitrile at temperatures ranging from 0° C. to 130° C.

Scheme 4

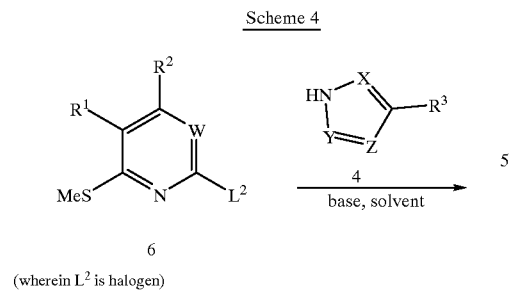

(wherein L$^2$ is halogen)

Compounds of Formula 6 can be readily prepared by reaction of compounds of Formula 3 with the sodium or potassium salt of methyl mercaptan in a solvent such as tetrahydrofuran or dioxane at temperatures ranging from 0° C. to 80° C.

Scheme 5

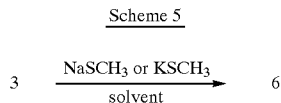

Dihaloheterocycles of Formula 3 can be obtained commercially or are readily prepared by known methods in the art; for example, see *Advances in Heterocyclic Chemisty;* Katritzky, A. R., Ed.; Academic Press: New York, 1993; volume 58, pp 301–305; *Heterocyclic Compounds;* Elderfield, R. C., Ed.; John Wiley: New York, 1957; volume 6, chapter 7, pp 265–270.

Compounds of Formula 4 can be obtained commercially or can be prepared by methods that are known in the art; for examples, see Elguero, J. et al. *Organic Preparations and Procedures Int.* (1995), 27, pp 33–74; *Comprehensive Heterocyclic Chemistry;* Potts, K., Ed.; Pergamon Press: New York, 1984; volume 5, chapters 4.04–4.13; *Heterocyclic Compounds;* Elderfield, R., Ed.; John Wiley: New York, 1957; volume 5, chapters 2 and 4; and Baldwin, J. et al. *J. Med. Chem.* (1975), 18, pp 895–900; Evans, J. J. et al. U.S. Pat. No. 4,038,405 (1977).

As described for the oxidation above, compounds of Formula I wherein Q is S(O)$_n$ and n is 1 or 2 can be prepared from compounds of Formula I wherein Q is S(O)$_n$ and n is 0 by treatment with an oxidizing reagent such as m-chloroperoxybenzoic acid or Oxone® (potassium peroxymonosulfate).

It is recognized that some reagents and reaction conditions described above for preparing compounds of Formula I may not be compatible with certain functionalities present in the intermediates. In these instances, the incorporation of protection/deprotection sequences or functional group interconversions into the synthesis will aid in obtaining the desired products. The use and choice of the protecting groups will be apparent to one skilled in chemical synthesis (see, for example, Greene, T. W.; Wuts, P. G. M. *Protective Groups in Organic Synthesis,* 2nd ed.; Wiley: New York, 1991). One skilled in the art will recognize that, in some cases, after the introduction of a given reagent as it is depicted in any individual scheme, it may be necessary to perform additional routine synthetic steps not described in detail to complete the synthesis of compounds of Formula I. One skilled in the art will also recognize that it may be necessary to perform a combination of the steps illustrated in the above schemes in an order other than that implied by the particular sequence presented to prepare the compounds of Formula I.

One skilled in the art will also recognize that compounds of Formula I and the intermediates described herein can be subjected to various electrophilic, nucleophilic, radical, organometallic, oxidation, and reduction reactions to add substituents or modify existing substituents.

Without further elaboration, it is believed that one skilled in the art using the preceding description can utilize the present invention to its fullest extent. The following Examples are, therefore, to be construed as merely illustrative, and not limiting of the disclosure in any way whatsoever. Percentages are by weight except for chromatographic solvent mixtures or where otherwise indicated. Parts and percentages for chromatographic solvent mixtures are by volume unless otherwise indicated. $^1$H NMR spectra are reported in ppm downfield from tetramethylsilane; s=singlet, d=doublet, t=triplet, q=quartet, m=multiplet, dd=doublet of doublets, dt=doublet of triplets, br s=broad singlet.

EXAMPLE 1

Step A: Preparation of 2-bromo-6-[3-(trifluoromethyl)-1H-prazol-1-yl]pyridine

A mixture of 2,6-dibromopyridine (3.5 g, 22 mmol), 3-(trifluoromethyl)-1H-pyrazole 2.0 g, 15 mmol) and potassium carbonate (4.0 g, 29 mmol) was heated in 25 mL of N,N-dimethylformamide at 90° C. for 3 h. The reaction mixture was partitioned between ethyl acetate and water. The separated organic layer was washed twice with brine, dried over magnesium sulfate, and evaporated under reduced pressure to give an oily residue which was purified by flash chromatography on silica gel (50:1 to 20:1 hexane/ethyl acetate) to yield 1.2 g of the title compound of Step A as a white solid melting at 55–56° C. $^1$H NMR (CDCl$_3$): δ 6.73 (d, 1H), 7.45 (d, 1H), 7.71 (t, 1H), 7.97 (d, 1H), 8.60 (d, 1H).

Step B: Preparation of 2-[3-(trifluoromethyl)phenoxyl-6-f3-(trifluoromethyl)-1H-pyrazol-1-yl]pyridine A mixture of the title compound of Step A (0.9 g, 3.1 mmol), 3-trifluoromethylphenol (0.7 g, 4.3 mmol) and potassium carbonate (0.9 g, 6.5 mmol) was heated in 15 mL of N,N-dimethylformamide at 110–120° C. for 7 h. The reaction mixture was then partitioned between ethyl acetate and water. The separated organic layer was washed with water and brine, dried over magnesium sulfate, and evaporated under reduced pressure to give an oily residue. Purification by flash chromatography on silica gel (40:1 hexane/ethyl acetate) afforded 1.1 g of the title compound of Step B, a compound of this invention, as a white solid melting at 53–55° C. $^1$H NMR (CDCl$_3$): δ 6.60 (d, 1H), 6.92 (d, 1H), 7.36 (d, 1H), 7.43–7.60 (m, 3H), 7.73 (d, 1H), 7.88 (t, 1H), 8.12 (d, 1H).

EXAMPLE 2

Step A: Preparation of 4-chloro-2-[3-(trifluoromethyl)-1H-pyrazol-1-yl]pyrimidine A mixture of 2,4-dichloropyrimidine (3.0.g, 20 mmol), 3-(trifluoromethyl)-1H-pyrazole (2.5 g, 18 mmol) and potassium carbonate (5.0 g, 36 mmol) was stirred in 25 mL of N,N-dimethylformamide at room temperature overnight. The reaction mixture was partitioned between ethyl acetate and water. The separated organic layer was washed twice with brine, dried over magnesium sulfate, and evaporated under reduced pressure to a crude solid. Flash chromatography on silica gel (50:1 to 25:1 to 110:1 to 3:1 hexane/ethyl acetate) afforded 0.5 g of the title compound of Step A as a solid melting at 123–125° C. and 2.3 g of the isomer 2-chloro-6-[3-(trifluoromethyl)-1H-pyrazol-1-yl]pyrimidine as a solid melting at 111–112° C. $^1$H NMR (CDCl$_3$): δ 6.77 (d, 1H), 7.35 (d, 1H), 8.65 (d, 1H), 8.70 (d, 1H).

Step B: Preparation of 4-[3-(trifluoromethyl)phenoxy]-2-[3-(trifluoromethyl)-1H-pyrazol-1-yl]pyrimidine A mixture of the title compound of Step A (0.5 g, 2 mmol), 3-trifluoromethylphenol (0.4 g, 2.5 mmol) and potassium carbonate (0.5 g, 3.6 mmol) was stirred in 10 mL of N,N-dimethylformamide at room temperature overnight. The reaction mixture was partitioned between ethyl acetate and water. The separated organic layer was washed twice with brine, dried over magnesium sulfate, and evaporated under reduced pressure to give an oily residue. Flash chromatography on silica gel (5:1 to 3:1 hexane/ethyl acetate) afforded 0.3 g of the title compound of Step B, a compound of this invention, as a white solid, melting at 72–73° C. $^1$H NMR (CDCl$_3$): δ 6.65 (d, 1H), 6.91 (d, 1H), 7.40–7.65 (m, 4H), 8.22 (d, 1H), 8.71 (d, 1H).

EXAMPLE 3

Step A: Preparation of 2-chloro-5-methyl-4-methylthio] pyrimidine

To a solution of 2,4-dichloro-5-methylpyrimidine (10.0 g, 61 mmol) stirring in 200 mL of tetrahydrofuiran was added sodium thiomethoxide (5.0 g, 71 mmol) and the mixture stirred at room temperature overnight. The reaction mixture was partitioned between 200 mL of ethyl acetate and 200 mL of water. The separated organic layer was washed twice with water and brine, dried over magnesium sulfate, and evaporated under reduced pressure to give a white solid which was suspended in a minimal amount of hexanes and filtered. Additional solid was filtered from the filtrate several times and all of the crops were combined to give 9.3 g of the title compound of Step A as a solid melting at 75–77° C. $^1$H NMR (CDCl$_3$): δ 8.02 (s, 1H), 2.60 (s, 3H) 2.17 (s, 3H).

Step B: Preparation of 5-methyl-4-methylthio-2-[3-(trifluoromethyl)-1H-pyrazol-1-yl]pyrimidine A mixture of 2-chloro-5-methyl-4-methylthiopyrimidine (2.5 g, 14 mmol), 3-(trifluoromethyl)-1H-pyrazole (2.3 g, 2.5 mmol) and potassium carbonate (4.8 g, 35 mmol) in 25 mL of N,N-dimethylformamide was heated at 70° C. with stirring for 5 hours. The reaction mixture was then partitioned between ethyl acetate and water. The organic layer was separated, washed twice with water and brine and dried over magnesium sulfate. The solvent was removed under reduced pressure to provide a white solid which was suspended in hexane and filtered to provide 2.4 g of the title compound of Step B as a solid melting at 126–127° C. $^1$H NMR (CDCl$_3$): δ 8.63 (d, 1H), 8.24 (s, 1H), 6.73 (d, 1H), 2.68 (s, 3H) 2.25 (s, 3H).

Step C: Preparation of 5-methyl-4-(methylsulfonyl)-2-[3-(trifluoromethyl)-1H-13pyrazol-1-yl]pyrimidine To a solution of 5-methyl-4-methylthio-2-[3-(trifluoromethyl)-1H-pyrazol-1-yl]pyrimidine (2.4 g, 9 mmol) stirred in 40 mL of dichloromethane was added m-chloroperoxybenzoic acid (5 g, 57–86%). A solid gradually precipitated and the white slurry stirred overnight at room temperature. The reaction mixture was filtered and the filtrate evaporated under reduced pressure to give a residue which was dissolved in 130 mL of diethyl ether. After washing twice with aqueous sodium bisulfite, three times with aqueous sodium bicarbonate and brine, the organic layer was dried over magnesium sulfate. The solvent was removed under reduced pressure to give a white solid which was suspended in hexane and filtered to give 2.4 g of the title compound of Step C as a solid melting at 129–131° C. $^1$H NMR (CDCl$_3$): δ 8.87 (s, 1H), 8.57 (d, 1H), 6.79 (d, 1H), 3.49 (s, 3H) 2.73 (s, 3H).

Step D: Preparation of 5-methyl-4-[3-(trifluoromethyl) phenoxy]-2-[3-(trifluoromethyl)-1H-1)pyrazol-1-yl] pyrimidine A mixture of 5-methyl-4-methylsulfonyl-2-[3-(trifluoromethyl)-1H-pyrazol-1-yl]pyrimidine (0.3 g, 1 mmol), 3-trifluoromethylphenol (0.2 mL, 1.3 mmol) and potassium carbonate (0.3 g, 2 mmol) in 10 mL of N,N-dimethylformamide was stirred at room temperature overnight. The reaction mixture was partitioned between ethyl acetate and water. The organic layer was separated and washed with water, saturated aqueous sodium bicarbonate and brine. After drying over magnesium sulfate, the solvent was removed under reduced pressure to give an oily residue. Purification by flash chromatography on silica gel (5:1 followed by 3:1 hexane/ethyl acetate) afforded 150 mg of the title compound of Step D, a compound of this invention, as a white solid melting at 113–115° C. $^1$H NMR (CDCl$_3$): δ 8.53 (s, 1H), 8.07 (d, 1H), 7.65–7.58 (m, 2H), 7.57 (s, 1H), 7.47–7.40 (m, 1H), 6.61 (d, 1H), 2.48 (s, 3H).

By the procedures described herein together with methods known in the art, the following compounds of Tables 1 to 5 can be prepared.

TABLE 1

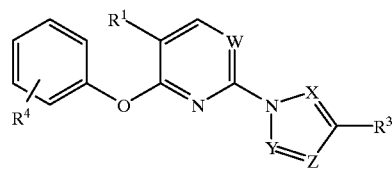

| W | R¹ | R³ | R⁴ | W | R¹ | R³ | R⁴ |
|---|---|---|---|---|---|---|---|
| \multicolumn{8}{c}{wherein X is N and Y and Z are CH} |
| CH | H | $CF_3$ | 3-$CF_3$ | N | $CH_2CH_3$ | $CF_3$ | 3-$CF_3$ |
| CH | H | $CF_3$ | 3-$OCF_3$ | N | $CH_2CH_3$ | $CF_3$ | 3-$OCF_3$ |
| CH | H | $CF_3$ | 3-$SCF_3$ | N | $CH_2CH_3$ | $CF_3$ | 3-$SCF_3$ |
| CH | H | $CF_3$ | 3-$OCHF_2$ | N | $CH_2CH_3$ | $CF_3$ | 3-$OCHF_2$ |
| CH | H | $CF_3$ | 3-$SCHF_2$ | N | $CH_2CH_3$ | $CF_3$ | 3-$SCHF_2$ |
| CH | H | $CF_3$ | 3-Cl | N | $CH_2CH_3$ | $CF_3$ | 3-Cl |
| CH | H | $OCHF_2$ | 3-$CF_3$ | N | $CH_2CH_3$ | $OCHF_2$ | 3-$CF_3$ |
| CH | H | $OCHF_2$ | 3-$OCF_3$ | N | $CH_2CH_3$ | $OCHF_2$ | 3-$OCF_3$ |
| CH | H | $OCHF_2$ | 3-$SCF_3$ | N | $CH_2CH_3$ | $OCHF_2$ | 3-$SCF_3$ |
| CH | H | $OCHF_2$ | 3-$OCHF_2$ | N | $CH_2CH_3$ | $OCHF_2$ | 3-$OCHF_2$ |
| CH | H | $OCHF_2$ | 3-$SCHF_2$ | N | $CH_2CH_3$ | $OCHF_2$ | 3-$SCHF_2$ |
| CH | H | $OCHF_2$ | 3-Cl | N | $CH_2CH_3$ | $OCHF_2$ | 3-Cl |
| CH | H | $SCHF_2$ | 3-$CF_3$ | N | $CH_2CH_3$ | $SCHF_2$ | 3-$CF_3$ |
| CH | H | $SCHF_2$ | 3-$OCF_3$ | N | $CH_2CH_3$ | $SCHF_2$ | 3-$OCF_3$ |
| CH | H | $SCHF_2$ | 3-$SCF_3$ | N | $CH_2CH_3$ | $SCHF_2$ | 3-$SCF_3$ |
| CH | H | $SCHF_2$ | 3-$OCHF_2$ | N | $CH_2CH_3$ | $SCHF_2$ | 3-$OCHF_2$ |
| CH | H | $SCHF_2$ | 3-$SCHF_2$ | N | $CH_2CH_3$ | $SCHF_2$ | 3-$SCHF_2$ |
| CH | H | $SCHF_2$ | 3-Cl | N | $CH_2CH_3$ | $SCHF_2$ | 3-Cl |
| CH | H | $OCF_3$ | 3-$CF_3$ | N | $CH_2CH_3$ | $OCF_3$ | 3-$CF_3$ |
| CH | H | $OCF_3$ | 3-$OCF_3$ | N | $CH_2CH_3$ | $OCF_3$ | 3-$OCF_3$ |
| CH | H | $OCF_3$ | 3-$SCF_3$ | N | $CH_2CH_3$ | $OCF_3$ | 3-$SCF_3$ |
| CH | H | $OCF_3$ | 3-$OCHF_2$ | N | $CH_2CH_3$ | $OCF_3$ | 3-$OCHF_2$ |
| CH | H | $OCF_3$ | 3-$SCHF_2$ | N | $CH_2CH_3$ | $OCF_3$ | 3-$SCHF_2$ |
| CH | H | $OCF_3$ | 3-Cl | N | $CH_2CH_3$ | $OCF_3$ | 3-Cl |
| CH | H | $SCF_3$ | 3-$CF_3$ | N | $CH_2CH_3$ | $SCF_3$ | 3-$CF_3$ |
| CH | H | $SCF_3$ | 3-$OCF_3$ | N | $CH_2CH_3$ | $SCF_3$ | 3-$OCF_3$ |
| CH | H | $SCF_3$ | 3-$SCF_3$ | N | $CH_2CH_3$ | $SCF_3$ | 3-$SCF_3$ |
| CH | H | $SCF_3$ | 3-$OCHF_2$ | N | $CH_2CH_3$ | $SCF_3$ | 3-$OCHF_2$ |
| CH | H | $SCF_3$ | 3-$SCHF_2$ | N | $CH_2CH_3$ | $SCF_3$ | 3-$SCHF_2$ |
| CH | H | $SCF_3$ | 3-Cl | N | $CH_2CH_3$ | $SCF_3$ | 3-Cl |
| CH | H | Cl | 3-$CF_3$ | N | $CH_2CH_3$ | Cl | 3-$CF_3$ |
| CH | H | Cl | 3-$OCF_3$ | N | $CH_2CH_3$ | Cl | 3-$OCF_3$ |
| CH | H | Cl | 3-$SCF_3$ | N | $CH_2CH_3$ | Cl | 3-$SCF_3$ |
| CH | H | Cl | 3-$OCHF_2$ | N | $CH_2CH_3$ | Cl | 3-$OCHF_2$ |
| CH | H | Cl | 3-$SCHF_2$ | N | $CH_2CH_3$ | Cl | 3-$SCHF_2$ |
| CH | H | Cl | 3-Cl | N | $CH_2CH_3$ | Cl | 3-Cl |
| CH | $CH_3$ | $CF_3$ | 3-$CF_3$ | N | $CH_3$ | $CF_3$ | 3-$CF_3$ |
| CH | $CH_3$ | $CF_3$ | 3-$OCF_3$ | N | $CH_3$ | $CF_3$ | 3-$OCF_3$ |
| CH | $CH_3$ | $CF_3$ | 3-$SCF_3$ | N | $CH_3$ | $CF_3$ | 3-$SCF_3$ |
| CH | $CH_3$ | $CF_3$ | 3-$OCHF_2$ | N | $CH_3$ | $CF_3$ | 3-$OCHF_2$ |
| CH | $CH_3$ | $CF_3$ | 3-$SCHF_2$ | N | $CH_3$ | $CF_3$ | 3-$SCHF_2$ |
| CH | $CH_3$ | $CF_3$ | 3-Cl | N | $CH_3$ | $CF_3$ | 3-Cl |
| CH | $CH_3$ | $OCHF_2$ | 3-$CF_3$ | N | $CH_3$ | $OCHF_2$ | 3-$CF_3$ |
| CH | $CH_3$ | $OCHF_2$ | 3-$OCF_3$ | N | $CH_3$ | $OCHF_2$ | 3-$OCF_3$ |
| CH | $CH_3$ | $OCHF_2$ | 3-$SCF_3$ | N | $CH_3$ | $OCHF_2$ | 3-$SCF_3$ |
| CH | $CH_3$ | $OCHF_2$ | 3-$OCHF_2$ | N | $CH_3$ | $OCHF_2$ | 3-$OCHF_2$ |
| CH | $CH_3$ | $OCHF_2$ | 3-$SCHF_2$ | N | $CH_3$ | $OCHF_2$ | 3-$SCHF_2$ |
| CH | $CH_3$ | $OCHF_2$ | 3-Cl | N | $CH_3$ | $OCHF_2$ | 3-Cl |
| CH | $CH_3$ | $SCHF_2$ | 3-$CF_3$ | N | $CH_3$ | $SCHF_2$ | 3-$CF_3$ |
| CH | $CH_3$ | $SCHF_2$ | 3-$OCF_3$ | N | $CH_3$ | $SCHF_2$ | 3-$OCF_3$ |
| CH | $CH_3$ | $SCHF_2$ | 3-$SCF_3$ | N | $CH_3$ | $SCHF_2$ | 3-$SCF_3$ |
| CH | $CH_3$ | $SCHF_2$ | 3-$OCHF_2$ | N | $CH_3$ | $SCHF_2$ | 3-$OCHF_2$ |
| CH | $CH_3$ | $SCHF_2$ | 3-$SCHF_2$ | N | $CH_3$ | $SCHF_2$ | 3-$SCHF_2$ |
| CH | $CH_3$ | $SCHF_2$ | 3-Cl | N | $CH_3$ | $SCHF_2$ | 3-Cl |
| CH | $CH_3$ | $OCF_3$ | 3-$CF_3$ | N | $CH_3$ | $OCF_3$ | 3-$CF_3$ |
| CH | $CH_3$ | $OCF_3$ | 3-$OCF_3$ | N | $CH_3$ | $OCF_3$ | 3-$OCF_3$ |
| CH | $CH_3$ | $OCF_3$ | 3-$SCF_3$ | N | $CH_3$ | $OCF_3$ | 3-$SCF_3$ |
| CH | $CH_3$ | $OCF_3$ | 3-$OCHF_2$ | N | $CH_3$ | $OCF_3$ | 3-$OCHF_2$ |
| CH | $CH_3$ | $OCF_3$ | 3-$SCHF_2$ | N | $CH_3$ | $OCF_3$ | 3-$SCHF_2$ |
| CH | $CH_3$ | $OCF_3$ | 3-Cl | N | $CH_3$ | $OCF_3$ | 3-Cl |
| CH | $CH_3$ | $SCF_3$ | 3-$CF_3$ | N | $CH_3$ | $SCF_3$ | 3-$CF_3$ |
| CH | $CH_3$ | $SCF_3$ | 3-$OCF_3$ | N | $CH_3$ | $SCF_3$ | 3-$OCF_3$ |
| CH | $CH_3$ | $SCF_3$ | 3-$SCF_3$ | N | $CH_3$ | $SCF_3$ | 3-$SCF_3$ |
| CH | $CH_3$ | $SCF_3$ | 3-$OCHF_2$ | N | $CH_3$ | $SCF_3$ | 3-$OCHF_2$ |
| CH | $CH_3$ | $SCF_3$ | 3-$SCHF_2$ | N | $CH_3$ | $SCF_3$ | 3-$SCHF_2$ |

TABLE 1-continued

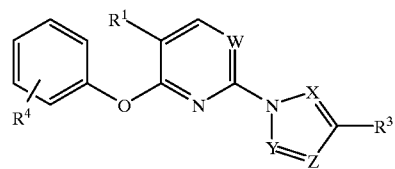

| W | R¹ | R³ | R⁴ | W | R¹ | R³ | R⁴ |
|---|---|---|---|---|---|---|---|
| CH | $CH_3$ | $SCF_3$ | 3-Cl | N | $CH_3$ | $SCF_3$ | 3-Cl |
| CH | $CH_3$ | Cl | 3-$CF_3$ | N | $CH_3$ | Cl | 3-$CF_3$ |
| CH | $CH_3$ | Cl | 3-$OCF_3$ | N | $CH_3$ | Cl | 3-$OCF_3$ |
| CH | $CH_3$ | Cl | 3-$SCF_3$ | N | $CH_3$ | Cl | 3-$SCF_3$ |
| CH | $CH_3$ | Cl | 3-$OCHF_2$ | N | $CH_3$ | Cl | 3-$OCHF_2$ |
| CH | $CH_3$ | Cl | 3-$SCHF_2$ | N | $CH_3$ | Cl | 3-$SCHF_2$ |
| CH | $CH_3$ | Cl | 3-Cl | N | $CH_3$ | Cl | 3-Cl |
| CH | $OCH_3$ | $CF_3$ | 3-$CF_3$ | N | $OCH_3$ | $CF_3$ | 3-$CF_3$ |
| CH | $OCH_3$ | $CF_3$ | 3-$OCF_3$ | N | $OCH_3$ | $CF_3$ | 3-$OCF_3$ |
| CH | $OCH_3$ | $CF_3$ | 3-$SCF_3$ | N | $OCH_3$ | $CF_3$ | 3-$SCF_3$ |
| CH | $OCH_3$ | $CF_3$ | 3-$OCHF_2$ | N | $6CH_3$ | $CF_3$ | 3-$OCHF_2$ |
| CH | $OCH_3$ | $CF_3$ | 3-$SCHF_2$ | N | $OCH_3$ | $CF_3$ | 3-$SCHF_2$ |
| CH | $OCH_3$ | $CF_3$ | 3-Cl | N | $OCH_3$ | $CF_3$ | 3-Cl |
| CH | $OCH_3$ | $OCHF_2$ | 3-$CF_3$ | N | $OCH_3$ | $OCHF_2$ | 3-$CF_3$ |
| CH | $OCH_3$ | $OCHF_2$ | 3-$OCF_3$ | N | $OCH_3$ | $OCHF_2$ | 3-$OCF_3$ |
| CH | $OCH_3$ | $OCHF_2$ | 3-$SCF_3$ | N | $OCH_3$ | $OCHF_2$ | 3-$SCF_3$ |
| CH | $OCH_3$ | $OCHF_2$ | 3-$OCHF_2$ | N | $OCH_3$ | $OCHF_2$ | 3-$OCHF_2$ |
| CH | $OCH_3$ | $OCHF_2$ | 3-$SCHF_2$ | N | $OCH_3$ | $OCHF_2$ | 3-$SCHF_2$ |
| CH | $OCH_3$ | $OCHF_2$ | 3-Cl | N | $OCH_3$ | $OCHF_2$ | 3-Cl |
| CH | $OCH_3$ | $SCHF_2$ | 3-$CF_3$ | N | $OCH_3$ | $SCHF_2$ | 3-$CF_3$ |
| CH | $OCH_3$ | $SCHF_2$ | 3-$OCF_3$ | N | $OCH_3$ | $SCHF_2$ | 3-$OCF_3$ |
| CH | $OCH_3$ | $SCHF_2$ | 3-$SCF_3$ | N | $OCH_3$ | $SCHF_2$ | 3-$SCF_3$ |
| CH | $OCH_3$ | $SCHF_2$ | 3-$OCHF_2$ | N | $OCH_3$ | $SCHF_2$ | 3-$OCHF_2$ |
| CH | $OCH_3$ | $SCHF_2$ | 3-$SCHF_2$ | N | $OCH_3$ | $SCHF_2$ | 3-$SCHF_2$ |
| CH | $OCH_3$ | $SCHF_2$ | 3-Cl | N | $OCH_3$ | $SCHF_2$ | 3-Cl |
| CH | $OCH_3$ | $OCF_3$ | 3-$CF_3$ | N | $OCH_3$ | $OCF_3$ | 3-$CF_3$ |
| CH | $OCH_3$ | $OCF_3$ | 3-$OCF_3$ | N | $OCH_3$ | $OCF_3$ | 3-$OCF_3$ |
| CH | $OCH_3$ | $OCF_3$ | 3-$SCF_3$ | N | $OCH_3$ | $OCF_3$ | 3-$SCF_3$ |
| CH | $OCH_3$ | $OCF_3$ | 3-$OCHF_2$ | N | $OCH_3$ | $OCF_3$ | 3-$OCHF_2$ |
| CH | $OCH_3$ | $OCF_3$ | 3-$SCHF_2$ | N | $OCH_3$ | $OCF_3$ | 3-$SCHF_2$ |
| CH | $OCH_3$ | $OCF_3$ | 3-Cl | N | $OCH_3$ | $OCF_3$ | 3-Cl |
| CH | $OCH_3$ | $SCF_3$ | 3-$CF_3$ | N | $OCH_3$ | $SCF_3$ | 3-$CF_3$ |
| CH | $OCH_3$ | $SCF_3$ | 3-$OCF_3$ | N | $OCH_3$ | $SCF_3$ | 3-$OCF_3$ |
| CH | $OCH_3$ | $SCF_3$ | 3-$SCF_3$ | N | $OCH_3$ | $SCF_3$ | 3-$SCF_3$ |
| CH | $OCH_3$ | $SCF_3$ | 3-$OCHF_2$ | N | $OCH_3$ | $SCF_3$ | 3-$OCHF_2$ |
| CH | $OCH_3$ | $SCF_3$ | 3-$SCHF_2$ | N | $OCH_3$ | $SCF_3$ | 3-$SCHF_2$ |
| CH | $OCH_3$ | $SCF_3$ | 3-Cl | N | $OCH_3$ | $SCF_3$ | 3-Cl |
| CH | $OCH_3$ | Cl | 3-$CF_3$ | N | $OCH_3$ | Cl | 3-$CF_3$ |
| CH | $OCH_3$ | Cl | 3-$OCF_3$ | N | $OCH_3$ | Cl | 3-$OCF_3$ |
| CH | $OCH_3$ | Cl | 3-$SCF_3$ | N | $OCH_3$ | Cl | 3-$SCF_3$ |
| CH | $OCH_3$ | Cl | 3-$OCHF_2$ | N | $OCH_3$ | Cl | 3-$OCHF_2$ |
| CH | $OCH_3$ | Cl | 3-$SCHF_2$ | N | $OCH_3$ | Cl | 3-$SCHF_2$ |
| CH | $OCH_3$ | Cl | 3-Cl | N | $OCH_3$ | Cl | 3-Cl |
| \multicolumn{8}{c}{wherein Z is N and X and Y are CH} |
| CH | H | $CF_3$ | 3-$CF_3$ | N | $CH_2CH_3$ | $CF_3$ | 3-$CF_3$ |
| CH | H | $CF_3$ | 3-$OCF_3$ | N | $CH_2CH_3$ | $CF_3$ | 3-$OCF_3$ |
| CH | H | $CF_3$ | 3-$SCF_3$ | N | $CH_2CH_3$ | $CF_3$ | 3-$SCF_3$ |
| CH | H | $CF_3$ | 3-$OCHF_2$ | N | $CH_2CH_3$ | $CF_3$ | 3-$OCHF_2$ |
| CH | H | $CF_3$ | 3-$SCHF_2$ | N | $CH_2CH_3$ | $CF_3$ | 3-$SCHF_2$ |
| CH | H | $CF_3$ | 3-Cl | N | $CH_2CH_3$ | $CF_3$ | 3-Cl |
| CH | H | $OCHF_2$ | 3-$CF_3$ | N | $CH_2CH_3$ | $OCHF_2$ | 3-$CF_3$ |
| CH | H | $OCHF_2$ | 3-$OCF_3$ | N | $CH_2CH_3$ | $OCHF_2$ | 3-$OCF_3$ |
| CH | H | $OCHF_2$ | 3-$SCF_3$ | N | $CH_2CH_3$ | $OCHF_2$ | 3-$SCF_3$ |
| CH | H | $OCHF_2$ | 3-$OCHFZ$ | N | $CH_2CH_3$ | $OCHF_2$ | 3-$OCHF_2$ |
| CH | H | $OCHF_2$ | 3-$SCHF_2$ | N | $CH_2CH_3$ | $OCHF_2$ | 3-$SCHF_2$ |
| CH | H | $OCHF_2$ | 3-Cl | N | $CH_2CH_3$ | $OCHF_2$ | 3-Cl |
| CH | H | $SCHF_2$ | 3-$CF_3$ | N | $CH_2CH_3$ | $SCHF_2$ | 3-$CF_3$ |
| CH | H | $SCHF_2$ | 3-$OCF_3$ | N | $CH_2CH_3$ | $SCHF_2$ | 3-$OCF_3$ |
| CH | H | $SCHF_2$ | 3-$SCF_3$ | N | $CH_2CH_3$ | $S\&HF_2$ | 3-$SCF_3$ |
| CH | H | $SCHF_2$ | 3-$OCHF_2$ | N | $CH_2CH_3$ | $SCHF_2$ | 3-$OCHF_2$ |
| CH | H | $SCHF_2$ | 3-$SCHF_2$ | N | $CH_2CH_3$ | $SCHF_2$ | 3-$SCHF_2$ |
| CH | H | $SCHF_2$ | 3-Cl | N | $CH_2CH_3$ | $SCHF_2$ | 3-Cl |
| CH | H | $OCF_3$ | 3-$CF_3$ | N | $CH_2CH_3$ | $OCF_3$ | 3-$CF_3$ |
| CH | H | $OCF_3$ | 3-$OCF_3$ | N | $CH_2CH_3$ | $OCF_3$ | 3-$OCF_3$ |
| CH | H | $OCF_3$ | 3-$SCF_3$ | N | $CH_2CH_3$ | $OCF_3$ | 3-$SCF_3$ |
| CH | H | $OCF_3$ | 3-$OCHF_2$ | N | $CH_2CH_3$ | $OCF_3$ | 3-$OCHF_2$ |

TABLE 1-continued

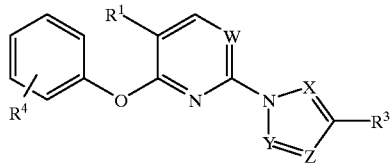

| W | R¹ | R³ | R⁴ | W | R¹ | R³ | R⁴ |
|---|---|---|---|---|---|---|---|
| CH | H | OCF₃ | 3-SCHF₂ | N | CH₂CH₃ | OCF₃ | 3-SCHF₂ |
| CH | H | OCF₃ | 3-Cl | N | CH₂CH₃ | OCF₃ | 3-Cl |
| CH | H | SCF₃ | 3-CF₃ | N | CH₂CH₃ | SCF₃ | 3-CF₃ |
| CH | H | SCF₃ | 3-OCF₃ | N | CH₂CH₃ | SCF₃ | 3-OCF₃ |
| CH | H | SCF₃ | 3-SCF₃ | N | CH₂CH₃ | SCF₃ | 3-SCF₃ |
| CH | H | SCF₃ | 3-OCHF₂ | N | CH₂CH₃ | SCF₃ | 3-OCHF₂ |
| CH | H | SCF₃ | 3-SCHF₂ | N | CH₂CH₃ | SCF₃ | 3-SCHF₂ |
| CH | H | SCF₃ | 3-Cl | N | CH₂CH₃ | SCF₃ | 3-Cl |
| CH | H | Cl | 3-CF₃ | N | CH₂CH₃ | Cl | 3-CF₃ |
| CH | H | Cl | 3-OCF₃ | N | CH₂CH₃ | Cl | 3-OCF₃ |
| CH | H | Cl | 3-SCF₃ | N | CH₂CH₃ | Cl | 3-SCF₃ |
| CH | H | Cl | 3-OCHF₂ | N | CH₂CH₃ | Cl | 3-OCHF₂ |
| CH | H | Cl | 3-SCHF₂ | N | CH₂CH₃ | Cl | 3-SCHF₂ |
| CH | H | Cl | 3-Cl | N | CH₂CH₃ | Cl | 3-Cl |
| CH | CH₃ | CF₃ | 3-CF₃ | N | CH₃ | CF₃ | 3-CF₃ |
| CH | CH₃ | CF₃ | 3-OCF₃ | N | CH₃ | CF₃ | 3-OCF₃ |
| CH | CH₃ | CF₃ | 3-SCF₃ | N | CH₃ | CF₃ | 3-SCF₃ |
| CH | CH₃ | CF₃ | 3-OCHF₂ | N | CH₃ | CF₃ | 3-OCHF₂ |
| CH | CH₃ | CF₃ | 3-SCHF₂ | N | CH₃ | CF₃ | 3-SCHF₂ |
| CH | CH₃ | CF₃ | 3-Cl | N | CH₃ | CF₃ | 3-Cl |
| CH | CH₃ | OCHF₂ | 3-CF₃ | N | CH₃ | OCHF₂ | 3-CF₃ |
| CH | CH₃ | OCHF₂ | 3-OCF₃ | N | CH₃ | OCHF₂ | 3-OCF₃ |
| CH | CH₃ | OCHF₂ | 3-SCF₃ | N | CH₃ | OCHF₂ | 3-SCF₃ |
| CH | CH₃ | OCHF₂ | 3-OCHF₂ | N | CH₃ | OCHF₂ | 3-OCHF₂ |
| CH | CH₃ | OCHF₂ | 3-SCHF₂ | N | CH₃ | CCHF₂ | 3-SCHF₂ |
| CH | CH₃ | OCHF₂ | 3-Cl | N | CH₃ | OCHF₂ | 3-Cl |
| CH | CH₃ | SCHF₂ | 3-CF₃ | N | CH₃ | SCHF₂ | 3-CF₃ |
| CH | CH₃ | SCHF₂ | 3-OCF₃ | N | CH₃ | SCHF₂ | 3-OCF₃ |
| CH | CH₃ | SCHF₂ | 3-SCF₃ | N | CH₃ | SCHF₂ | 3-SCF₃ |
| CH | CH₃ | SCHF₂ | 3-OCHF₂ | N | CH₃ | SCHF₂ | 3-OCHF₂ |
| CH | CH₃ | SCHF₂ | 3-SCHF₂ | N | CH₃ | SCHF₂ | 3-SCHF₂ |
| CH | CH₃ | SCHF₂ | 3-Cl | N | CH₃ | SCHF₂ | 3-Cl |
| CH | CH₃ | OCF₃ | 3-CF₃ | N | CH₃ | OCF₃ | 3-CF₃ |
| CH | CH₃ | OCF₃ | 3-OCF₃ | N | CH₃ | OCF₃ | 3-OCF₃ |
| CH | CH₃ | OCF₃ | 3-SCF₃ | N | CH₃ | OCF₃ | 3-SCF₃ |
| CH | CH₃ | OCF₃ | 3-OCHF₂ | N | CH₃ | OCF₃ | 3-OCHF₂ |
| CH | CH₃ | OCF₃ | 3-SCHF₂ | N | CH₃ | OCF₃ | 3-SCHF₂ |
| CH | CH₃ | OCF₃ | 3-Cl | N | CH₃ | OCF₃ | 3-Cl |
| CH | CH₃ | SCF₃ | 3-CF₃ | N | CH₃ | SCF₃ | 3-CF₃ |
| CH | CH₃ | SCF₃ | 3-OCF₃ | N | CH₃ | SCF₃ | 3-OCF₃ |
| CH | CH₃ | SCF₃ | 3-SCF₃ | N | CH₃ | SCF₃ | 3-SCF₃ |
| CH | CH₃ | SCF₃ | 3-OCHF₂ | N | CFl3 | SCF₃ | 3-OCHF₂ |
| CH | CH₃ | SCF₃ | 3-SCHF₂ | N | CH₃ | SCF₃ | 3-SCHF₂ |
| CH | CH₃ | SCF₃ | 3-Cl | N | CH₃ | SCF₃ | 3-Cl |
| CH | CH₃ | Cl | 3-CF₃ | N | CH₃ | Cl | 3-CF₃ |
| CH | CH₃ | Cl | 3-OCF₃ | N | CH₃ | Cl | 3-OCF₃ |
| CH | CH₃ | Cl | 3-SCF₃ | N | CH₃ | Cl | 3-SCF₃ |
| CH | CH₃ | Cl | 3-OCHF₂ | N | CH₃ | Cl | 3-OCHF₂ |
| CH | CH₃ | Cl | 3-SCHF₂ | N | CH₃ | Cl | 3-SCHF₂ |
| CH | CH₃ | Cl | 3-Cl | N | CH₃ | Cl | 3-Cl |
| CH | OCH₃ | CF₃ | 3-CF₃ | N | OCH₃ | CF₃ | 3-CF₃ |
| CH | OCH₃ | CF₃ | 3-OCF₃ | N | OCH₃ | CF₃ | 3-OCF₃ |
| CH | OCH₃ | CF₃ | 3-SCF₃ | N | OCH₃ | CF₃ | 3-SCF₃ |
| CH | OCH₃ | CF₃ | 3-OCHF₂ | N | OCH₃ | CF₃ | 3-OCHF₂ |
| CH | OCH₃ | CF₃ | 3-SCHF₂ | N | OCH₃ | CF₃ | 3-SCHF₂ |
| CH | OCH₃ | CF₃ | 3-Cl | N | 09H₃ | CF₃ | 3-Cl |
| CH | OCH₃ | OCHF₂ | 3-CF₃ | N | OCH₃ | OCHF₂ | 3-CF₃ |
| CH | OCH₃ | OCHF₂ | 3-OCF₃ | N | OCH₃ | OCHF₂ | 3-OCF₃ |
| CH | OCH₃ | OCHF₂ | 3-SCF₃ | N | OCH₃ | OCHF₂ | 3-SCF₃ |
| CH | OCH₃ | OCHF₂ | 3-OCHF₂ | N | OCH₃ | OCHF₂ | 3-OCHF₂ |
| CH | OCH₃ | OCHF₂ | 3-SCHF₂ | N | OCH₃ | OCHF₂ | 3-SCHF₂ |
| CH | OCH₃ | OCHF₂ | 3-Cl | N | OCH₃ | OCHF₂ | 3-Cl |
| CH | OCH₃ | SCHF₂ | 3-CF₃ | N | OCH₃ | SCHF₂ | 3-CF₃ |
| CH | OCH₃ | SCHF₂ | 3-OCF₃ | N | OCH₃ | SCHF₂ | 3-OCF₃ |
| CH | OCH₃ | SCHF₂ | 3-SCF₃ | N | OCH₃ | SCHF₂ | 3-SCF₃ |
| CH | OCH₃ | SCHF₂ | 3-OCHF₂ | N | OCH₃ | SCHF₂ | 3-OCHF₂ |
| CH | OCH₃ | SCHF₂ | 3-SCHF₂ | N | OCH₃ | SCHF₂ | 3-SCHF₂ |

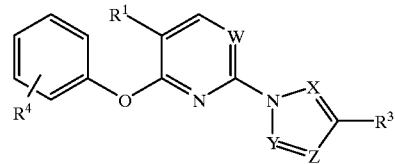

| W | R¹ | R³ | R⁴ | W | R¹ | R³ | R⁴ |
|---|---|---|---|---|---|---|---|
| CH | OCH₃ | SCHF₂ | 3-Cl | N | OCH₃ | SCHF₂ | 3-Cl |
| CH | OCH₃ | OCF₃ | 3-CF₃ | N | OCH₃ | OCF₃ | 3-CF₃ |
| CH | OCH₃ | OCF₃ | 3-OCF₃ | N | OCH₃ | OCF₃ | 3-OCF₃ |
| CH | OCH₃ | OCF₃ | 3-SCF₃ | N | OCH₃ | OCF₃ | 3-SCF₃ |
| CH | OCH₃ | OCF₃ | 3-OCHF₂ | N | OCH₃ | OCF₃ | 3-OCHF₂ |
| CH | OCH₃ | OCF₃ | 3-SCHF₂ | N | OCH₃ | OCF₃ | 3-SCHF₂ |
| CH | OCH₃ | OCF₃ | 3-Cl | N | OCH₃ | OCF₃ | 3-Cl |
| CH | OCH₃ | SCF₃ | 3-CF₃ | N | OCH₃ | SCF₃ | 3-CF₃ |
| CH | OCH₃ | SCF₃ | 3-OCF₃ | N | OCH₃ | SCF₃ | 3-OCF₃ |
| CH | OCH₃ | SCF₃ | 3-SCF₃ | N | OCH₃ | SCF₃ | 3-SCF₃ |
| CH | OCH₃ | SCF₃ | 3-OCHF₂ | N | OCH₃ | SCF₃ | 3-OCHF₂ |
| CH | OCH₃ | SCF₃ | 3-SCHF₂ | N | OCH₃ | SCF₃ | 3-SCHF₂ |
| CH | OCH₃ | SCF₃ | 3-Cl | N | OCH₃ | SCF₃ | 3-Cl |
| CH | OCH₃ | Cl | 3-CF₃ | N | OCH₃ | Cl | 3-CF₃ |
| CH | OCH₃ | Cl | 3-OCF₃ | N | OCH₃ | Cl | 3-OCF₃ |
| CH | OCH₃ | Cl | 3-SCF₃ | N | OCH₃ | Cl | 3-SCF₃ |
| CH | OCH₃ | Cl | 3-OCHF₂ | N | OCH₃ | Cl | 3-OCHF₂ |
| CH | OCH₃ | Cl | 3-SCHF₂ | N | OCH₃ | Cl | 3-SCHF₂ |
| CH | OCH₃ | Cl | 3-Cl | N | OCH₃ | Cl | 3-Cl |

TABLE 2

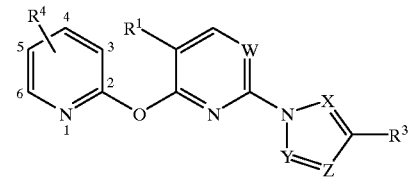

wherein X is N and Y and Z are CH

| W | R¹ | R³ | R⁴ | W | R¹ | R³ | R⁴ |
|---|---|---|---|---|---|---|---|
| CH | H | CF₃ | 6-CF₃ | N | CH₂CH₃ | CF₃ | 6-CF₃ |
| CH | H | CF₃ | 6-OCF₃ | N | CH₂CH₃ | CF₃ | 6-OCF₃ |
| CH | H | OCHF₂ | 6-CF₃ | N | CH₂CH₃ | OCHF₂ | 6-CF₃ |
| CH | H | OCHF₂ | 6-OCF₃ | N | CH₂CH₃ | OCHF₂ | 6-OCF₃ |
| CH | H | SCHF₂ | 6-CF₃ | N | CH₂CH₃ | SCHF₂ | 6-CF₃ |
| CH | H | SCHF₂ | 6-OCF₃ | N | CH₂CH₃ | SCHF₂ | 6-OCF₃ |
| CH | H | OCF₃ | 6-CF₃ | N | CH₂CH₃ | OCF₃ | 6-CF₃ |
| CH | H | OCF₃ | 6-OCF₃ | N | CH₂CH₃ | OCF₃ | 6-OCF₃ |
| CH | H | SCF₃ | 6-CF₃ | N | CH₂CH₃ | SCF₃ | 6-CF₃ |
| CH | H | SCF₃ | 6-OCF₃ | N | CH₂CH₃ | SCF₃ | 6-OCF₃ |
| CH | H | Cl | 6-CF₃ | N | CH₂CH₃ | Cl | 6-CF₃ |
| CH | H | Cl | 6-OCF₃ | N | CH₂CH₃ | Cl | 6-OCF₃ |
| CH | CH₃ | CF₃ | 6-CF₃ | N | CH₃ | CF₃ | 6-CF₃ |
| CH | CH₃ | CF₃ | 6-OCF₃ | N | CH₃ | CF₃ | 6-OCF₃ |
| CH | CH₃ | OCHF₂ | 6-CF₃ | N | CH₃ | OCHF₂ | 6-CF₃ |
| CH | CH₃ | OCHF₂ | 6-OCF₃ | N | CH₃ | OCHF₂ | 6-OCF₃ |
| CH | CH₃ | SCHF₂ | 6-CF₃ | N | CH₃ | SCHF₂ | 6-CF₃ |
| CH | CH₃ | SCHF₂ | 6-OCF₃ | N | CH₃ | SCHF₂ | 6-OCF₃ |
| CH | CH₃ | OCF₃ | 6-CF₃ | N | CH₃ | OCF₃ | 6-CF₃ |
| CH | CH₃ | OCF₃ | 6-OCF₃ | N | CH₃ | OCF₃ | 6-OCF₃ |
| CH | CH₃ | SCF₃ | 6-CF₃ | N | CH₃ | SCF₃ | 6-CF₃ |
| CH | CH₃ | SCF₃ | 6-OCF₃ | N | CH₃ | SCF₃ | 6-OCF₃ |
| CH | CH₃ | Cl | 6-CF₃ | N | CH₃ | Cl | 6-CF₃ |
| CH | CH₃ | Cl | 6-OCF₃ | N | CH₃ | Cl | 6-OCF₃ |
| CH | OCH₃ | CF₃ | 6-CF₃ | N | OCH₃ | CF₃ | 6-CF₃ |
| CH | OCH₃ | CF₃ | 6-OCF₃ | N | OCH₃ | CF₃ | 6-OCF₃ |
| CH | OCH₃ | OCHF₂ | 6-CF₃ | N | OCH₃ | OCHF₂ | 6-CF₃ |
| CH | OCH₃ | OCHF₂ | 6-OCF₃ | N | OCH₃ | OCHF₂ | 6-OCF₃ |
| CH | OCH₃ | SCHF₂ | 6-CF₃ | N | OCH₃ | SCHF₂ | 6-CF₃ |

TABLE 2-continued

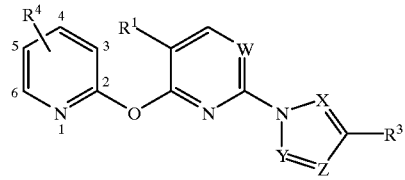

| W | R¹ | R³ | R⁴ | W | R¹ | R³ | R⁴ |
|---|---|---|---|---|---|---|---|
| CH | OCH₃ | SCHF₂ | 6-OCF₃ | N | OCH₃ | SCHF₂ | 6-OCF₃ |
| CH | OCH₃ | OCF₃ | 6-CF₃ | N | OCH₃ | OCF₃ | 6-CF₃ |
| CH | OCH₃ | OCF₃ | 6-OCF₃ | N | OCH₃ | OCF₃ | 6-OCF₃ |
| CH | OCH₃ | SCF₃ | 6-CF₃ | N | OCH₃ | SCF₃ | 6-CF₃ |
| CH | OCH₃ | SCF₃ | 6-OCF₃ | N | OCH₃ | SCF₃ | 6-OCF₃ |
| CH | OCH₃ | Cl | 6-CF₃ | N | OCH₃ | Cl | 6-CF₃ |
| CH | OCH₃ | Cl | 6-OCF₃ | N | OCH₃ | Cl | 6-OCF₃ |
| | wherein Z is N and X and Y are CH |
| CH | H | CF₃ | 6-CF₃ | N | CH₂CH₃ | CF₃ | 6-CF₃ |
| CH | H | CF₃ | 6-OCF₃ | N | CH₂CH₃ | CF₃ | 6-OCF₃ |
| CH | H | OCHF₂ | 6-CF₃ | N | CH₂CH₃ | OCHF₂ | 6-CF₃ |
| CH | H | OCHF₂ | 6-OCF₃ | N | CH₂CH₃ | OCHF₂ | 6-OCF₃ |
| CH | H | SCHF₂ | 6-CF₃ | N | CH₂CH₃ | SCHF₂ | 6-CF₃ |
| CH | H | SCHF₂ | 6-OCF₃ | N | CH₂CH₃ | SCHF₂ | 6-OCF₃ |
| CH | H | OCF₃ | 6-CF₃ | N | CH₂CH₃ | OCF₃ | 6-CF₃ |
| CH | H | OCF₃ | 6-OCF₃ | N | CH₂CH₃ | OCF₃ | 6-OCF₃ |
| CH | H | SCF₃ | 6-CF₃ | N | CH₂CH₃ | SCF₃ | 6-CF₃ |
| CH | H | SCF₃ | 6-OCF₃ | N | CH₂CH₃ | SCF₃ | 6-OCF₃ |
| CH | H | Cl | 6-CF₃ | N | CH₂CH₃ | Cl | 6-CF₃ |
| CH | H | Cl | 6-OCF₃ | N | CH₂CH₃ | Cl | 6-OCF₃ |
| CH | CH₃ | CF₃ | 6-CF₃ | N | CH₃ | CF₃ | 6-CF₃ |
| CH | CH₃ | CF₃ | 6-OCF₃ | N | CH₃ | CF₃ | 6-OCF₃ |
| CH | CH₃ | OCHF₂ | 6-CF₃ | N | CH₃ | OCHF₂ | 6-CF₃ |
| CH | CH₃ | OCHF₂ | 6-OCF₃ | N | CH₃ | OCHF₂ | 6-OCF₃ |
| CH | CH₃ | SCHF₂ | 6-CF₃ | N | CH₃ | SCHF₂ | 6-CF₃ |
| CH | CH₃ | SCHF₂ | 6-OCF₃ | N | CH₃ | SCHF₂ | 6-OCF₃ |
| CH | CH₃ | OCF₃ | 6-CF₃ | N | CH₃ | OCF₃ | 6-CF₃ |
| CH | CH₃ | OCF₃ | 6-OCF₃ | N | CH₃ | OCF₃ | 6-OCF₃ |
| CH | CH₃ | SCF₃ | 6-CF₃ | N | CH₃ | SCF₃ | 6-CF₃ |
| CH | CH₃ | SCF₃ | 6-OCF₃ | N | CH₃ | SCF₃ | 6-OCF₃ |
| CH | CH₃ | Cl | 6-CF₃ | N | CH₃ | Cl | 6-CF₃ |
| CH | CH₃ | Cl | 6-OCF₃ | N | CH₃ | Cl | 6-OCF₃ |
| CH | OCH₃ | CF₃ | 6-CF₃ | N | OCH₃ | CF₃ | 6-CF₃ |
| CH | OCH₃ | CF₃ | 6-OCF₃ | N | OCH₃ | CF₃ | 6-OCF₃ |
| CH | OCH₃ | OCHF₂ | 6-CF₃ | N | OCH₃ | OCHF₂ | 6-CF₃ |
| CH | OCH₃ | OCHF₂ | 6-OCF₃ | N | OCH₃ | OCHF₂ | 6-OCF₃ |
| CH | OCH₃ | SCHF₂ | 6-CF₃ | N | OCH₃ | SCHF₂ | 6-CF₃ |
| CH | OCH₃ | SCHF₂ | 6-OCF₃ | N | OCH₃ | SCHF₂ | 6-OCF₃ |
| CH | OCH₃ | OCF₃ | 6-CF₃ | N | OCH₃ | OCF₃ | 6-CF₃ |
| CH | OCH₃ | OCF₃ | 6-OCF₃ | N | OCH₃ | OCF₃ | 6-OCF₃ |
| CH | OCH₃ | SCF₃ | 6-CF₃ | N | OCH₃ | SCF₃ | 6-CF₃ |
| CH | OCH₃ | SCF₃ | 6-OCF₃ | N | OCH₃ | SCF₃ | 6-OCF₃ |
| CH | OCH₃ | Cl | 6-CF₃ | N | OCH₃ | Cl | 6-CF₃ |
| CH | OCH₃ | Cl | 6-OCF₃ | N | OCH₃ | Cl | 6-OCF₃ |

TABLE 3

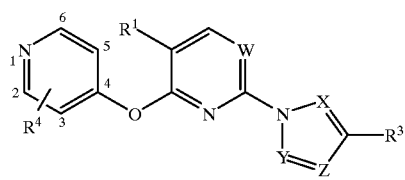

| W | R¹ | R³ | R⁴ | W | R¹ | R³ | R⁴ |
|---|---|---|---|---|---|---|---|
| | wherein X is N and Y and Z are CH |
| CH | H | CH₃ | 2-CF₃ | N | CH₂CH₃ | CF₃ | 2-CF₃ |
| CH | H | CF₃ | 2-OCF₃ | N | CH₂CH₃ | CF₃ | 2-OCF₃ |
| CH | H | OCHF₂ | 2-CF₃ | N | CH₂CH₃ | OCHF₂ | 2-CF₃ |

TABLE 3-continued

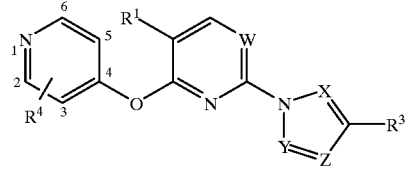

| W | R¹ | R³ | R⁴ | W | R¹ | R³ | R⁴ |
|---|---|---|---|---|---|---|---|
| CH | H | OCHF₂ | 2-OCF₃ | N | CH₂CH₃ | OCHF₂ | 2-OCF₃ |
| CH | H | SCHF₂ | 2-CF₃ | N | CH₂CH₃ | SCHF₂ | 2-CF₃ |
| CH | H | SCHF₂ | 2-OCF₃ | N | CH₂CH₃ | SCF₂ | 2-OCF₃ |
| CH | H | OCF₃ | 2-CF₃ | N | CH₂CH₃ | OCF₃ | 2-CF₃ |
| CH | H | OCF₃ | 2-OCF₃ | N | CH₂CH₃ | OCF₃ | 2-OCF₃ |
| CH | H | SCF₃ | 2-CF₃ | N | CH₂CH₃ | SCF₃ | 2-CF₃ |
| CH | H | SCF₃ | 2-OCF₃ | N | CH₂CH₃ | SCF₃ | 2-OCF₃ |
| CH | H | Cl | 2-CF₃ | N | CH₂CH₃ | Cl | 2-CF₃ |
| CH | H | Cl | 2-OCF₃ | N | CH₂CH₃ | Cl | 2-OCF₃ |
| CH | CH₃ | CF₃ | 2-CF₃ | N | CH₃ | CF₃ | 2-CF₃ |
| CH | CH₃ | CF₃ | 2-OCF₃ | N | CH₃ | CF₃ | 2-OCF₃ |
| CH | CH₃ | OCHF₂ | 2-CF₃ | N | CH₃ | OCHF₂ | 2-CF₃ |
| CH | CH₃ | OCHF₂ | 2-OCF₃ | N | CH₃ | OCHF₂ | 2-OCF₃ |
| CH | CH₃ | SCHF₂ | 2-CF₃ | N | CH₃ | SCHF₂ | 2-CF₃ |
| CH | CH₃ | SCHF₂ | 2-OCF₃ | N | CH₃ | SCHF₂ | 2-OCF₃ |
| CH | CH₃ | OCF₃ | 2-CF₃ | N | CH₃ | OCF₃ | 2-CF₃ |
| CH | CH₃ | OCF₃ | 2-OCF₃ | N | CH₃ | OCF₃ | 2-OCF₃ |
| CH | CH₃ | SCF₃ | 2-CF₃ | N | CH₃ | SCF₃ | 2-CF₃ |
| CH | CH₃ | SCF₃ | 2-OCF₃ | N | CH₃ | SCF₃ | 2-OCF₃ |
| CH | CH₃ | Cl | 2-CF₃ | N | CH₃ | Cl | 2-CF₃ |
| CH | CH₃ | Cl | 2-OCF₃ | N | CH₃ | Cl | 2-OCF₃ |
| CH | OCH₃ | CF₃ | 2-CF₃ | N | OCH₃ | CF₃ | 2-CF₃ |
| CH | OCH₃ | CF₃ | 2-OCF₃ | N | OCH₃ | OF₃ | 2-OCF₃ |
| CH | OCH₃ | OCHF₂ | 2-CF₃ | N | OCH₃ | OCHF₂ | 2-CF₃ |
| CH | OCH₃ | OCHF₂ | 2-OCF₃ | N | OCH₃ | OCHF₂ | 2-OCF₃ |
| CH | OCH₃ | SCHF₂ | 2-CF₃ | N | OCH₃ | SCHF₂ | 2-CF₃ |
| CH | OCH₃ | SCHF₂ | 2-OCF₃ | N | OCH₃ | SCHF₂ | 2-OCF₃ |
| CH | OCH₃ | OCF₃ | 2-CF₃ | N | OCH₃ | OCF₃ | 2-CF₃ |
| CH | OCH₃ | OCF₃ | 2-OCF₃ | N | OCH₃ | OCF₃ | 2-OCF₃ |
| CH | OCH₃ | SCF₃ | 2-CF₃ | N | OCH₃ | SCF₃ | 2-CF₃ |
| CH | OCH₃ | SCF₃ | 2-OCF₃ | N | OCH₃ | SCF₃ | 2-OCF₃ |
| CH | OCH₃ | Cl | 2-CF₃ | N | OCH₃ | Cl | 2-CF₃ |
| CH | OCH₃ | Cl | 2-OCF₃ | N | OCH₃ | Cl | 2-OCF₃ |
| | wherein Z is N and X and Y are CH |
| CH | H | CF₃ | 2-CF₃ | N | CH₂CH₃ | CF₃ | 2-CF₃ |
| CH | H | CF₃ | 2-OCF₃ | N | CH₂CH₃ | CF₃ | 2-OCF₃ |
| CH | H | OCHF₂ | 2-CF₃ | N | CH₂CH₃ | OCHF₂ | 2-CF₃ |
| CH | H | OCHF₂ | 2-OCF₃ | N | CH₂CH₃ | OCHF₂ | 2-OCF₃ |
| CH | H | SCHF₂ | 2-CF₃ | N | CH₂CH₃ | SCHF₂ | 2-CF₃ |
| CH | H | SCHF₂ | 2-OCF₃ | N | CH₂CH₃ | SCHF₂ | 2-OCF₃ |
| CH | H | OCF₃ | 2-CF₃ | N | CH₂CH₃ | OCF₃ | 2-CF₃ |
| CH | H | OCF₃ | 2-OCF₃ | N | CH₂CH₃ | OCF₃ | 2-OCF₃ |
| CH | H | SCF₃ | 2-CF₃ | N | CH₂CH₃ | SCF₃ | 2-CF₃ |
| CH | H | SCF₃ | 2-9CF₃ | N | CH₂CH₃ | SCF₃ | 2-OCF₃ |
| CH | H | Cl | 2-CF₃ | N | CH₂CH₃ | Cl | 2-CF₃ |
| CH | H | Cl | 2-OCF₃ | N | CH₂CH₃ | Cl | 2-OCF₃ |
| CH | CH₃ | CF₃ | 2-CF₃ | N | CH₃ | CF₃ | 2-CF₃ |
| CH | CH₃ | CF₃ | 2-OCF₃ | N | CH₃ | CF₃ | 2-OCF₃ |
| CH | CH₃ | OCHF₂ | 2-CF₃ | N | CH₃ | OCHF₂ | 2-CF₃ |
| CH | CH₃ | OCHF₂ | 2-OCF₃ | N | CH₃ | OCHF₂ | 2-OCF₃ |
| CH | CH₃ | SCHF₂ | 2-CF₃ | N | CH₃ | SCHF₂ | 2-CF₃ |
| CH | CH₃ | SCHF₂ | 2-OCF₃ | N | CH₃ | SCHF₂ | 2-OCF₃ |
| CH | CH₃ | OCF₃ | 2-CF₃ | N | CH₃ | OCF₃ | 2-CF₃ |
| CH | CH₃ | OCF₃ | 2-OCF₃ | N | CH₃ | OCF₃ | 2-OCF₃ |
| CH | CH₃ | SCF₃ | 2-CF₃ | N | CH₃ | SCF₃ | 2-CF₃ |
| CH | CH₃ | SCF₃ | 2-OCF₃ | N | CH₃ | SCF₃ | 2-OCF₃ |
| CH | CH₃ | Cl | 2-CF₃ | N | CH₃ | Cl | 2-CF₃ |
| CH | CH₃ | Cl | 2-OCF₃ | N | CH₃ | Cl | 2-OCF₃ |
| CH | OCH₃ | CF₃ | 2-CF₃ | N | OCH₃ | CF₃ | 2-CF₃ |
| CH | OCH₃ | CF₃ | 2-OCF₃ | N | OCH₃ | CF₃ | 2-OCF₃ |
| CH | OCH₃ | OCHF₂ | 2-CF₃ | N | OCH₃ | OCHF₂ | 2-CF₃ |
| CH | OCH₃ | OCHF₂ | 2-OCF₃ | N | OCH₃ | OCHF₂ | 2-OCF₃ |
| CH | OCH₃ | SCHF₂ | 2-CF₃ | N | OCH₃ | SCHF₂ | 2-CF₃ |
| CH | OCH₃ | SCHF₂ | 2-OCF₃ | N | OCH₃ | SCHF₂ | 2-OCF₃ |
| CH | OCH₃ | OCF₃ | 2-CF₃ | N | OCH₃ | OCF₃ | 2-CF₃ |
| CH | OCH₃ | OCF₃ | 2-OCF₃ | N | OCH₃ | OCF₃ | 2-OCF₃ |

TABLE 3-continued

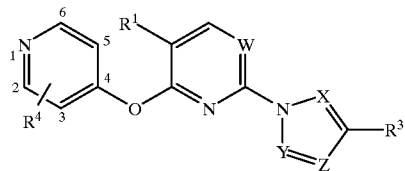

| W | R$^1$ | R$^3$ | R$^4$ | W | R$^1$ | R$^3$ | R$^4$ |
|---|---|---|---|---|---|---|---|
| CH | OCH$_3$ | SCF$_3$ | 2-CF$_3$ | N | OCH$_3$ | SCF$_3$ | 2-CF$_3$ |
| CH | OCH$_3$ | SCF$_3$ | 2-OCF$_3$ | N | OCH$_3$ | SCF$_3$ | 2-OCF$_3$ |
| CH | OCH$_3$ | Cl | 2-CF$_3$ | N | OCH$_3$ | Cl | 2-CF$_3$ |
| CH | OCH$_3$ | Cl | 2-OCF$_3$ | N | OCH$_3$ | Cl | 2-OCF$_3$ |

TABLE 4

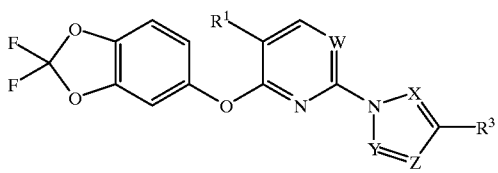

| W | R$^1$ | R$^3$ | W | R$^1$ | R$^3$ |
|---|---|---|---|---|---|
| *wherein X is N and Y and Z are CH* | | | | | |
| CH | H | CF$_3$ | N | CH$_2$CH$_3$ | CF$_3$ |
| CH | H | OCHF$_2$ | N | CH$_2$CH$_3$ | OCHF$_2$ |
| CH | H | SCHF$_2$ | N | CH$_2$CH$_3$ | SCHF$_2$ |
| CH | H | OCF$_3$ | N | CH$_2$CH$_3$ | OCF$_3$ |
| CH | H | SCF$_3$ | N | CH$_2$CH$_3$ | SCF$_3$ |
| CH | H | Cl | N | CH$_2$CH$_3$ | Cl |
| CH | CH$_3$ | CF$_3$ | N | CH$_3$ | CF$_3$ |
| CH | CH$_3$ | OCHF$_2$ | N | CH$_3$ | OCHF$_2$ |
| CH | CH$_3$ | SCHF$_2$ | N | CH$_3$ | SCHF$_2$ |
| CH | CH$_3$ | OCF$_3$ | N | CH$_3$ | OCF$_3$ |
| CH | CH$_3$ | SCF$_3$ | N | CH$_3$ | SCF$_3$ |
| CH | CH$_3$ | Cl | N | CH$_3$ | Cl |
| CH | OCH$_3$ | CF$_3$ | N | OCH$_3$ | CF$_3$ |
| CH | OCH$_3$ | OCHF$_2$ | N | OCH$_3$ | OCHF$_2$ |
| CH | OCH$_3$ | SCHF$_2$ | N | OCH$_3$ | SCHF$_2$ |
| CH | OCH$_3$ | OCF$_3$ | N | OCH$_3$ | OCF$_3$ |
| CH | OCH$_3$ | SCF$_3$ | N | OCH$_3$ | SCF$_3$ |
| CH | OCH$_3$ | Cl | N | OCH$_3$ | Cl |
| *wherein Z is N and X and Y are CH* | | | | | |
| CH | H | CF$_3$ | N | CH$_2$CH$_3$ | CF$_3$ |
| CH | H | OCHF$_2$ | N | CH$_2$CH$_3$ | OCHF$_2$ |
| CH | H | SCHF$_2$ | N | CH$_2$CH$_3$ | SCHF$_2$ |
| CH | H | OCF$_3$ | N | CH$_2$CH$_3$ | OCF$_3$ |
| CH | H | SCF$_3$ | N | CH$_2$CH$_3$ | SCF$_3$ |
| CH | H | Cl | N | CH$_2$CH$_3$ | Cl |
| CH | CH$_3$ | CF$_3$ | N | CH$_3$ | CF$_3$ |
| CH | CH$_3$ | OCHF$_2$ | N | CH$_3$ | OCHF$_2$ |
| CH | CH$_3$ | SCHF$_2$ | N | CH$_3$ | SCHF$_2$ |
| CH | CH$_3$ | OCF$_3$ | N | CH$_3$ | OCF$_3$ |
| CH | CH$_3$ | SCF$_3$ | N | CH$_3$ | SCF$_3$ |
| CH | CH$_3$ | Cl | N | CH$_3$ | Cl |
| CH | OCH$_3$ | CF$_3$ | N | OCH$_3$ | CF$_3$ |
| CH | OCH$_3$ | OCHF$_2$ | N | OCH$_3$ | OCHF$_2$ |
| CH | OCH$_3$ | SCHF$_2$ | N | OCH$_3$ | SCHF$_2$ |
| CH | OCH$_3$ | OCF$_3$ | N | OCH$_3$ | OCF$_3$ |
| CH | OCH$_3$ | SCF$_3$ | N | OCH$_3$ | SCF$_3$ |
| CH | OCH$_3$ | Cl | N | OCH$_3$ | Cl |

TABLE 5

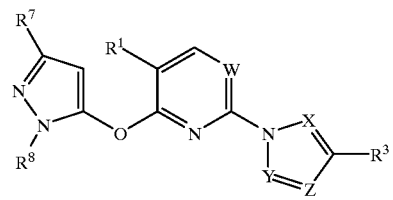

| W | R$^1$ | R$^3$ | R$^7$ | R$^8$ |
|---|---|---|---|---|
| *wherein X is N and Y and Z are CH* | | | | |
| CH | H | CF$_3$ | CF$_3$ | CH$_3$ |
| CH | H | CF$_3$ | CF$_3$ | CH$_2$CF$_3$ |
| CH | H | OCHF$_2$ | CF$_3$ | CH$_3$ |
| CH | H | OCHF$_2$ | CF$_3$ | CH$_2$CF$_3$ |
| CH | H | SCHF$_2$ | CF$_3$ | CH$_3$ |
| CH | H | SCHF$_2$ | CF$_3$ | CH$_2$CF$_3$ |
| CH | CH$_3$ | CF$_3$ | CF$_3$ | CH$_3$ |
| CH | CH$_3$ | CF$_3$ | CF$_3$ | CH$_2$CF$_3$ |
| CH | CH$_3$ | OCHF$_2$ | CF$_3$ | CH$_3$ |
| CH | CH$_3$ | OCHF$_2$ | CF$_3$ | CH$_2$CF$_3$ |
| CH | CH$_3$ | SCHF$_2$ | CF$_3$ | CH$_3$ |
| CH | CH$_3$ | SCHF$_2$ | CF$_3$ | CH$_2$CF$_3$ |
| CH | OCH$_3$ | CF$_3$ | CF$_3$ | CH$_3$ |
| CH | OCH$_3$ | CF$_3$ | CF$_3$ | CH$_2$CF$_3$ |
| CH | OCH$_3$ | OCHF$_2$ | CF$_3$ | CH$_3$ |
| CH | OCH$_3$ | OCHF$_2$ | CF$_3$ | CH$_2$CF$_3$ |
| CH | OCH$_3$ | SCHF$_2$ | CF$_3$ | CH$_3$ |
| CH | OCH$_3$ | SCHF$_2$ | CF$_3$ | CH$_2$CF$_3$ |
| N | CH$_2$CH$_3$ | CF$_3$ | CF$_3$ | CH$_3$ |
| N | CH$_2$CH$_3$ | CF$_3$ | CF$_3$ | CH$_2$CF$_3$ |
| N | CH$_2$CH$_3$ | OCHF$_2$ | CF$_3$ | CH$_3$ |
| N | CH$_2$CH$_3$ | OCHF$_2$ | CF$_3$ | CH$_2$CF$_3$ |
| N | CH$_2$CH$_3$ | SCHF$_2$ | CF$_3$ | CH$_3$ |
| N | CH$_2$CH$_3$ | SCHF$_2$ | CF$_3$ | CH$_2$CF$_3$ |
| N | CH$_3$ | CF$_3$ | CF$_3$ | CH$_3$ |
| N | CH$_3$ | CF$_3$ | CF$_3$ | CH$_2$CF$_3$ |
| N | CH$_3$ | OCHF$_2$ | CF$_3$ | CH$_3$ |
| N | CH$_3$ | OCHF$_2$ | CF$_3$ | CH$_2$CF$_3$ |
| N | CH$_3$ | SCHF$_2$ | CF$_3$ | CH$_3$ |
| N | CH$_3$ | SCHF$_2$ | CF$_3$ | CH$_2$CF$_3$ |
| N | OCH$_3$ | CF$_3$ | CF$_3$ | CH$_3$ |
| N | OCH$_3$ | CF$_3$ | CF$_3$ | CH$_2$CF$_3$ |
| N | OCH$_3$ | OCHF$_2$ | CF$_3$ | CH$_3$ |
| N | OCH$_3$ | OCHF$_2$ | CF$_3$ | CH$_2$CF$_3$ |
| N | OCH$_3$ | SCHF$_2$ | CF$_3$ | CH$_3$ |
| N | OCH$_3$ | SCHF$_2$ | CF$_3$ | CH$_2$CF$_3$ |
| CH | H | CF$_3$ | OCHF$_2$ | CH$_3$ |
| CH | H | CF$_3$ | OCHF$_2$ | CH$_2$CF$_3$ |
| CH | H | OCHF$_2$ | OCHF$_2$ | CH$_3$ |
| CH | H | OCHF$_2$ | OCHF$_2$ | CH$_2$CF$_3$ |
| CH | H | SCHF$_2$ | OCHF$_2$ | CH$_3$ |
| CH | H | SCHF$_2$ | OCHF$_2$ | CH$_2$CF$_3$ |
| CH | CH$_3$ | CF$_3$ | OCHF$_2$ | CH$_3$ |
| CH | CH$_3$ | CF$_3$ | OCHF$_2$ | CH$_2$CF$_3$ |
| CH | CH$_3$ | OCHF$_2$ | OCHF$_2$ | CH$_3$ |
| CH | CH$_3$ | OCHF$_2$ | OCHF$_2$ | CH$_2$CF$_3$ |
| CH | CH$_3$ | SCHF$_2$ | OCHF$_2$ | CH$_3$ |
| CH | CH$_3$ | SCHF$_2$ | OCHF$_2$ | CH$_2$CF$_3$ |
| CH | OCH$_3$ | CF$_3$ | OCHF$_2$ | CH$_3$ |
| CH | OCH$_3$ | CF$_3$ | OCHF$_2$ | CH$_2$CF$_3$ |
| CH | OCH$_3$ | OCHF$_2$ | OCHF$_2$ | CH$_3$ |
| CH | OCH$_3$ | OCHF$_2$ | OCHF$_2$ | CH$_2$CF$_3$ |
| CH | OCH$_3$ | SCHF$_2$ | OCHF$_2$ | CH$_3$ |
| CH | OCH$_3$ | SCHF$_2$ | OCF$_2$ | CH$_2$CF$_3$ |
| N | CH$_2$CH$_3$ | CF$_3$ | OCHF$_2$ | CH$_3$ |
| N | CH$_2$CH$_3$ | CF$_3$ | OCHF$_2$ | CH$_2$CF$_3$ |
| N | CH$_2$CH$_3$ | OCHF$_2$ | OCHF$_2$ | CH$_3$ |
| N | CH$_2$CH$_3$ | OCHF$_2$ | OCHF$_2$ | CH$_2$CF$_3$ |
| N | CH$_2$CH$_3$ | SCHF$_2$ | OCHF$_2$ | CH$_3$ |
| N | CH$_2$CH$_3$ | SCHF$_2$ | OCHF$_2$ | CH$_2$CF$_3$ |
| N | CH$_3$ | CF$_3$ | OCHF$_2$ | CH$_3$ |
| N | CH$_3$ | CF$_3$ | OCHF$_2$ | CH$_2$CF$_3$ |
| N | CH$_3$ | OCHF$_2$ | OCHF$_2$ | CH$_3$ |
| N | CH$_3$ | OCHF$_2$ | OCHF$_2$ | CH$_2$CF$_3$ |

TABLE 5-continued

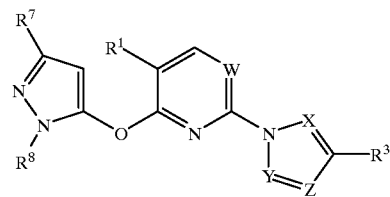

| W | R¹ | R³ | R⁷ | R⁸ |
|---|---|---|---|---|
| N | CH₃ | SCHF₂ | OCHF₂ | CH₃ |
| N | CH₃ | SCHF₂ | OCHF₂ | CH₂CF₃ |
| N | OCH₃ | CF₃ | OCHF₂ | CH₃ |
| N | OCH₃ | CF₃ | OCHF₂ | CH₂CF₃ |
| N | OCH₃ | OCHF₂ | OCHF₂ | CH₃ |
| N | OCH₃ | OCHF₂ | OCHF₂ | CH₂CF₃ |
| N | OCH₃ | SCHF₂ | OCHF₂ | CH₃ |
| N | OCH₃ | SCHF₂ | OCHF₂ | CH₂CF₃ |
| CH | H | CF₃ | SCHF₂ | CH₃ |
| CH | H | CF₃ | SCHF₂ | CH₂CF₃ |
| CH | H | OCHF₂ | SCHF₂ | CH₃ |
| CH | H | OCHF₂ | SCHF₂ | CH₂CF₃ |
| CH | H | SCHF₂ | SCHF₂ | CH₃ |
| CH | H | SCHF₂ | SCHF₂ | CH₂CF₃ |
| CH | CH₃ | CF₃ | SCHF₂ | CH₃ |
| CH | CH₃ | CF₃ | SCHF₂ | CH₂CF₃ |
| CH | CH₃ | OCHF₂ | SCHF₂ | CH₃ |
| CH | CH₃ | OCHF₂ | SCHF₂ | CH₂CF₃ |
| CH | CH₃ | SCHF₂ | SCHF₂ | CH₃ |
| CH | CH₃ | SCHF₂ | SCHF₂ | CH₂CF₃ |
| CH | OCH₃ | CF₃ | SCHF₂ | CH₃ |
| CH | OCH₃ | CF₃ | SCHF₂ | CH₂CF₃ |
| CH | OCH₃ | OCHF₂ | SCHF₂ | CH₃ |
| CH | OCH₃ | OCHF₂ | SCHF₂ | CH₂CF₃ |
| CH | OCH₃ | SCHF₂ | SCHF₂ | CH₃ |
| CH | OCH₃ | SCHF₂ | SCHF₂ | CH₂CF₃ |
| N | CH₂CH₃ | CF₃ | SCHF₂ | CH₃ |
| N | CH₂CH₃ | CF₃ | SCHF₂ | CH₂CF₃ |
| N | CH₂CH₃ | OCHF₂ | SCHF₂ | CH₃ |
| N | CH₂CH₃ | OCHF₂ | SCHF₂ | CH₂CF₃ |
| N | CH₂CH₃ | SCHF₂ | SCHF₂ | CH₃ |
| N | CH₂CH₃ | SCHF₂ | SCHF₂ | CH₂CF₃ |
| N | CH₃ | CF₃ | SCHF₂ | CH₃ |
| N | CH₃ | CF₃ | SCHF₂ | CH₂CF₃ |
| N | CH₃ | OCHF₂ | SCHF₂ | CH₃ |
| N | CH₃ | OCHF₂ | SCHF₂ | CH₂CF₃ |
| N | CH₃ | SCHF₂ | SCHF₂ | CH₃ |
| N | CH₃ | SCHF₂ | SCHF₂ | CH₂CF₃ |
| N | OCH₃ | CF₃ | SCHF₂ | CH₃ |
| N | OCH₃ | CF₃ | SCHF₂ | CH₂CF₃ |
| N | OCH₃ | OCHF₂ | SCHF₂ | CH₃ |
| N | OCH₃ | OCHF₂ | SCHF₂ | CH₂CF₃ |
| N | OCH₃ | SCHF₂ | SCHF₂ | CH₃ |
| N | OCH₃ | SCHF₂ | SCHF₂ | CH₂CF₃ | wherein Z is N and X and Y are CH

| CH | H | CF₃ | CF₃ | CH₃ |
|---|---|---|---|---|
| CH | H | CF₃ | CF₃ | CH₂CF₃ |
| CH | H | OCHF₂ | CF₃ | CH₃ |
| CH | H | OCHF₂ | CF₃ | CH₂CF₃ |
| CH | H | SCHF₂ | CF₃ | CH₃ |
| CH | H | SCHF₂ | CF₃ | CH₂CF₃ |
| CH | CH₃ | CF₃ | CF₃ | CH₃ |
| CH | CH₃ | CF₃ | CF₃ | CH₂CF₃ |
| CH | CH₃ | OCHF₂ | CF₃ | CH₃ |
| CH | CH₃ | OCHF₂ | CF₃ | CH₂CF₃ |
| CH | CH₃ | SCHF₂ | CF₃ | CH₃ |
| CH | CH₃ | SCHF₂ | CF₃ | CH₂CF₃ |
| CH | OCH₃ | CF₃ | CF₃ | CH₃ |
| CH | OCH₃ | CF₃ | CF₃ | CH₂CF₃ |
| CH | OCl13 | OCHF₂ | CF₃ | CH₃ |
| CH | OCH₃ | OCHF₂ | CF₃ | CH₂CF₃ |
| CH | OCH₃ | SCHF₂ | CF₃ | CH₃ |
| CH | OCH₃ | SCHF₂ | CF₃ | CH₂CF₃ |
| N | CH₂CH₃ | CF₃ | CF₃ | CH₃ |
| N | CH₂CH₃ | CF₃ | CF₃ | CH₂CF₃ |

TABLE 5-continued

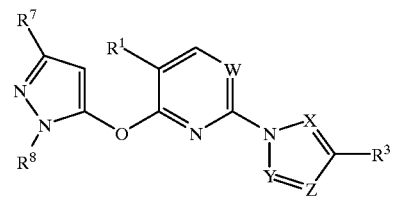

| W | R¹ | R³ | R⁷ | R⁸ |
|---|---|---|---|---|
| N | CH₂CH₃ | OCHF₂ | CF₃ | CH₃ |
| N | CH₂CH₃ | OCHF₂ | CF₃ | CH₂CF₃ |
| N | CH₂CH₃ | SCHF₂ | CF₃ | CH₃ |
| N | CH₂CH₃ | SCHF₂ | CF₃ | CH₂CF₃ |
| N | CH₃ | CF₃ | CF₃ | CH₃ |
| N | CH₃ | CF₃ | CF₃ | CH₂CF₃ |
| N | CH₃ | OCHF₂ | CF₃ | CH₃ |
| N | CH₃ | OCHF₂ | CF₃ | CH₂CF₃ |
| N | CH₃ | SCHF₂ | CF₃ | CH₃ |
| N | CH₃ | SCHF₂ | CF₃ | CH₂CF₃ |
| N | OCH₃ | CF₃ | CF₃ | CH₃ |
| N | OCH₃ | CF₃ | CF₃ | CH₂CF₃ |
| N | OCH₃ | OCHF₂ | CF₃ | CH₃ |
| N | OCH₃ | OCHF₂ | CF₃ | CH₂CF₃ |
| N | OCH₃ | SCHF₂ | CF₃ | CH₃ |
| N | OCH₃ | SCHF₂ | CF₃ | CH₂CF₃ |
| CH | H | CF₃ | OCHF₂ | CH₃ |
| CH | H | CF₃ | OCHF₂ | CH₂CF₃ |
| CH | H | OCHF₂ | OCHF₂ | CH₃ |
| CH | H | OCHF₂ | OCHF₂ | CH₂CF₃ |
| CH | H | SCHF₂ | OCHF₂ | CH₃ |
| CH | H | SCHF₂ | OCHF₂ | CH₂CF₃ |
| CH | CH₃ | CF₃ | OCHF₂ | CH₃ |
| CH | CH₃ | CF₃ | OCHF₂ | CH₂CF₃ |
| CH | CH₃ | OCHF₂ | OCHF₂ | CH₃ |
| CH | CH₃ | OCHF₂ | OCHF₂ | CH₂CF₃ |
| CH | CH₃ | SCHF₂ | OCHF₂ | CH₃ |
| CH | CH₃ | SCHF₂ | OCHF₂ | CH₂CF₃ |
| CH | OCH₃ | CF₃ | OCHF₂ | CH₃ |
| CH | OCH₃ | CF₃ | OCHF₂ | CH₂CF₃ |
| CH | OCH₃ | OCHF₂ | OCHF₂ | CH₃ |
| CH | OCH₃ | OCHF₂ | OCHF₂ | CH₂CF₃ |
| CH | OCH₃ | SCHF₂ | OCHF₂ | CH₃ |
| CH | OCH₃ | SCHF₂ | OCHF₂ | CH₂CF₃ |
| N | CH₂CH₃ | CF₃ | OCHF₂ | CH₃ |
| N | CH₂CH₃ | CF₃ | OCHF₂ | CH₂CF₃ |
| N | CH₂CH₃ | OCHF₂ | OCHF₂ | CH₃ |
| N | CH₂CH₃ | OCHF₂ | OCHF₂ | CH₂CF₃ |
| N | CH₂CH₃ | SCHF₂ | OCHF₂ | CH₃ |
| N | CH₂CH₃ | SCHF₂ | OCHF₂ | CH₂CF₃ |
| N | CH₃ | CF₃ | OCHF₂ | CH₃ |
| N | CH₃ | CF₃ | OCHF₂ | CH₂CF₃ |
| N | CH₃ | OCHF₂ | OCHF₂ | CH₃ |
| N | CH₃ | OCHF₂ | OCHF₂ | CH₂CF₃ |
| N | CH₃ | SCHF₂ | OCHF₂ | CH₃ |
| N | CH₃ | SCHF₂ | OCHF₂ | CH₂CF₃ |
| N | OCH₃ | CF₃ | OCHF₂ | CH₃ |
| N | OCH₃ | CF₃ | OCHF₂ | CH₂CF₃ |
| N | OCH₃ | OCHF₂ | OCHF₂ | CH₃ |
| N | OCH₃ | OCHF₂ | OCHF₂ | CH₂CF₃ |
| N | OCH₃ | SCHF₂ | OCHF₂ | CH₃ |
| N | OCH₃ | SCHF₂ | OCHF₂ | CH₂CF₃ |
| CH | H | CF₃ | SCHF₂ | CH₃ |
| CH | H | CF₃ | SCHF₂ | CH₂CF₃ |
| CH | H | OCHF₂ | SCHF₂ | CH₃ |
| CH | H | OCHF₂ | SCHF₂ | CH₂CF₃ |
| CH | H | SCHF₂ | SCHF₂ | CH₃ |
| CH | H | SCHF₂ | SCHF₂ | CH₂CF₃ |
| CH | CH₃ | CF₃ | SCHF₂ | CH₃ |
| CH | CH₃ | CF₃ | SCHF₂ | CH₂CF₃ |
| CH | CH₃ | OCHF₂ | SCHF₂ | CH₃ |
| CH | CH₃ | OCHF₂ | SCHF₂ | CH₂CF₃ |
| CH | CH₃ | SCHF₂ | SCHF₂ | CH₃ |
| CH | CH₃ | SCHF₂ | SCHF₂ | CH₂CF₃ |
| CH | OCH₃ | CF₃ | SCHF₂ | CH₃ |
| CH | OCH₃ | CF₃ | SCHF₂ | CH₂CF₃ |

TABLE 5-continued

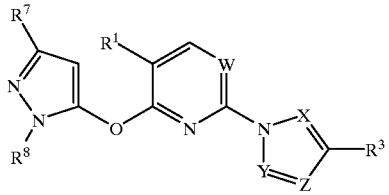

| W  | R¹      | R³      | R⁷    | R⁸       |
|----|---------|---------|-------|----------|
| CH | OCH₃    | OCHF₂   | SCHF₂ | CH₃      |
| CH | OCH₃    | OCHF₂   | SCHF₂ | CH₂CF₃   |
| CH | OCH₃    | SOHF₂   | SCHF₂ | CH₃      |
| CH | OCH₃    | SCHF₂   | SCHF₂ | CH₂CF₃   |
| N  | CH₂CH₃  | CF₃     | SCHF₂ | CH₃      |
| N  | CH₂CH₃  | CF₃     | SCHF₂ | CH₂CF₃   |
| N  | CH₂CH₃  | OCHF₂   | SCHF₂ | CH₃      |
| N  | CH₂CH₃  | OCHF₂   | SCHF₂ | CH₂CF₃   |
| N  | CH₂CH₃  | SCHF₂   | SCHF₂ | CH₃      |
| N  | CH₂CH₃  | SCHF₂   | SCHF₂ | CH₂CF₃   |
| N  | CH₃     | CF₃     | SCHF₂ | CH₃      |
| N  | CH₃     | CF₃     | SCHF₂ | CH₂CF₃   |
| N  | CH₃     | OCHF₂   | SCHF₂ | CH₃      |
| N  | CH₃     | OCHF₂   | SCHF₂ | CH₂CF₃   |
| N  | CH₃     | SCHF₂   | SCHF₂ | CH₃      |
| N  | CH₃     | SCHF₂   | SCHF₂ | CH₂CF₃   |
| N  | OCH₃    | CF₃     | SCHF₂ | CH₃      |
| N  | OCH₃    | CF₃     | SCHF₂ | CH₂CF₃   |
| N  | OCH₃    | OCHF₂   | SCHF₂ | CH₃      |
| N  | OCH₃    | OCHF₂   | SCHF₂ | CH₂CF₃   |
| N  | OCH₃    | SCHF₂   | SCHF₂ | CH₃      |
| N  | OCH₃    | SCHF₂   | SCHF₂ | CH₂CF₃   |

Formulation/Utility

Compounds of this invention will generally be used as a formulation or composition with an agriculturally suitable carrier comprising at least one of a liquid diluent, a solid diluent or a surfactant. The formulation or composition ingredients are selected to be consistent with the physical properties of the active ingredient, mode of application and environmental factors such as soil type, moisture and temperature. Useful formulations include liquids such as solutions (including emulsifiable concentrates), suspensions, emulsions (including microemulsions and/or suspoemulsions) and the like which optionally can be thickened into gels. Useful formulations further include solids such as dusts, powders, granules, pellets, tablets, films, and the like which can be water-dispersible ("wettable") or water-soluble. Active ingredient can be (micro)encapsulated and further formed into a suspension or solid formulation; alternatively the entire formulation of active ingredient can be encapsulated (or "overcoated"). Encapsulation can control or delay release of the active ingredient. Sprayable formulations can be extended in suitable media and used at spray volumes from about one to several hundred liters per hectare. High-strength compositions are primarily used as intermediates for further formulation.

The formulations will typically contain effective amounts of active ingredient, diluent and surfactant within the following approximate ranges which add up to 100 percent by weight.

|  | Weight Percent | | |
|---|---|---|---|
|  | Active Ingredient | Diluent | Surfactant |
| Water-Dispersible and Water-soluble Granules, Tablets and Powders. | 5–90 | 0–92 | 1–15 |
| Suspensions, Emulsions, Solutions (including Emulsifiable Concentrates) | 5–50 | 20–95 | 0–15 |
| Dusts | 1–25 | 70–99 | 0–5 |
| Granules and Pellets | 0.01–99 | 5–99.99 | 0–15 |
| High Strength Compositions | 90–99 | 0–10 | 0–2 |

Typical solid diluents are described in Watkins, et al., *Handbook of Insecticide Dust Diluents and Carriers*, 2nd Ed., Dorland Books, Caldwell, N.J. Typical liquid diluents are described in Marsden, *Solvents Guide,* 2nd Ed., Interscience, N.Y., 1950. *McCutcheon 's Detergents and Emulsifters Annual,* Allured Publ. Corp., Ridgewood, N.J., as well as Sisely and Wood, *Encyclopedia of Surface Active Agents,* Chemical Publ. Co., Inc., New York, 1962, list surfactants and recommended uses. All formulations can contain minor amounts of additives to reduce foam, caking, corrosion, microbiological growth and the like, or thickeners to increase viscosity.

Surfactants include, for example, polyethoxylated alcohols, polyethoxylated alkylphenols, polyethoxylated sorbitan fatty acid esters, dialkyl sulfosuccinates, alkyl sulfates, alkylbenzene sulfonates, organosilicones, N,N-dialkyltaurates, lignin sulfonates, naphthalene sulfonate formaldehyde condensates, polycarboxylates, and polyoxyethylene/polyoxypropylene block copolymers. Solid diluents include, for example, clays such as bentonite, montmorillonite, attapulgite and kaolin, starch, sugar, silica, talc, diatomaceous earth, urea, calcium carbonate, sodium carbonate and bicarbonate, and sodium sulfate. Liquid diluents include, for example, water, N,N-dimethylformamide, dimethyl sulfoxide, N-alkylpyrrolidone, ethylene glycol, polypropylene glycol, paraffins, alkylbenzenes, alkylnaphthalenes, oils of olive, castor, linseed, tung, sesame, corn, peanut, cotton-seed, soybean, rape-seed and coconut, fatty acid esters, ketones such as cyclohexanone, 2-heptanone, isophorone and 2-hydroxy-2-methyl-2-pentanone, and alcohols such as methanol, cyclohexanol, decanol and tetrahydrofurfuryl alcohol.

Solutions, including emulsifiable concentrates, can be prepared by simply mixing the ingredients. Dusts and powders can be prepared by blending and, usually, grinding as in a hammer mill or fluid-energy mill. Suspensions are usually prepared by wet-milling; see, for example, U.S. Pat. No. 3,060,082. Granules and pellets can be prepared by spraying the active material upon preformed granular carriers or by agglomeration techniques. See Browning, "Agglomeration", *Chemical Engineering,* Dec. 2, 1967, pp 127–28, *Perry 's Chemical Engineer's Handbook,* 2nd Ed., McGraw-Hill, N.Y., 1963, pages 8–57 and following, and WO 91/13526. Pellets can be prepared as described in U.S. Pat. No. 2,172,712. Water-dispersible and water-soluble granules can be prepared as taught in U.S. Pat. No. 2,122,050, U.S. Pat. No. 3,920,222 and DE 3,226,293. Tablets can be prepared as taught in U.S. Pat. No. 5,180,587, U.S. Pat. No. 5,232,701 and U.S. Pat. No. 5,208,030. Films can be prepared as taught in GB 2,095,558 and U.S. Pat. No. 3,299,566.

For further information regarding the art of formulation, see U.S. Pat. No. 3,235,361, Col. 6, line 16 through Col. 7, line 19 and Examples 10–21; U.S. Pat. No. 3,309,192, Col. 5, line 23 through Col. 7, line 62 and Examples 8, 12, 15, 39, 21, 52, 53, 58, 132, 138–120, 162–162, 166, 167 and 169–182; U.S. Pat. No. 2,891,855, Col. 3, line 66 through Col. 5, line 17 and Examples 1–2; Klingman, Weed Control as a Science, John Wiley and Sons, Inc., New York, 1961, pp 81–96; and Hance et al., *Weed Control Handbook,* 5th Ed., Blackwell Scientific Publications, Oxford, 1989.

In the following Examples, all percentages are by weight and all formulations are prepared in conventional ways. Compound numbers refer to compounds in Index Tables A–D.

Example A

High Strength Concentrate

| | |
|---|---|
| Compound 20 | 98.5% |
| silica aerogel | 0.5% |
| synthetic amorphous fine silica | 1.0%. |

Example B

Wettable Powder

| | |
|---|---|
| Compound 49 | 65.0% |
| dodecylphenol polyethylene glycol ether | 2.0% |
| sodium ligninsulfonate | 2.0% |
| sodium silicoaluminate | 6.0% |
| montmorillionite (calcined) | 23.0%. |

Example C

Granule

| | |
|---|---|
| Compound 12 | 10.0% |
| attapulgite granules (low volatile matter, 0.71/0.30 mm; U.S.S. No. 25–50 sieves) | 90.0%. |

Example D

Extruded Pellet

| | |
|---|---|
| Compound 56 | 25.0% |
| anhydrous sodium sulfate | 10.0% |
| crude calcium ligninsulfonate | 5.0% |
| sodium alkylnaphthalenesulfonate | 1.0% |
| calcium/magnesium bentonite | 59.0%. |

Test results indicate that the compounds of the present invention are highly active preemergent and postemergent herbicides or plant growth regulants. Many of them have utility for broad-spectrum pre- and/or postemergence weed control in areas where complete control of all vegetation is desired such as around fuel storage tanks, industrial storage areas, parking lots, drive-in theaters, air fields, river banks, irrigation and other waterways, around billboards and highway and railroad structures. Some of the compounds are useful for the control of selected grass and broadleaf weeds with tolerance to important agronomic crops which include but are not limited to alfalfa, barley, cotton, wheat, rape, sugar beets, corn (maize), sorghum, soybeans, rice, oats, peanuts, vegetables, tomato, potato, perennial plantation crops including coffee, cocoa, oil palm, rubber, sugarcane, citrus, grapes, fruit trees, nut trees, banana, plantain, pineapple, hops, tea and forests such as eucalyptus and conifers (e.g., loblolly pine), and turf species (e.g., Kentucky bluegrass, St. Augustine grass, Kentucky fescue and Bermuda grass). Those skilled in the art will appreciate that not all compounds are equally effective against all weeds. Alternatively, the subject compounds are useful to modify plant growth.

A herbicidally effective amount of the compounds of this invention is determined by a number of factors. These factors include: formulation selected, method of application, amount and type of vegetation present, growing conditions, etc. In general, a herbicidally effective amount of compounds of this invention is 0.001 to 20 kg/ha with a preferred range of 0.002 to 1.0 kg/ha. One skilled in the art can easily determine the herbicidally effective amount necessary for the desired level of weed control.

Compounds of this invention can be used alone or in combination with other commercial herbicides, insecticides or fungicides. Compounds of this invention can also be used in combination with commercial herbicide safeners such as benoxacor, dichlormid and furilazole to increase safety to certain crops. A mixture of one or more of the following herbicides with a compound of this invention may be particularly useful for weed control: acetochlor, acifluorfen and its sodium salt, aclonifen, acrolein (2-propenal), alachlor, ametryn, amidosulfuron, amitrole, ammonium sulfamate, anilofos, asulam, atrazine, azafenidin, azimsulfuron, benazolin, benazolin-ethyl, benfluralin, benfuresate, bensulfuron-methyl, bensulide, bentazone, bifenox, bispyribac and its sodium salt, bromacil, bromoxynil, bromoxynil octanoate, butachlor, butralin, butroxydim (ICIA0500), butylate, caloxydim (BAS 620H), carfentrazone-ethyl, chlomethoxyfen, chloramben, chlorbromuron, chloridazon, chlorimuron-ethyl, chlornitrofen, chlorotoluron, chlorpropham, chlorsulfuron, chlorthal-dimethyl, cinmethylin, cinosulfuron, clethodim, clomazone, clopyralid, clopyralid-olamine, cyanazine, cycloate, cyclosulfamuron, 2,2-D and its butotyl, butyl, isoctyl and isopropyl esters and its dimethylammonium, diolamine and trolamine salts, daimuron, dalapon, dalapon-sodium, dazomet, 2,2-DB and its dimethylammonium, potassium and sodium salts, desmedipham, desmetryn, dicamba and its diglycolammonium, dimethylammonium, potassium and sodium salts, diclilobenil, dichlorprop, diclofop-methyl, 2-[2,5-dihydro-2-methyl-2-(1-methylethyl)-5-oxo-1H-imidazol-2-yl]-5-methyl-3-pyridinecarboxylic acid (AC 263,222), difenzoquat metilsulfate, diflufenican, dimepiperate, dimethenamid, dimethylarsinic acid and its sodium salt, dinitramine, diphenamid, diquat dibromide, dithiopyr, diuron, DNOC, endothal, EPTC. esprocarb, ethalfluralin, ethametsulfuron-methyl, ethofumesate, ethoxysulfuron, fenoxaprop-ethyl, fenoxaprop-P-ethyl, fenuron, fenuron-TCA, flamprop-methyl, flamprop-M-isopropyl, flamprop-M-methyl, flazasulfuron, fluazifop-butyl, fluazifop-P-butyl, fluchloralin, flumetsulam, flumiclorac-pentyl, flumioxazin, fluometuron, fluoroglycofen-ethyl, flupoxam, flupyrsulfuron-methyl and its sodium salt, fluridone, flurochloridone, fluroxypyr, fluthiacet-methyl, fomesafen, fosamine-ammonium, glufosinate, glufosinate-ammonium, glyphosate, glyphosate-isopropylammonium, glyphosate-sesquisodium, glyphosate-trimesium, halosulfuron-methyl, haloxyfop-etotyl, haloxyfop-methyl, hexazinone, imazamethabenz-methyl, imazamox, imazapyr, imazaquin, imazaquin-ammonium, imazethapyr, imazethapyr-ammonium, imazosulfuron, ioxynil, ioxynil octanoate, ioxynil-sodium, isoproturon, isouron, isoxaben, isoxaflutole, lactofen, lenacil, linuron, maleic hydrazide, MCPA and its dimethylammonium, potassium and sodium salts, MCPA-isoctyl, mecoprop, mecoprop-P, mefenacet, mefluidide, metam-sodium, methabenzthiazuron, methylarsonic acid and its calcium, monoammonium, monosodium and disodium salts, methyl [[[1-[5-[2-chloro-2-(trifluoromethyl) phenoxy]-2-nitrophenyl]-2-methoxyethylidene]amino]oxy] acetate (AKH-7088), methyl 5-[[[[(2,6-dimethyl-2-pyrimidinyl)amino]carbonyl]amino]sulfonyl]-1-(2-pyridinyl)-1H-pyrazole-2-carboxylate (NC-330), metobenzuron, metolachlor, metosulam, metoxuron, metribuzin, metsulfuron-methyl, molinate, monolinuron, napropamide, naptalam, neburon, nicosulfuron, norflurazon, oryzalin, oxadiazon, oxasulfuron, oxyfluorfen, paraquat dichloride, pebulate, pendimethalin, pentoxazone (KPP-312), perfluidone, phenmedipham, picloram, picloram-potassium, pretilachlor, primisulfuron-methyl, prometon, prometryn, propachlor, propanil, propaquizafop, propazine, propham, propyzamide, prosulfuron, pyrazolynate, pyrazosulfuron-ethyl, pyridate, pyriminobac-methyl, pyrithiobac, pyrithiobac-sodium, quinclorac, quizalofop-ethyl, quizalofop-P-ethyl, quizalofop-P-tefuryl, rimsulfuron, sethoxydim, siduron, simazine, sulcotrione (ICIA005 1), sulfentrazone, sulfometuron-methyl, TCA, TCA-sodium, tebuthiuron, terbacil, terbuthylazine, terbutryn, thenylchlor, thiafluamide (BAY 11390), thifensulfuron-methyl, thiobencarb, tralkoxydim, tri-allate, triasulfuron, triaziflam, tribenuron-methyl, triclopyr, triclopyr-butotyl, triclopyr-triethylammnonium, tridiphane, trifluralin, triflusulfuron-methyl, and vernolate.

In certain instances, combinations with other herbicides having a similar spectrum of control but a different mode of action will be particularly advantageous for preventing the development of resistant weeds.

The following Tests demonstrate the control efficacy of the compounds of this invention against specific weeds. The weed control afforded by the compounds is not limited, however, to these species. See Index Tables A–E for compound descriptions. The abbreviation "Ex." stands for "Example" and is followed by a number indicating in which example the compound is prepared.

INDEX TABLE A

| Cmpd | W | $R^1$ | $R^2$ | X | Y | Z | $R^3$ | mp (° C.) |
|---|---|---|---|---|---|---|---|---|
| 1 (Ex. 1) | CH | H | H | N | CH | CH | $CF_3$ | 53–55 |
| 2 | CH | H | H | CCl | CH | N | Cl | oil* |
| 3 | CH | H | H | N | CH | CBr | H | 63–65 |
| 4 | CH | H | H | N | CH | N | Cl | 83–86 |
| 5 | CH | H | H | CH | CH | N | $CF_3$ | 78–79 |
| 6 (Ex. 2) | N | H | H | N | CH | CH | $CF_3$ | 72–73 |
| 7 | N | H | H | CCl | CH | N | Cl | 80–89 |
| 8 | N | H | H | N | $CCH_3$ | CH | $CF_3$ | 110–112 |
| 9 | N | H | H | N | CH | CBr | H | oil* |
| 10 | N | H | H | N | CH | N | Cl | 83–86 |
| 11 | N | H | $CH_3$ | N | CH | CH | $CF_3$ | 93–95 |
| 12 (Ex. 3) | N | $CH_3$ | H | N | CH | CH | $CF_3$ | 113–115 |
| 13 | N | $CH_3$ | H | CH | CH | N | $CF_3$ | 63–66 |
| 14 | N | $CH_3$ | H | N | CH | CCl | $CF_3$ | 108–109 |
| 15 | N | $CH_3$ | $CH_3$ | N | CH | CH | $CF_3$ | 107–108 |
| 16 | N | $CH_3$ | H | N | CH | N | $CF_3$ | 114–115 |
| 17 | N | $CH_3$ | H | N | CH | CCN | $CF_3$ | 141–142 |
| 18 | N | $CH_2CH_3$ | H | N | CH | N | $CF_3$ | 97–98 |

*See Index Table E for $^1$H NMR data.

INDEX TABLE C

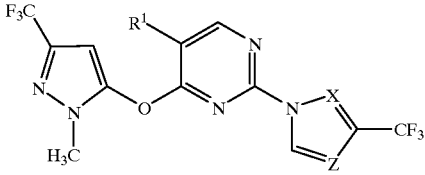

| Cmpd | R¹ | X | Z | mp (° C.) |
|---|---|---|---|---|
| 49 | CH₃ | N | CH | 173–174 |
| 50 | CH₃ | CH | N | 145–146 |
| 51 | CH₃ | N | CCl | 178–179 |
| 52 | CH₂CH₃ | N | CH | 146–147 |
| 53 | OCH₃ | N | CH | 178–180 |
| 54 | CH₂CH₃ | N | CCN | 103–108 |
| 55 | CH₃ | N | N | 150–151 |

INDEX TABLE D

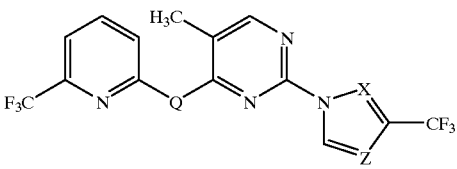

| Cmpd | X | Z | mp (° C.) |
|---|---|---|---|
| 56 | N | CH | 170–172 |
| 57 | N | CCl | 150–153 |
| 58 | N | N | 149–150 |

INDEX TABLE E

| Cmpd No. | $^1$H NMR Data (CDCl₃ solution unless indicated otherwise)[a] |
|---|---|
| 2 | δ 7.06(d, 1H), 7.31(d, 1H), 7.35–7.60(m, 2H), 7.72(s, 1H), 7.93(dd, 1H). |
| 9 | δ 6.85(d, 1H), 7.20–7.27(m, 1H), 7.50(s, 1H), 7.58–7.65(m, 2H), 7.75(s, 1H), 8.18(s, 1H), 8.65(d, 1H). |
| 20 | δ 8.38(s, 1H), 8.28(s, 1H), 7.89(s, 1H), 7.49(t, 1H), 7.25–7.10(m, 3H), 2.37(s, 3H). |
| 35 | δ 8.41(s, 1H), 8.30(s, 1H), 7.90(s, 1H), 7.51(t, 1H), 7.23(d, 1H), 7.18–7.10(m, 2H), 2.80(q, 2H), 1.37(t, 3H). |

[a]$^1$H NMR data are in ppm downfield from tetramethylsilane. Couplings are designated by (s)-singlet, (d)-doublet, (t)-triplet, (q)-quartet, (m)-multiplet, (dd)-doublet of doublets, (dt)-doublet of triplets, (br s)-broad singlet.

BIOLOGICAL EXAMPLES OF THE INVENTION

Test A

Seeds of broadleaf signalgrass (*Brachiaria decumbens*), barley (*Hordeum vulgare*), barnyardgrass (*Echinochloa crus-galli*), bedstraw (*Galium aparine*), blackgrass (*Alopecurus myosuroides*), chickweed (*Stellaria media*), cocklebur (*Xanthium strumarium*), corn (*Zea mays*), cotton (*Gossypium hirsutum*), crabgrass (*Digitaria sanguinalis*), downy brome (*Bromus tectorum*), giant foxtail (*Setaria faberii*), lambsquarters (*Chenopodium album*), morningglory (*Ipomoea hederacea*), rape (*Brassica napus*), redroot pigweed (*Amaranthus retroflexus*), rice (*Oryza sativa*), sorghum (*Sorghum bicolor*), soybean (*Glycine max*), sugar beet (*Beta vulgaris*), velvetleaf (*Abutilon theophrasti*), wheat (*Triticum aestivum*), wild buckwheat (*Polygonum convolvulus*), wild oat (*Avena fatua*) and purple nutsedge (*Cyperus rotundus*) tubers were planted and treated preemergence with test chemicals formulated in a non-phytotoxic solvent mixture which included a surfactant. A sprayed paddy pot was treated with some designated compounds. This paddy contained rice, barnyardgrass, smallflowered flatsedge (*Cyperus difformis*) and duck salad (*Heteranthera limosa*) as the target species and was sprayed alongside the other crop and weed species.

At the same time, these crop and weed species were also treated with postemergence, applications of test chemicals formulated in the same manner. Plants ranged in height from 2 to 18 cm (1- to 4-leaf stage) for postemergence treatments. Treated plants and controls were maintained in a greenhouse for twelve to sixteen days, after which all species were compared to controls and visually evaluated. Plant response ratings, summarized in Table A, arc bcased on a scale of 0 to 10 where 0 is no effect and 10 is complete control. A dash (-) response means no test result.

TABLE A

| | COMPOUND | | | | | | | | | COMPOUND | | | |
|---|---|---|---|---|---|---|---|---|---|---|---|---|---|
| Rate 2000 g/ha POSTEMERGENCE | 1 | 2 | 3 | 4 | 5 | 6 | 7 | 11 | Rate 1000 g/ha POSTEMERGENCE | 13 | 14 | 19 | 49 |
| B. signalgrass | — | — | — | — | — | — | — | — | B. signalgrass | 10 | 8 | 7 | 8 |
| Barley | 6 | 3 | 2 | 5 | 5 | 5 | 4 | 2 | Barley | — | — | — | — |
| Barnyardgrass | 4 | 3 | 6 | 7 | 9 | 8 | 4 | 3 | Barnyardgrass | — | — | — | — |
| Bedstraw | 9 | 9 | 10 | 10 | 9 | 9 | 9 | 3 | Bedstraw | 9 | 10 | 9 | 9 |
| Blackgrass | 8 | 4 | 3 | 5 | 8 | 9 | 3 | 3 | Blackgrass | 8 | 9 | 6 | 8 |
| Chickweed | 7 | 6 | 6 | 9 | 9 | 9 | 6 | 5 | Chickweed | — | — | — | — |
| Cocklebur | 7 | 6 | 4 | 7 | 8 | 8 | 8 | 6 | Cocklebur | 9 | 10 | 8 | 9 |
| Corn | 3 | 2 | 2 | 3 | 3 | 3 | 2 | 3 | Corn | 6 | 4 | 7 | 8 |
| Cotton | 8 | 6 | 10 | 8 | 10 | 9 | 9 | 8 | Cotton | — | — | — | — |
| Crabgrass | 8 | 4 | 8 | 9 | 9 | 9 | 6 | 8 | Crabgrass | 9 | 10 | 9 | 9 |
| Downy brome | 3 | 3 | 2 | 3 | 6 | 5 | 3 | 2 | Downy brome | — | — | — | — |
| Giant foxtail | 4 | 3 | 4 | 9 | 9 | 9 | 4 | 6 | Giant foxtail | 9 | 10 | 9 | 9 |

TABLE A-continued

| | | | | | | | | | | | | | |
|---|---|---|---|---|---|---|---|---|---|---|---|---|---|
| Lambsquarters | 9 | 8 | 9 | 9 | 9 | 9 | 7 | 9 | Lambsquarters | — | — | — | — |
| Morningglory | 9 | 4 | 9 | 7 | 9 | 9 | 9 | 8 | Morningglory | 10 | 10 | 8 | 9 |
| Nutsedge | 2 | — | 0 | — | 2 | 2 | 0 | 0 | Nutsedge | 2 | 3 | 0 | 3 |
| Rape | 8 | 7 | 9 | 10 | 10 | 10 | 9 | 9 | Rape | 10 | 10 | 9 | 10 |
| Redroot pigweed | — | — | — | — | — | — | — | — | Redroot pigweed | 9 | 10 | 9 | 9 |
| Rice | 3 | 2 | 3 | 3 | 4 | 3 | 1 | 3 | Rice | — | — | — | — |
| Sorghum | 4 | 2 | 3 | 3 | 4 | 4 | 2 | 2 | Sorghum | — | — | — | — |
| Soybean | 9 | 3 | 5 | 6 | 8 | 9 | 8 | 8 | Soybean | 10 | 10 | 8 | 10 |
| Sugar beet | 9 | 8 | 10 | 10 | 10 | 10 | 9 | 9 | Sugar beet | 9 | 10 | 9 | 9 |
| Velvetleaf | 7 | 7 | 7 | 7 | 9 | 9 | 7 | 1 | Velvetleaf | 9 | 9 | 7 | 9 |
| Wheat | 0 | 2 | 2 | 3 | 4 | 3 | 2 | 1 | Wheat | 5 | 4 | 3 | 3 |
| Wild buckwheat | 7 | 8 | 5 | 9 | 8 | 9 | 10 | 6 | Wild buckwheat | — | — | — | — |
| Wild oat | 4 | 3 | 4 | 4 | 5 | 5 | 4 | 3 | Wild oat | 7 | 9 | 8 | 8 |

| | COMPOUND | | | | | | | | COMPOUND | | | |
|---|---|---|---|---|---|---|---|---|---|---|---|---|
| Rate 2000 g/ha PREEMERGENCE | 1 | 2 | 3 | 4 | 5 | 6 | 7 | 11 | Rate 1000 g/ha PREEMERGENCE | 13 | 14 | 19 | 49 |
| B. signalgrass | — | — | — | — | — | — | — | — | B. signalgrass | 10 | 10 | 10 | 10 |
| Barley | 6 | 0 | 0 | 2 | 5 | 8 | 1 | 2 | Barley | — | — | — | — |
| Barnyardgrass | 9 | 0 | 9 | 9 | 9 | 10 | 3 | 9 | Barnyardgrass | — | — | — | — |
| Bedstraw | 8 | 1 | 8 | 4 | 10 | 8 | 3 | 8 | Bedstraw | 10 | 10 | 9 | 10 |
| Blackgrass | 10 | 0 | 8 | 10 | 9 | 10 | 4 | 10 | Blackgrass | 10 | 10 | 9 | 10 |
| Chickweed | 9 | 4 | 5 | 8 | 10 | 10 | 2 | 9 | Chickweed | — | — | — | — |
| Cocklebur | 0 | 0 | 0 | 0 | 3 | 2 | 0 | 0 | Cocklebur | 8 | 7 | 2 | 6 |
| Corn | 2 | 0 | 0 | 1 | 2 | 3 | 0 | 1 | Corn | 5 | 4 | 7 | 7 |
| Cotton | 3 | 2 | 2 | 1 | 7 | 4 | 0 | 0 | Cotton | — | — | — | — |
| Crabgrass | 10 | 1 | 9 | 10 | 10 | 10 | 9 | 10 | Crabgrass | 10 | 10 | 10 | 10 |
| Downy brome | 10 | 0 | 2 | 7 | 9 | 10 | 2 | 5 | Downy brome | — | — | — | — |
| Giant foxtail | 10 | 2 | 9 | 10 | 10 | 10 | 9 | 10 | Giant foxtail | 10 | 10 | 10 | 10 |
| Lambsquarters | 9 | 9 | 9 | 9 | 10 | 10 | 8 | 10 | Lambsquarters | — | — | — | — |
| Morningglory | 3 | 1 | 2 | 4 | 8 | 10 | 3 | 3 | Morningglory | 10 | 10 | 10 | 10 |
| Nutsedge | — | 0 | 0 | 0 | 0 | — | — | — | Nutsedge | 0 | 1 | 0 | 1 |
| Rape | 8 | 2 | 2 | 4 | 9 | 10 | 6 | 7 | Rape | 10 | 10 | 10 | 10 |
| Redroot pigweed | — | — | — | — | — | — | — | — | Redroot pigweed | 10 | 10 | 10 | 10 |
| Rice | 2 | 0 | 0 | 0 | 2 | 1 | 0 | 0 | Rice | — | — | — | — |
| Sorghum | 7 | 0 | 0 | 2 | 1 | 4 | 0 | 4 | Sorghum | — | — | — | — |
| Soybean | 1 | 0 | 0 | 0 | 2 | 4 | 0 | 1 | Soybean | 6 | 5 | 3 | 7 |
| Sugar beet | 10 | 0 | 3 | 9 | 10 | 10 | 6 | 10 | Sugar beet | 10 | 10 | 10 | 10 |
| Velvetleaf | 2 | 0 | 0 | 1 | 10 | 10 | 2 | 2 | Velvetleaf | 10 | 10 | 10 | 10 |
| Wheat | 9 | 0 | 0 | 2 | 7 | 9 | 0 | 1 | Wheat | 7 | 9 | 2 | 7 |
| Wild buckwheat | 5 | 1 | 1 | 6 | 9 | 10 | 2 | 8 | Wild buckwheat | — | — | — | — |
| Wild oat | 10 | 3 | 7 | 9 | 9 | 10 | 5 | 10 | Wild oat | 10 | 10 | 10 | 10 |

| | COMPOUND | | | | | | | | | |
|---|---|---|---|---|---|---|---|---|---|---|
| Rate 400 g/ha POSTEMERGENCE | 1 | 2 | 3 | 4 | 5 | 6 | 7 | 8 | 10 | 11 |
| B. signalgrass | — | — | — | — | — | — | — | — | — | — |
| Barley | 3 | 2 | 2 | 3 | 3 | 3 | 3 | 0 | 3 | 2 |
| Barnyardgrass | 2 | 2 | 2 | 2 | 7 | 3 | 2 | 0 | 0 | 2 |
| Bedstraw | 9 | 7 | 8 | 7 | 7 | 8 | 9 | 1 | 7 | 2 |
| Blackgrass | 3 | 3 | 2 | 3 | 4 | 3 | 2 | 0 | 3 | 1 |
| Chickweed | 5 | 5 | 2 | 4 | 7 | 8 | 5 | 0 | 4 | 3 |
| Cocklebur | 6 | 5 | 4 | 6 | 7 | 5 | 5 | 0 | 5 | 4 |
| Corn | 2 | 1 | 2 | 2 | 2 | 2 | 0 | 0 | 1 | 2 |
| Cotton | — | 6 | 7 | 8 | 9 | 9 | 9 | 0 | 3 | 8 |
| Crabgrass | 5 | 3 | 4 | 7 | 7 | 9 | 3 | 0 | 2 | 6 |
| Downybrome | 1 | 3 | 1 | 2 | 3 | 3 | 2 | 0 | 2 | 0 |
| Giant foxtail | 2 | 3 | 2 | 3 | 6 | 6 | 2 | 0 | 1 | 3 |
| Lambsquarters | 8 | 8 | 6 | 9 | 9 | 9 | 7 | 0 | 3 | 9 |
| Morningglory | 8 | 4 | 8 | 7 | 8 | 9 | 7 | 1 | 2 | 7 |
| Nutsedge | 1 | 0 | 0 | 0 | 0 | 2 | 0 | 0 | 0 | 0 |
| Rape | 6 | 7 | 6 | 8 | 7 | 10 | 8 | 1 | 6 | 8 |
| Redroot pigweed | — | — | — | — | — | — | — | — | — | — |
| Rice | 2 | 2 | 2 | 2 | 2 | 2 | 1 | 0 | 1 | 2 |
| Sorghum | 3 | 1 | 0 | 1 | 2 | 3 | 2 | 0 | 0 | 2 |
| Soybean | 6 | 3 | 3 | 5 | 7 | 9 | 4 | 2 | 2 | 6 |
| Sugar beet | 9 | 8 | 9 | 9 | 9 | 9 | 8 | 1 | 7 | 9 |
| Velvetleaf | 2 | 6 | 5 | 1 | 8 | 8 | 2 | 0 | 2 | 1 |
| Wheat | 0 | 2 | 1 | 3 | 2 | 1 | 2 | 0 | 1 | 0 |
| Wild buckwheat | 7 | 7 | 2 | 9 | 4 | 8 | 7 | 1 | 0 | 3 |
| Wild oat | 3 | 2 | 1 | 2 | 3 | 4 | 2 | 0 | 2 | 2 |

| | COMPOUND | | | | | | | | | |
|---|---|---|---|---|---|---|---|---|---|---|
| Rate 400 g/ha | 1 | 2 | 3 | 4 | 5 | 6 | 7 | 8 | 10 | 11 |

TABLE A-continued

PREEMERGENCE

| | | | | | | | | | | |
|---|---|---|---|---|---|---|---|---|---|---|
| B. signalgrass | — | — | — | — | — | — | — | — | — | — |
| Barley | 1 | 0 | 0 | 0 | 2 | 4 | 0 | 0 | 0 | 0 |
| Barnyardgrass | 3 | 0 | 0 | 0 | 5 | 5 | 0 | 2 | 1 | 4 |
| Bedstraw | 3 | 0 | 0 | — | 6 | 8 | 0 | 0 | 0 | 0 |
| Blackgrass | 9 | 0 | 0 | 2 | 3 | 9 | 0 | 0 | 0 | 8 |
| Chickweed | 9 | 0 | 0 | 0 | 10 | 9 | 0 | 0 | 0 | 8 |
| Cocklebur | 0 | 0 | 0 | 0 | 1 | 0 | 0 | 0 | 0 | 0 |
| Corn | 0 | 0 | 0 | 0 | 0 | 1 | 0 | 0 | 0 | 0 |
| Cotton | — | 0 | 0 | 0 | — | 1 | 0 | 0 | 0 | 0 |
| Crabgrass | 9 | 0 | 3 | 6 | 9 | 10 | 3 | 2 | 8 | 9 |
| Downy brome | 6 | 0 | 0 | 0 | 4 | 6 | 0 | 0 | 0 | 1 |
| Giant foxtail | 10 | 1 | 4 | 6 | 7 | 10 | 4 | 0 | 3 | 9 |
| Lambsquarters | 9 | 3 | 0 | 0 | 9 | 10 | 2 | 0 | 0 | 9 |
| Morningglory | 2 | 0 | 0 | 0 | 8 | 6 | 0 | 0 | 0 | 2 |
| Nutsedge | 0 | 0 | — | — | 0 | — | — | — | 0 | 0 |
| Rape | 2 | 0 | 0 | 0 | 8 | 9 | 0 | 0 | 0 | 3 |
| Redroot pigweed | — | — | — | — | — | — | — | — | — | — |
| Rice | 0 | 0 | 0 | 0 | 0 | 0 | 0 | 2 | 0 | 0 |
| Sorghum | 2 | 0 | 0 | 0 | 0 | 2 | 0 | 0 | 0 | 2 |
| Soybean | 0 | 0 | 0 | 0 | 1 | 2 | 0 | 0 | 0 | 0 |
| Sugar beet | 7 | 0 | 0 | 3 | 9 | 10 | 0 | 0 | 0 | 6 |
| Velvetleaf | 0 | 0 | 0 | 0 | 7 | 7 | 0 | 0 | 1 | 0 |
| Wheat | 2 | 0 | 0 | 0 | 2 | 3 | 0 | 0 | 0 | 0 |
| Wild buckwheat | 0 | 0 | 0 | 0 | 5 | 6 | 0 | 0 | 0 | 2 |
| Wild oat | 9 | 0 | 0 | 3 | 8 | 10 | 0 | 0 | 0 | 7 |

| | COMPOUND | | | | | | COMPOUND | | | | |
|---|---|---|---|---|---|---|---|---|---|---|---|
| Rate 200 g/ha POSTEMERGENCE | 12 | 13 | 14 | 19 | 49 | Rate 200 g/ha PREEMERGENCE | 12 | 13 | 14 | 19 | 49 |
| B. signalgrass | — | 4 | 3 | 4 | 5 | B. signalgrass | — | 10 | 9 | 8 | 10 |
| Barley | 4 | — | — | — | — | Barley | 5 | — | — | — | — |
| Barnyardgrass | 9 | — | — | — | — | Barnyardgrass | 10 | — | — | — | — |
| Bedstraw | 9 | 9 | 10 | 9 | 9 | Bedstraw | 7 | 8 | 10 | 10 | 9 |
| Blackgrass | 4 | 6 | 8 | 4 | 7 | Blackgrass | 10 | 10 | 10 | 9 | 10 |
| Chickweed | 8 | — | — | — | — | Chickweed | 9 | — | — | — | — |
| Cocklebur | 9 | 6 | 10 | 8 | 9 | Cocklebur | 2 | 8 | 4 | 1 | 2 |
| Corn | 5 | 4 | 2 | 3 | 3 | Corn | 3 | 4 | 2 | 4 | 3 |
| Cotton | 10 | — | — | — | — | Cotton | 4 | — | — | — | — |
| Crabgrass | 9 | 8 | 10 | 8 | 9 | Crabgrass | 10 | 10 | 10 | 10 | 10 |
| Downy brome | 6 | — | — | — | — | Downy brome | 10 | — | — | — | — |
| Giant foxtail | 8 | 9 | 6 | 8 | 9 | Giant foxtail | 10 | 10 | 10 | 10 | 10 |
| Lambsquarters | 9 | — | — | — | — | Lambsquarters | 10 | — | — | — | — |
| Morningglory | 9 | 8 | 10 | 8 | 9 | Morningglory | 8 | 6 | 10 | 9 | 5 |
| Nutsedge | 2 | 1 | 3 | 0 | 1 | Nutsedge | 0 | 0 | 0 | 0 | 0 |
| Rape | 10 | 10 | 10 | 9 | 10 | Rape | 9 | 9 | 10 | 8 | 9 |
| Redroot pigweed | — | 9 | 10 | 9 | 9 | Redroot pigweed | — | 10 | 10 | 10 | 10 |
| Rice | 3 | — | — | — | — | Rice | 2 | — | — | — | — |
| Sorghum | 4 | — | — | — | — | Sorghum | 7 | — | — | — | — |
| Soybean | 9 | 8 | 10 | 8 | 10 | Soybean | 0 | 2 | 4 | 1 | 4 |
| Sugar beet | 9 | 9 | 10 | 9 | 9 | Sugar beet | 10 | 10 | 10 | 10 | 10 |
| Velvetleaf | 9 | 9 | 9 | 7 | 9 | Velvetleaf | 10 | 9 | 8 | 9 | 10 |
| Wheat | 3 | 3 | 3 | 1 | 2 | Wheat | 4 | 3 | 3 | 1 | 2 |
| Wild buckwheat | 8 | — | — | — | — | Wild buckwheat | 4 | — | — | — | — |
| Wild oat | 7 | 3 | 5 | 4 | 4 | Wild oat | 10 | 10 | 9 | 8 | 10 |

| | COMPOUND | | | COMPOUND | | | COMPOUND | |
|---|---|---|---|---|---|---|---|---|
| Rate 100 g/ha POSTEMERGENCE | 8 | 10 | Rate 100 g/ha PREEMERGENCE | 8 | 10 | Rate 50 g/ha POSTEMERGENCE | 9 | 12 |
| B. signalgrass | — | — | B. signalgrass | — | — | B. signalgrass | — | — |
| Barley | 0 | 2 | Barley | 0 | 0 | Barley | 0 | 3 |
| Barnyardgrass | 0 | 0 | Barnyardgrass | 0 | 0 | Barnyardgrass | 0 | 5 |
| Bedstraw | 0 | 4 | Bedstraw | 0 | 0 | Bedstraw | 3 | 9 |
| Blackgrass | 0 | 2 | Blackgrass | 0 | 0 | Blackgrass | 0 | 3 |
| Chickweed | 0 | 2 | Chickweed | 0 | 0 | Chickweed | 3 | 7 |
| Cocklebur | 0 | 3 | Cocklebur | 0 | 0 | Cocklebur | 2 | 7 |
| Corn | 0 | 0 | Corn | 0 | 0 | Corn | 1 | 3 |
| Cotton | 0 | 1 | Cotton | 0 | 0 | Cotton | 2 | 10 |
| Crabgrass | 0 | 1 | Crabgrass | 0 | 0 | Crabgrass | 0 | 8 |
| Downy brome | 0 | 1 | Downy brome | 0 | 0 | Downy brome | 0 | 6 |
| Giant foxtail | 0 | 0 | Giant foxtail | 0 | 1 | Giant foxtail | 0 | 4 |
| Lambsquarters | 0 | 2 | Lambsquarters | 0 | 0 | Lambsquarters | 1 | 9 |
| Morningglory | 0 | 2 | Morningglory | 0 | 0 | Morningglory | 2 | 8 |
| Nutsedge | 0 | 0 | Nutsedge | 0 | 0 | Nutsedge | 0 | 0 |

TABLE A-continued

| | | | | | | | | | |
|---|---|---|---|---|---|---|---|---|---|
| Rape | 0 | 5 | Rape | 0 | 0 | Rape | 3 | 10 | |
| Redroot pigweed | — | — | Redroot pigweed | — | — | Redroot pigweed | — | — | |
| Rice | 0 | 0 | Rice | 0 | 0 | Rice | 0 | 2 | |
| Sorghum | 0 | 0 | Sorghum | 0 | 0 | Sorghum | 0 | 2 | |
| Soybean | 0 | 1 | Soybean | 0 | 0 | Soybean | 1 | 8 | |
| Sugar beet | 0 | 4 | Sugar beet | 0 | 0 | Sugar beet | 2 | 9 | |
| Velvetleaf | 0 | 1 | Velvetleaf | 0 | 0 | Velvetleaf | 0 | 8 | |
| Wheat | 0 | 0 | Wheat | 0 | 0 | Wheat | 0 | 2 | |
| Wild buckwheat | 0 | 0 | Wild buckwheat | 0 | 0 | Wild buckwheat | 1 | 8 | |
| Wild oat | 0 | 1 | Wild oat | 0 | 0 | Wild oat | 0 | 3 | |

| | COMPOUND | | | | | | | | |
|---|---|---|---|---|---|---|---|---|---|
| Rate 50 g/ha PREEMERGENCE | 9 | 12 | Giant foxtail | 0 | 10 | | | | |
| | | | Lambsquarters | 0 | 9 | | | | |
| | | | Morningglory | 0 | 5 | | | | |
| B. signalgrass | — | — | Nutsedge | 0 | 0 | | | | |
| Barley | 0 | 1 | Rape | 0 | 7 | | | | |
| Barnyardgrass | 0 | 8 | Redroot pigweed | — | — | | | | |
| Bedstraw | 0 | 5 | Rice | 0 | 1 | | | | |
| Blackgrass | 0 | 8 | Sorghum | 0 | 3 | | | | |
| Chickweed | 0 | 9 | Soybean | 0 | 0 | | | | |
| Cocklebur | 0 | 2 | Sugar beet | 0 | 9 | | | | |
| Corn | 0 | 2 | Velvetleaf | 0 | 10 | | | | |
| Cotton | 0 | 1 | Wheat | 0 | 1 | | | | |
| Crabgrass | 0 | 10 | Wild buckwheat | 0 | 3 | | | | |
| Downy brome | 0 | 7 | Wild oat | 0 | 9 | | | | |

| | COMPOUND | | | | | COMPOUND | | | |
|---|---|---|---|---|---|---|---|---|---|
| Rate 1000 g/ha SPRAYED PADDY | 13 | 14 | 19 | 49 | Rate 200 g/ha SPRAYED PADDY | 13 | 14 | 19 | 49 |
| Barnyardgrass | 9 | 9 | 8 | 9 | Barnyardgrass | 8 | 6 | 7 | 9 |
| Ducksalad | 8 | 7 | 6 | 9 | Ducksalad | 5 | 7 | 4 | 5 |
| Rice | 9 | 5 | 6 | 9 | Rice | 5 | 3 | 5 | 7 |
| S. flatsedge | 9 | 9 | 8 | 9 | S. flatsedge | 8 | 8 | 8 | 9 |

Test B

Seeds of broadleaf signalgrass (*Brachiaria decitie,bens*), bedstraw (*Galium aparille*), blackgrass (*Alopecurus myosuroides*), cocklebur (*Xailhium strumarium*), corn (*Zea mays*), crabgrass (*Digitaria sangitinalis*), giant foxtail (*Setaria faberii*), morningglory (*Ipornoea hederacea*), rape (*Brassica napus*), redroot pigweed (*Amaranthus retroflexus*), soybean (*Glycine max*), sugar beet (*Beta vtilgaris*), velvetleaf (*Abutilon theophrasti*), wheat (*Triticum aestivum*), wild oat (*Avena fatua*) and purple nutsedge (*Cyperus rotundus*) tubers were planted and treated preemergence with test chemicals formulated in a non-phytotoxic solvent mixture which included a surfactant.

At the same time, these crop and weed species were also treated with postemergence applications of test chemicals formulated in the same manner. Plants ranged in height from 2 to 18 cm (1- to 4-leaf stage) for postemergence treatments. Plant species in the flood test consisted of rice (*Oryza sativa*), smallflower flatsedge (*Cyperus difformis*), duck salad (*Heteranthera limosa*) and bamyardgrass (*Echinochloa crus-galli*) grown to the 2-leaf stage for testing. Treated plants and controls were maintained in a greenhouse for twelve to sixteen days, after which all species were compared to controls and visually evaluated. Plant response ratings, summarized in Table B, are based on a scale of 0 to 10 where 0 is no effect and 10 is complete control. A dash (-) response means no test result.

TABLE B

| | COMPOUND | | | COMPOUND | |
|---|---|---|---|---|---|
| Rate 1000 g/ha Postemergence | 5 | 26 | Rate 1000 g/ha Preemergence | 5 | 26 |
| B. signalgrass | 3 | 8 | B. signalgrass | 9 | 9 |
| Barnyardgrass | 8 | 6 | Blackgrass | 9 | 10 |
| Blackgrass | 5 | 9 | Cocklebur | 2 | 8 |
| Cocklebur | 8 | 10 | Corn | 3 | 3 |
| Corn | 3 | 6 | Crabgrass | 10 | 10 |
| Crabgrass | 10 | 8 | Galium | 10 | 7 |
| Ducksalad | 7 | 6 | Giant foxtail | 10 | 10 |
| Galium | 10 | 10 | Morningglory | 10 | 10 |
| Giant foxtail | 7 | 8 | Nutsedge | 10 | 0 |
| Morningglory | 9 | 9 | Rape | 10 | 10 |
| Nutsedge | 0 | 2 | Redroot pigweed | 10 | 10 |
| Rape | 10 | 10 | Soybean | 1 | 8 |
| Redroot pigweed | 10 | 9 | Sugarbeets | 10 | 10 |
| Rice | 5 | 5 | Velvetleaf | 9 | 10 |

TABLE B-continued

| | | | | | |
|---|---|---|---|---|---|
| S. Flatsedge | 8 | 9 | Wheat | 4 | 2 |
| Soybean | 6 | 9 | Wild oats | 10 | 9 |
| Sugarbeets | 10 | 10 | | | |
| Velvetleaf | 8 | 10 | | | |
| Wheat | 4 | 3 | | | |
| Wild oats | 5 | 7 | | | |

| | COMPOUND | | | | | | | |
|---|---|---|---|---|---|---|---|---|
| Rate 500 g/ha Postemergence | 5 | 15 | 20 | 21 | 26 | 29 | 30 | 31 |
| B. signalgrass | 2 | 3 | 3 | — | 8 | 6 | 9 | 2 |
| Barnyardgrass | 6 | 0 | 6 | 0 | 6 | 7 | 6 | 4 |
| Blackgrass | 2 | 3 | 8 | 9 | 8 | 9 | 6 | 2 |
| Cocklebur | 6 | 6 | 9 | 9 | 9 | 9 | 8 | 9 |
| Corn | 2 | 2 | 6 | 2 | 4 | 3 | 3 | 2 |
| Crabgrass | 4 | 6 | 9 | 8 | 8 | 9 | 9 | 8 |
| Ducksalad | 6 | 2 | 5 | 2 | 4 | 8 | 4 | 1 |
| Galium | 10 | 5 | 9 | 9 | 10 | 9 | 10 | 7 |
| Giant foxtail | 3 | 3 | 9 | 7 | 8 | 9 | 9 | 6 |
| Morningglory | 9 | 8 | 10 | 8 | 9 | 10 | 8 | 9 |
| Nutsedge | 0 | 0 | 1 | 0 | 2 | — | 0 | 2 |
| Rape | 10 | 8 | 9 | 9 | 10 | 9 | 10 | 8 |
| Redroot pigweed | 10 | 9 | 9 | 9 | 9 | 9 | 10 | 9 |
| Rice | 4 | 2 | 7 | 3 | 4 | 5 | 5 | 3 |
| S. Flatsedge | 7 | 4 | 9 | 8 | 9 | 9 | 9 | 9 |
| Soybean | 5 | 6 | 9 | 1 | 8 | 9 | 9 | 8 |
| Sugarbeets | 10 | 8 | 10 | 9 | 10 | 9 | 10 | 9 |
| Velvetleaf | 7 | 4 | 10 | 5 | 10 | 10 | 9 | 8 |
| Wheat | 3 | 3 | 5 | 2 | 3 | 3 | 4 | 2 |
| Wild oats | 3 | 4 | 6 | 3 | 5 | 6 | 6 | 2 |

| | COMPOUND | | | | | | | |
|---|---|---|---|---|---|---|---|---|
| Rate 500 g/ha Preemergence | 5 | 15 | 20 | 21 | 26 | 29 | 30 | 31 |
| B. signalgrass | 9 | 5 | 10 | — | 9 | 10 | 9 | 3 |
| Blackgrass | 8 | 5 | 10 | 9 | 9 | 10 | 8 | 1 |
| Cocklebur | 0 | 0 | 9 | 1 | 8 | 9 | 7 | 3 |
| Corn | 0 | 0 | 3 | 1 | 2 | 3 | 1 | 0 |
| Crabgrass | 10 | 10 | 10 | 10 | 10 | 10 | 10 | 10 |
| Galium | 9 | 8 | 9 | 9 | 7 | 10 | 8 | 0 |
| Giant foxtail | 10 | 10 | 10 | 10 | 10 | 10 | 10 | 1 |
| Morningglory | 8 | — | 10 | 8 | 10 | 10 | 10 | 10 |
| Nutsedge | 3 | 0 | — | 0 | 0 | 1 | 0 | 0 |
| Rape | 9 | 8 | 10 | 9 | 10 | 10 | 7 | 3 |
| Redroot pigweed | 10 | 9 | 10 | 10 | 10 | 10 | 10 | 8 |
| Soybean | 0 | 0 | 7 | 0 | 6 | 3 | 4 | 1 |
| Sugarbeets | 10 | 8 | 10 | 10 | 10 | 10 | 10 | 10 |
| Velvetleaf | 8 | 2 | 10 | 7 | 9 | 10 | 10 | 10 |
| Wheat | 2 | 0 | 8 | 1 | 2 | 9 | 3 | 1 |
| Wild oats | 8 | 7 | 10 | 9 | 9 | 10 | 9 | 1 |

| | COMPOUND | | | | | | | | | | | | | | | | | | | | | | | | | | |
|---|---|---|---|---|---|---|---|---|---|---|---|---|---|---|---|---|---|---|---|---|---|---|---|---|---|---|---|---|
| Rate 250 g/ha Post-emergence | 5 | 12 | 13 | 14 | 15 | 16 | 17 | 19 | 20 | 21 | 22 | 23 | 24 | 25 | 26 | 27 | 28 | 29 | 30 | 31 | 34 | 35 | 36 | 37 | 38 | 39 | 40 | 41 | 44 |
| B. signalgrass | 2 | — | 4 | 3 | 3 | 8 | 3 | 3 | 2 | — | — | 3 | 8 | 6 | 7 | 3 | 9 | 4 | 8 | 2 | 3 | 4 | 8 | 7 | 2 | 5 | 5 | 2 | — |
| Barnyardgrass | 5 | 6 | 5 | 5 | 0 | 7 | 4 | 7 | 6 | 0 | 5 | 3 | 5 | 7 | 4 | 4 | 6 | 6 | 4 | 3 | 6 | 7 | 9 | 9 | 2 | 7 | 3 | 4 | 4 |
| Blackgrass | 2 | 9 | 8 | 6 | 2 | 9 | 7 | 4 | 6 | 6 | 8 | 4 | 8 | 8 | 6 | 7 | 8 | 5 | 3 | 1 | 4 | 4 | 8 | 7 | 2 | 6 | 7 | 2 | — |
| Cocklebur | 6 | 9 | 9 | 9 | 6 | 10 | 9 | 8 | 9 | 9 | 9 | 8 | 8 | 9 | 9 | 8 | 9 | 9 | 8 | — | 8 | 9 | 9 | 9 | 2 | 8 | 10 | 8 | — |
| Corn | 2 | 3 | 4 | 3 | 2 | 6 | 4 | 3 | 3 | 1 | 1 | 2 | 5 | 4 | 4 | 3 | 5 | 3 | 3 | 2 | 2 | 3 | 4 | 5 | 1 | 3 | 4 | 2 | — |
| Crabgrass | 4 | 9 | 9 | 9 | 5 | 9 | 9 | 7 | 9 | 7 | 9 | 8 | 9 | 5 | 5 | 5 | 9 | 6 | 9 | 2 | 7 | 9 | 9 | 9 | 2 | 8 | 9 | 8 | — |
| Ducksalad | 6 | 9 | 6 | 3 | 0 | 9 | 8 | 4 | 4 | 0 | 3 | 6 | 7 | 8 | 2 | 5 | 6 | 8 | 2 | 1 | 6 | 4 | 8 | 9 | 3 | 5 | 4 | 4 | 9 |
| Galium | 7 | 9 | 9 | 9 | 4 | — | 10 | 9 | 9 | 8 | 9 | 9 | 9 | 9 | 7 | 9 | 10 | 9 | 10 | 7 | 9 | — | 9 | 9 | — | 10 | — | 10 | — |
| Giant foxtail | 3 | 9 | 9 | 9 | 3 | 9 | 9 | 9 | 7 | 8 | 7 | 7 | 8 | 9 | 5 | 5 | 4 | 10 | 5 | 8 | 3 | 8 | 6 | 8 | 9 | 2 | 9 | 9 | 7 | — |
| Morningglory | 10 | 10 | 8 | 10 | 7 | 10 | 9 | 2 | 10 | 8 | 9 | 9 | 10 | 10 | 9 | 4 | 10 | 9 | 8 | 9 | 8 | 9 | 10 | 8 | 5 | 8 | 9 | 7 | — |
| Nutsedge | 0 | 2 | 3 | 2 | 0 | 0 | 0 | 0 | 0 | 0 | 0 | 0 | 1 | 4 | 1 | 1 | 3 | — | 0 | 1 | 2 | 0 | 2 | 0 | 0 | 2 | 3 | 0 | — |
| Rape | 8 | 10 | 9 | 10 | 8 | 9 | 10 | 7 | 10 | 9 | 10 | 8 | 10 | 10 | 10 | 10 | 10 | 9 | 10 | 8 | 9 | 9 | 9 | 9 | 3 | 10 | 10 | 4 | — |

TABLE B-continued

| | | | | | | | | | | | | | | | | | | | | | | | | | | | | |
|---|---|---|---|---|---|---|---|---|---|---|---|---|---|---|---|---|---|---|---|---|---|---|---|---|---|---|---|---|
| Redroot pigweed | 9 | 9 | 9 | 9 | 9 | 9 | 9 | 9 | 9 | 7 | 10 | 9 | 10 | 9 | 9 | 10 | 9 | 9 | 10 | 9 | 9 | 9 | 8 | 9 | 8 | 10 | 9 | 8 | — |
| Rice | 3 | 6 | 5 | 6 | 0 | 8 | 3 | 7 | 6 | 2 | 3 | 2 | 6 | 5 | 3 | 3 | 5 | 4 | 5 | 2 | 2 | 3 | 7 | 7 | 1 | 6 | 4 | 4 | 4 |
| S. Flatsedge | 7 | 9 | 9 | 9 | 3 | 9 | 9 | 9 | 9 | 8 | 3 | 8 | 9 | 9 | 8 | 6 | 9 | 8 | 8 | 9 | 8 | 9 | 9 | 9 | 6 | 9 | 9 | 9 | |
| Soybean | 4 | 9 | 9 | 8 | 5 | 9 | 7 | 6 | 8 | 1 | 9 | 6 | 9 | 10 | 8 | 8 | 10 | 8 | 9 | 8 | 10 | 10 | 10 | 10 | 6 | 8 | 9 | 1 | — |
| Sugarbeets | 9 | 9 | 9 | 9 | 8 | 9 | 10 | 9 | 10 | 9 | 9 | 9 | 10 | 10 | 10 | 10 | 10 | 9 | 10 | 9 | 9 | 9 | 9 | 8 | 7 | 10 | 10 | 8 | — |
| Velvetleaf | 7 | 9 | 9 | 9 | 3 | 9 | 8 | 7 | 9 | 5 | 9 | 6 | 9 | 9 | 9 | 8 | 9 | 9 | 8 | 6 | 9 | 9 | 9 | 9 | 3 | 8 | 8 | 2 | — |
| Wheat | 2 | 2 | 4 | 3 | 2 | 3 | 1 | 2 | 2 | 1 | 3 | 2 | 2 | 4 | 2 | 2 | 3 | 3 | 3 | 2 | 1 | 1 | 4 | 4 | 1 | 3 | 4 | 2 | — |
| Wild oats | 2 | 6 | 4 | 5 | 3 | 5 | 4 | 3 | 4 | 3 | 7 | 3 | 5 | 6 | 3 | 5 | 6 | 5 | 5 | 1 | 3 | 3 | 6 | 6 | 2 | 5 | 5 | 3 | — |

| | COMPOUND | | | | | | | |
|---|---|---|---|---|---|---|---|---|
| Rate 250 g/ha Postemergence | 45 | 46 | 49 | 51 | 52 | 53 | 54 | 56 | 57 |
| B. signalgrass | 4 | 8 | 5 | — | — | — | — | 3 | 2 |
| Barnyardgrass | 6 | 5 | 6 | 0 | 6 | 1 | 3 | 7 | 4 |
| Blackgrass | 6 | 6 | 8 | 3 | 6 | 6 | 4 | 8 | 3 |
| Cocklebur | 6 | 9 | 10 | 6 | 7 | 6 | 8 | 7 | 8 |
| Corn | 4 | 4 | 4 | 3 | 6 | 1 | 4 | 7 | 2 |
| Crabgrass | — | 10 | 10 | 6 | 9 | 1 | 3 | 6 | 4 |
| Ducksalad | 5 | 2 | 8 | 0 | 4 | 0 | 2 | 9 | 6 |
| Galium | 7 | 9 | 9 | 9 | 9 | 7 | 8 | 9 | 9 |
| Giant foxtail | 6 | 8 | 10 | 4 | 9 | 1 | 2 | 9 | 6 |
| Morningglory | 10 | 10 | 9 | 4 | 9 | 7 | 6 | 9 | — |
| Nutsedge | 0 | 0 | 2 | 0 | 1 | 0 | 1 | 1 | 0 |
| Rape | 9 | 10 | 9 | 7 | 7 | 1 | 6 | 9 | 10 |
| Redroot pigweed | 9 | 10 | 9 | 9 | 9 | 8 | 9 | 10 | 9 |
| Rice | 3 | 5 | 6 | 0 | 5 | 0 | 2 | 8 | 4 |
| S. Flatsedge | 9 | 8 | 9 | 0 | 9 | 5 | 6 | 9 | 9 |
| Soybean | — | 7 | 9 | 5 | 8 | 2 | 7 | 6 | 4 |
| Sugarbeets | 9 | 10 | 9 | 8 | 9 | 7 | 9 | 9 | 9 |
| Velvetleaf | 8 | 8 | 9 | 3 | 6 | 5 | 7 | 9 | 7 |
| Wheat | 2 | 3 | 3 | 3 | 3 | 1 | 2 | 1 | 1 |
| Wild oats | 4 | 5 | 5 | 2 | 9 | 1 | 3 | 4 | 2 |

| | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rate 250 g/ha Pre-emergence | 5 | 12 | 13 | 14 | 15 | 16 | 17 | 19 | 20 | 21 | 22 | 23 | 24 | 25 | 26 | 27 | 28 | 29 | 30 | 31 | 34 | 35 | 36 | 37 | 38 | 39 | 40 | 41 | 45 |
| B. signalgrass | 5 | — | 10 | — | 3 | 10 | 8 | 8 | — | — | — | 9 | 10 | 10 | 7 | 8 | 10 | 10 | 8 | 1 | 8 | 8 | — | — | 2 | 9 | 9 | 8 | 9 |
| Blackgrass | 1 | 10 | 10 | 9 | 1 | 10 | 10 | 6 | 9 | 7 | 9 | 9 | 10 | 10 | 7 | 8 | 10 | 10 | 7 | 0 | 9 | 9 | 10 | 10 | 1 | 6 | 8 | 10 | 10 |
| Cocklebur | 0 | 9 | 8 | 6 | 0 | 7 | 4 | 3 | 7 | 0 | 2 | 8 | 10 | 8 | 3 | 3 | 2 | 5 | — | — | 3 | 7 | 7 | 8 | 0 | — | 10 | 3 | 0 |
| Corn | 0 | 3 | 4 | 1 | 0 | 4 | 2 | 3 | 1 | 1 | 1 | 1 | 5 | 2 | 1 | 0 | 1 | 2 | 1 | 0 | 1 | 1 | 5 | 4 | 0 | 1 | 1 | 1 | 0 |
| Crabgrass | 8 | 10 | 10 | 10 | 2 | 10 | 10 | 10 | 10 | 10 | 10 | 10 | 10 | 10 | 9 | 9 | 10 | 10 | 9 | 9 | 10 | 10 | 10 | 4 | 10 | 10 | 10 | 10 | 10 |
| Galium | 9 | 9 | 8 | 8 | 4 | 10 | 10 | 7 | 9 | 1 | 8 | 10 | 8 | 10 | 7 | 9 | 9 | 9 | 8 | 0 | 9 | 8 | 10 | 9 | 0 | 9 | 10 | 9 | 1 |
| Giant foxtail | 9 | 10 | 10 | 10 | 7 | 10 | 10 | 10 | 10 | 10 | 10 | 10 | 10 | 10 | 9 | 9 | 10 | 10 | 9 | 10 | 10 | 10 | 10 | 4 | 10 | 10 | 10 | 10 | 9 |
| Morningglory | 9 | 10 | 10 | 10 | 0 | 10 | 10 | 10 | 10 | 8 | 9 | 10 | 10 | 10 | 9 | 5 | 10 | 10 | 10 | 10 | 10 | 10 | 10 | 10 | 1 | 10 | 10 | 6 | 10 |
| Nutsedge | 0 | 1 | 0 | 0 | 0 | — | 0 | 0 | 0 | 0 | 1 | 0 | 4 | 0 | — | 5 | 1 | — | 0 | 1 | 1 | 1 | — | 0 | — | 1 | — | 0 |
| Rape | 8 | 10 | 10 | 10 | 5 | 10 | 10 | 9 | 10 | 8 | 10 | 10 | 10 | 10 | 9 | 9 | 9 | 10 | 7 | 1 | 10 | 9 | 10 | 10 | 1 | 10 | 9 | 7 | 7 |
| Redroot pigweed | 10 | 10 | 10 | 10 | 5 | 10 | 10 | 9 | 10 | 10 | 10 | 10 | 10 | 10 | 10 | 10 | 10 | 10 | 10 | 6 | 10 | 10 | 10 | 8 | 10 | 10 | 10 | 10 | 10 |
| Soybean | 0 | 5 | 5 | 2 | 0 | 4 | 3 | 3 | 4 | 0 | 2 | 2 | 8 | 3 | 5 | 1 | 3 | 2 | 3 | 0 | 1 | 4 | 2 | 2 | 0 | 4 | 3 | 1 | 2 |
| Sugarbeets | 9 | 10 | 10 | 10 | 7 | 10 | 10 | 10 | 10 | 10 | 10 | 10 | 10 | 10 | 10 | 10 | 10 | 10 | 10 | 10 | 10 | 10 | 10 | 7 | 10 | 10 | 10 | 10 | 10 |
| Velvetleaf | 8 | 10 | 10 | 10 | 0 | 10 | 10 | 10 | 2 | 10 | 10 | 10 | 10 | 8 | 10 | 10 | 10 | 8 | 8 | 10 | 7 | 10 | 10 | 2 | 10 | 10 | 1 | 10 |
| Wheat | 0 | 3 | 4 | 5 | 0 | 4 | 2 | 2 | 4 | 0 | 6 | 3 | 6 | 1 | 1 | 3 | 1 | 3 | 2 | 0 | 2 | 3 | 4 | 5 | 0 | 2 | 4 | 4 | 0 |
| Wild oats | 6 | 10 | 10 | 10 | 2 | 10 | 8 | 8 | 9 | 7 | 10 | 8 | 10 | 10 | 8 | 8 | 10 | 10 | 8 | 1 | 8 | 9 | 10 | 10 | 2 | 9 | 9 | 8 | 10 |

| | COMPOUND | | | | | | | |
|---|---|---|---|---|---|---|---|---|
| Rate 250 g/ha Preemergence | 46 | 49 | 51 | 52 | 53 | 54 | 56 | 57 |
| B. signalgrass | 9 | 10 | 3 | — | — | — | 9 | 8 |
| Blackgrass | 8 | 10 | 5 | — | 2 | 2 | 9 | 7 |
| Cocklebur | 2 | 8 | 2 | 7 | 0 | 2 | 3 | 0 |
| Corn | 1 | 5 | 0 | 5 | 0 | 0 | 4 | 0 |
| Crabgrass | 9 | 10 | 9 | 9 | 3 | 9 | 10 | 10 |
| Galium | 4 | 9 | 9 | 9 | 7 | 8 | 9 | 8 |
| Giant foxtail | 9 | 10 | 9 | 10 | 2 | 3 | 10 | 9 |
| Morningglory | 9 | 10 | 10 | 8 | 6 | 7 | 10 | 10 |

TABLE B-continued

| | | | | | | | | |
|---|---|---|---|---|---|---|---|---|
| Nutsedge | 0 | 1 | 0 | 0 | 0 | 0 | 0 | — |
| Rape | 7 | 10 | 8 | 9 | 1 | 2 | 10 | 10 |
| Redroot pigweed | 9 | 10 | 10 | 10 | 9 | 6 | 10 | 10 |
| Soybean | 1 | 5 | 1 | 2 | 0 | 1 | 1 | 1 |
| Sugarbeets | 10 | 10 | 10 | 10 | 8 | 9 | 10 | 10 |
| Velvetleaf | 9 | 10 | 5 | 8 | 0 | 7 | 10 | 7 |
| Wheat | 4 | 4 | 3 | 3 | 0 | 1 | 4 | 1 |
| Wild oats | 9 | 10 | 3 | 9 | 2 | 4 | 10 | 9 |

| | COMPOUND | | | | | | | | | | | | | | | | | | | | | | | | | |
|---|---|---|---|---|---|---|---|---|---|---|---|---|---|---|---|---|---|---|---|---|---|---|---|---|---|---|---|
| Rate 125 g/ha Post-emergence | 5 | 12 | 13 | 14 | 15 | 16 | 17 | 19 | 20 | 21 | 22 | 23 | 24 | 25 | 26 | 27 | 28 | 29 | 30 | 31 | 34 | 35 | 36 | 37 | 38 | 39 | 40 | 41 | 44 |
| B. signalgrass | 1 | — | 3 | 3 | 3 | 6 | 2 | 2 | 2 | — | — | 3 | 6 | 4 | 4 | 3 | 6 | 3 | 8 | 2 | 3 | 3 | 6 | 6 | 1 | 5 | 4 | 1 | 5 |
| Barnyardgrass | 3 | 5 | 4 | 4 | 0 | 6 | 3 | 5 | 5 | 0 | 4 | 2 | 4 | 6 | 4 | 3 | 5 | 4 | 4 | 3 | 5 | 4 | 8 | 8 | 1 | 6 | 3 | 3 | 3 |
| Blackgrass | 1 | 7 | 6 | 5 | 2 | 8 | 5 | 4 | 5 | — | 7 | 3 | 3 | 7 | 3 | 7 | 6 | 3 | 3 | 1 | 3 | 4 | 7 | 6 | 1 | 5 | 6 | 1 | 5 |
| Cocklebur | 6 | 8 | 9 | 9 | 5 | 10 | 9 | 7 | 8 | — | 8 | 8 | 8 | 9 | 9 | 8 | 8 | 8 | 8 | 7 | 9 | 9 | 9 | 9 | 2 | 8 | 9 | 6 | — |
| Corn | 2 | 2 | 2 | 2 | 2 | 4 | 4 | 1 | 3 | — | 1 | 1 | 5 | 4 | 3 | 3 | 3 | 3 | 2 | 2 | 3 | 4 | 5 | 1 | 2 | 3 | 1 | 4 |
| Crabgrass | 3 | 9 | 8 | 9 | 4 | 9 | 7 | 4 | 9 | — | 8 | 5 | 8 | 5 | 5 | 5 | 8 | 3 | 8 | 1 | 7 | 6 | 9 | 9 | 1 | 7 | 7 | 7 | 8 |
| Ducksalad | 4 | 9 | — | 3 | 0 | 8 | 8 | 2 | 3 | 0 | 2 | 4 | 6 | 7 | 2 | 4 | 4 | 7 | 0 | 0 | 3 | 3 | 5 | 9 | 2 | 4 | 3 | 3 | 8 |
| Galium | 7 | 9 | 9 | 9 | 4 | 10 | 10 | 8 | 9 | — | 9 | — | 9 | 9 | 7 | — | 10 | 9 | 10 | 4 | 9 | — | 9 | 9 | 7 | 10 | — | 8 | 9 |
| Giant foxtail | 2 | 8 | 7 | 3 | 2 | 9 | 8 | 5 | 4 | — | 4 | 6 | 9 | 5 | 5 | 4 | 6 | 3 | 4 | 3 | 5 | 3 | 8 | 9 | 1 | 7 | 6 | 3 | 8 |
| Morningglory | 7 | 10 | 8 | 10 | 6 | 9 | 9 | 2 | 9 | — | 9 | 7 | 9 | 10 | 6 | 4 | 10 | 6 | 8 | 9 | 8 | 9 | 9 | 8 | 2 | 8 | 9 | 3 | 9 |
| Nutsedge | 0 | 1 | 1 | 1 | 0 | 0 | 0 | 0 | 0 | — | 0 | 0 | 0 | 3 | 0 | 0 | 1 | 0 | 0 | 0 | 1 | 0 | 2 | 0 | 0 | 1 | 0 | 0 | 0 |
| Rape | 6 | 10 | 9 | 10 | 7 | 9 | 9 | 7 | 10 | — | 10 | 7 | 10 | 10 | 10 | 10 | 10 | 9 | 9 | 7 | 9 | 9 | 9 | 9 | 3 | 10 | 10 | 2 | 8 |
| Redroot pigweed | 8 | 9 | 9 | 9 | 9 | 9 | 9 | 9 | 9 | — | 9 | 9 | 10 | 9 | 9 | 10 | 9 | 9 | 8 | 9 | 9 | 9 | 8 | 5 | 10 | 9 | 8 | 9 | |
| Rice | 1 | 5 | 4 | 5 | 0 | 6 | 3 | 5 | 5 | 0 | 2 | 1 | 5 | 4 | 2 | 2 | 4 | 3 | 5 | 2 | 2 | 1 | 6 | 6 | 0 | 6 | 3 | 2 | 3 |
| S. Flatsedge | 7 | 9 | 9 | 3 | 2 | 9 | 9 | 7 | 9 | 5 | 2 | 7 | 8 | 8 | 8 | 4 | 9 | 8 | 7 | 7 | 7 | 6 | 9 | 9 | 5 | 8 | 9 | 7 | 9 |
| Soybean | 4 | 8 | 8 | 8 | 5 | 9 | 7 | 4 | 8 | — | 7 | 5 | 8 | 9 | 8 | 8 | 8 | 8 | 9 | 7 | 9 | 10 | 10 | 9 | 3 | 8 | 8 | 0 | 9 |
| Sugarbeets | 9 | 9 | 9 | 8 | 9 | 9 | 9 | 10 | — | 9 | 10 | 9 | 10 | 9 | 10 | 9 | 10 | 8 | 9 | 9 | 9 | 8 | 4 | 10 | 9 | 8 | 10 | | |
| Velvetleaf | 7 | 9 | 9 | 9 | 3 | 9 | 8 | 3 | 9 | — | 9 | 6 | 9 | 9 | 9 | 8 | 9 | 8 | 8 | 6 | 9 | 9 | 9 | 8 | 2 | 8 | 8 | 0 | 9 |
| Wheat | 2 | 2 | 3 | 2 | 1 | 2 | 1 | 2 | 2 | — | 1 | 1 | 1 | 3 | 2 | 2 | 3 | 3 | 2 | 2 | 1 | 1 | 3 | 4 | 1 | 2 | 3 | 1 | 4 |
| Wild oats | 2 | 3 | 4 | 4 | 3 | 4 | 2 | 2 | 3 | — | 7 | 3 | 4 | 5 | 3 | 5 | 5 | 4 | 3 | 1 | 2 | 3 | 6 | 5 | 1 | 5 | 4 | 2 | 4 |

| | COMPOUND | | | | | | | |
|---|---|---|---|---|---|---|---|---|
| Rate 125 g/ha Postemergence | 45 | 46 | 49 | 51 | 52 | 53 | 54 | 56 | 57 |
| B. signalgrass | 4 | 8 | 4 | — | — | — | — | 3 | 1 |
| Barnyardgrass | 3 | 4 | 5 | 0 | 5 | 0 | 2 | 7 | 4 |
| Blackgrass | 5 | 5 | 6 | 3 | 5 | 4 | 3 | 7 | 2 |
| Cocklebur | 4 | 9 | 10 | 5 | 5 | 6 | 8 | 6 | 7 |
| Corn | 4 | 3 | 3 | 2 | 5 | 0 | 3 | 5 | 2 |
| Crabgrass | 6 | 8 | 9 | 3 | 5 | 1 | 3 | 4 | 3 |
| Ducksalad | 5 | 2 | 8 | 0 | 3 | 0 | 2 | 9 | 5 |
| Galium | 7 | 9 | 9 | 8 | 8 | 8 | 8 | 9 | 9 |
| Giant foxtail | 4 | 6 | 9 | 1 | 8 | 1 | 2 | 7 | 6 |
| Morningglory | 10 | 10 | 8 | 3 | 8 | 6 | 6 | 9 | 9 |
| Nutsedge | 0 | 0 | 2 | 0 | 0 | 0 | 0 | 0 | 0 |
| Rape | 8 | 8 | 9 | 7 | 7 | 0 | 5 | 9 | 8 |
| Redroot pigweed | 9 | 10 | 9 | 9 | 9 | 7 | 9 | 9 | 9 |
| Rice | 3 | 4 | 5 | 0 | 4 | 0 | 0 | 8 | 4 |
| S. Flatsedge | 9 | 7 | 8 | 0 | 9 | 4 | 5 | 9 | 9 |
| Soybean | 9 | 7 | 8 | 4 | 6 | 0 | 4 | 6 | 2 |
| Sugarbeets | 9 | 10 | 9 | 8 | 9 | 7 | 9 | 9 | 9 |
| Velvetleaf | 7 | 8 | 9 | 3 | 6 | 2 | 6 | 8 | 7 |
| Wheat | 2 | 3 | 2 | 2 | 3 | 1 | 1 | 1 | 1 |
| Wild oats | 3 | 4 | 5 | 2 | 4 | 1 | 2 | 4 | 2 |

| | COMPOUND | | | | | | | | | | | | | | | | | | | | | | | | | |
|---|---|---|---|---|---|---|---|---|---|---|---|---|---|---|---|---|---|---|---|---|---|---|---|---|---|---|
| Rate 125 g/ha Pre-emergence | 5 | 12 | 13 | 14 | 15 | 16 | 17 | 19 | 20 | 22 | 23 | 24 | 25 | 26 | 27 | 28 | 29 | 30 | 31 | 34 | 35 | 36 | 37 | 38 | 39 | 40 | 41 | 44 | 45 |
| B. signalgrass | 2 | — | 10 | — | 1 | 10 | 8 | 7 | — | — | 8 | 9 | 10 | 5 | 8 | 10 | 9 | 8 | 1 | 8 | 6 | — | — | 1 | 7 | 9 | 7 | 7 | 8 |

TABLE B-continued

| Weed | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Blackgrass | 0 | 7 | 9 | 9 | 1 | 10 | 6 | 3 | 9 | 8 | 7 | 8 | 9 | 5 | 5 | 9 | 9 | 3 | 0 | 8 | 5 | 10 | 10 | 0 | 6 | 6 | 7 | 2 | 5 |
| Cocklebur | 0 | 6 | — | 3 | 0 | 2 | 4 | 0 | 7 | 0 | 6 | 8 | 7 | — | 1 | 1 | 1 | — | 0 | — | 1 | 2 | 3 | 0 | 7 | 6 | 1 | 0 | — |
| Corn | 0 | 2 | 2 | 1 | 0 | 2 | 0 | 2 | 1 | 1 | 1 | 3 | 1 | 0 | 0 | 1 | 2 | 1 | 0 | 1 | 1 | 2 | 2 | 0 | 0 | 1 | 1 | 2 | 0 |
| Crabgrass | 4 | 10 | 10 | 10 | 1 | 10 | 10 | 9 | 10 | 10 | 10 | 10 | 10 | 9 | 9 | 9 | 10 | 9 | 6 | 9 | 10 | 10 | 10 | 1 | 9 | 10 | 10 | 10 | 10 |
| Galium | 6 | 6 | 8 | 8 | 3 | 10 | 10 | 7 | 9 | 7 | 8 | 8 | 10 | 4 | 7 | 3 | 9 | 7 | 0 | 6 | 8 | 10 | 9 | 0 | 8 | 8 | 6 | 5 | 1 |
| Giant foxtail | 5 | 10 | 10 | 9 | 3 | 10 | 10 | 9 | 10 | 10 | 10 | 10 | 10 | 9 | 9 | 10 | 10 | 10 | 8 | 9 | 10 | 10 | 10 | 3 | 10 | 10 | 10 | 10 | 9 |
| Morningglory | 2 | 10 | 10 | 10 | 0 | 10 | 10 | 9 | 10 | 6 | 8 | 10 | 10 | 5 | 5 | 10 | 10 | 10 | 6 | 6 | 9 | 10 | 9 | 0 | 10 | 10 | 3 | 9 | 9 |
| Nutsedge | 0 | 0 | 0 | 0 | 0 | 0 | 0 | 0 | 0 | 0 | 0 | 0 | 1 | 0 | — | 1 | — | 0 | 0 | 0 | 1 | — | 0 | 0 | — | 1 | 0 | 0 | 0 |
| Rape | 7 | 9 | 10 | 8 | 5 | 10 | 10 | 8 | 9 | 9 | 10 | 10 | 10 | 8 | 6 | 8 | 10 | 7 | 1 | 9 | 8 | 10 | 10 | 0 | 7 | 9 | 4 | 8 | 4 |
| Redroot pigweed | 9 | 10 | 10 | 9 | 1 | 10 | 10 | 9 | 10 | 10 | 10 | 10 | 10 | 8 | 7 | 10 | 10 | 10 | 5 | 10 | 10 | 10 | 10 | 0 | 9 | 8 | 10 | 9 | 9 |
| Soybean | 0 | 4 | 3 | 2 | 0 | 4 | 1 | 1 | 2 | 1 | 1 | 7 | 2 | 4 | 1 | 2 | 2 | 3 | 0 | 1 | 2 | 2 | 1 | 0 | 3 | 3 | 0 | 5 | 1 |
| Sugarbeets | 8 | 10 | 10 | 10 | 3 | 10 | 10 | 10 | 10 | 9 | 10 | 10 | 10 | 10 | 9 | 10 | 10 | 10 | 3 | 10 | 9 | 10 | 10 | 2 | 10 | 10 | 5 | 10 | 10 |
| Velvetleaf | 2 | 10 | 10 | 7 | 0 | 10 | 10 | 7 | 10 | 7 | 8 | 10 | 9 | 8 | 7 | 10 | 10 | 7 | 4 | 8 | 9 | 10 | 8 | 1 | 9 | 10 | 0 | 10 | 7 |
| Wheat | 0 | 2 | 2 | 3 | 0 | 2 | 1 | 0 | 3 | 3 | 2 | 3 | 1 | 1 | 1 | 0 | 3 | 2 | 0 | 2 | 1 | 2 | 3 | 0 | 1 | 3 | 2 | 20 | 0 |
| Wild oats | 4 | 10 | 9 | 9 | 0 | 10 | 7 | 5 | 8 | 9 | 8 | 9 | 10 | 7 | 6 | 10 | 9 | 8 | 0 | 8 | 7 | 10 | 10 | 2 | 9 | 9 | 7 | 5 | 9 |

| | COMPOUND | | | | | | | |
|---|---|---|---|---|---|---|---|---|
| Rate 125 g/ha Preemergence | 46 | 49 | 51 | 52 | 53 | 54 | 56 | 57 |
| B. signalgrass | 9 | 10 | 1 | — | — | — | 7 | 7 |
| Blackgrass | 5 | 10 | 1 | 7 | 2 | 2 | 4 | 2 |
| Cocklebur | 1 | 2 | 1 | 2 | 0 | 1 | 0 | 0 |
| Corn | 1 | 3 | 0 | 5 | 0 | 0 | 2 | 0 |
| Crabgrass | 7 | 10 | 6 | 9 | 0 | 6 | 10 | 9 |
| Galium | 3 | 9 | 7 | 9 | 3 | 6 | 8 | 7 |
| Giant foxtail | 9 | 10 | 9 | 10 | 1 | 3 | 10 | 9 |
| Morningglory | 6 | 10 | 5 | 8 | 0 | 7 | 10 | 10 |
| Nutsedge | 0 | 1 | 0 | 0 | — | 0 | — | 0 |
| Rape | 6 | 10 | 7 | 9 | 0 | 0 | 10 | 9 |
| Redroot pigweed | 9 | 10 | 7 | 10 | 3 | 6 | 10 | 10 |
| Soybean | 1 | 3 | 0 | 0 | 0 | 0 | 1 | 0 |
| Sugarbeets | 10 | 10 | 10 | 10 | 3 | 9 | 10 | 9 |
| Velvetleaf | 9 | 10 | 5 | 6 | 0 | 7 | 10 | 7 |
| Wheat | 3 | 1 | 1 | 3 | 0 | 0 | 3 | 1 |
| Wild oats | 7 | 10 | 2 | 9 | 2 | 1 | 10 | 9 |

| | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rate 62 g/ha Postemergence | 12 | 13 | 14 | 15 | 16 | 17 | 19 | 20 | 21 | 22 | 23 | 24 | 25 | 27 | 28 | 29 | 30 | 31 | 34 | 35 | 36 | 37 | 38 | 39 | 40 | 41 | 44 | 45 | 46 |
| B. signalgrass | — | 2 | 3 | 3 | 3 | 2 | 1 | 1 | — | — | 2 | 3 | 4 | 2 | 6 | 3 | 8 | 2 | 3 | 3 | 5 | 5 | 1 | 3 | 3 | 1 | 3 | 4 | 7 |
| Barnyardgrass | 5 | 4 | 4 | 0 | 4 | 3 | 4 | 4 | 0 | 4 | 2 | 3 | 5 | 2 | 4 | 3 | 4 | 3 | 4 | 4 | 7 | 5 | 0 | 4 | 2 | 3 | 3 | 3 | 3 |
| Blackgrass | 4 | 5 | 4 | 1 | 3 | 3 | 2 | 3 | 3 | 6 | 3 | 3 | 5 | 7 | 4 | 2 | 2 | 1 | 3 | 2 | 7 | 4 | 1 | 2 | 5 | 1 | 3 | 4 | 3 |
| Cocklebur | 8 | 9 | 9 | 4 | 6 | 8 | 7 | 8 | 7 | 7 | 8 | 7 | 9 | 7 | 7 | 8 | 7 | 8 | 7 | 8 | 9 | 9 | 2 | 8 | 8 | — | — | 4 | 9 |
| Corn | 2 | 2 | 2 | 2 | 2 | 2 | 1 | 2 | 1 | 1 | 1 | 3 | 4 | 2 | 3 | 2 | 3 | 2 | 2 | 2 | 3 | 4 | 1 | 2 | 3 | 1 | 4 | 3 | 3 |
| Crabgrass | 7 | 8 | 4 | 3 | 9 | 6 | 3 | 6 | 2 | 6 | 4 | 8 | 3 | 3 | 7 | 3 | 6 | 2 | 5 | 5 | 8 | 5 | 0 | 3 | 5 | 3 | 5 | 2 | 3 |
| Ducksalad | 9 | 2 | 0 | 0 | 8 | 2 | 0 | 2 | 0 | 0 | 1 | 5 | 4 | 3 | 4 | 6 | 0 | 0 | 1 | 2 | 4 | 4 | 0 | 3 | 2 | 2 | 6 | 0 | 1 |
| Galium | 9 | 9 | 8 | 4 | 10 | — | 7 | 8 | 7 | 9 | — | 9 | 9 | 10 | 9 | 8 | 10 | 2 | 9 | 9 | 8 | 8 | 1 | 10 | — | 8 | 9 | 4 | 9 |
| Giant foxtail | 5 | 7 | 2 | 2 | 8 | 6 | 3 | 2 | 2 | 4 | 6 | 7 | 3 | 2 | 5 | 2 | 5 | 2 | 5 | 3 | 7 | 4 | 1 | 6 | 6 | 2 | 6 | 2 | 3 |
| Morningglory | 10 | 8 | 9 | 2 | 8 | 9 | 2 | 9 | 7 | 8 | 7 | 9 | — | 8 | 3 | 8 | 8 | 8 | 8 | 8 | 7 | 1 | 7 | 9 | 3 | 8 | 10 | 7 | |
| Nutsedge | 1 | — | 1 | 0 | 0 | 0 | 0 | 0 | 0 | 0 | 0 | 3 | — | 0 | — | 0 | 0 | 1 | 0 | 2 | 0 | 0 | 0 | 0 | 0 | — | 0 | 0 | |
| Rape | 10 | 9 | 9 | 6 | 9 | 7 | 6 | 8 | 9 | 10 | — | 9 | 9 | 10 | 10 | 8 | 9 | 5 | 9 | 9 | 9 | 3 | 10 | 10 | 2 | 8 | 8 | 8 | |
| Redroot pigweed | 9 | 9 | 8 | 8 | 9 | 9 | 9 | 9 | 4 | 9 | 9 | 10 | 9 | 10 | 9 | 9 | 8 | 8 | 9 | 9 | 8 | 8 | — | 10 | 9 | 7 | 9 | 9 | 9 |
| Rice | 4 | 3 | 4 | 0 | 6 | 2 | 3 | 4 | 0 | 2 | 1 | 5 | 3 | 1 | 4 | 3 | 4 | 1 | 1 | 1 | 5 | 5 | 0 | 5 | 2 | 1 | 3 | 1 | 3 |
| S. Flatsedge | 9 | 8 | 3 | 0 | 9 | 8 | 7 | 8 | 3 | 2 | 7 | 8 | 8 | — | 9 | 4 | 5 | 6 | 5 | 5 | 9 | 8 | 2 | 8 | 6 | 7 | 9 | 8 | 7 |
| Soybean | 6 | 6 | 8 | 5 | 7 | 6 | 4 | 7 | 0 | 7 | 3 | 8 | 8 | 7 | 8 | 8 | 9 | 4 | 10 | 8 | 9 | 9 | 1 | 8 | 8 | 0 | 9 | 9 | 7 |
| Sugarbeets | 9 | 9 | 8 | 8 | 8 | 9 | 9 | 8 | 6 | 9 | 9 | 10 | 9 | 9 | 9 | 9 | 9 | 8 | 9 | 9 | 9 | 8 | 4 | 10 | 9 | 6 | 10 | 9 | 10 |
| Velvetleaf | 9 | 9 | 8 | 3 | 7 | 7 | 3 | 8 | 1 | 9 | 6 | 9 | 8 | 8 | 8 | 8 | 6 | 9 | 9 | 8 | 8 | 1 | 8 | 7 | 0 | 8 | 7 | 8 | |
| Wheat | 1 | 2 | 1 | 0 | 1 | 1 | 1 | 1 | 1 | 1 | 1 | 3 | 1 | 3 | 3 | 1 | 1 | 1 | 3 | 4 | 0 | 2 | 3 | 1 | 2 | 1 | 3 | | |
| Wild oats | 2 | 4 | 3 | 1 | 3 | 2 | 2 | 2 | 2 | 6 | 3 | 2 | 5 | 3 | 4 | 3 | 3 | 1 | 2 | 2 | 5 | 4 | 1 | 2 | 4 | 1 | 2 | 3 | 4 |

TABLE B-continued

| | COMPOUND | | | | | | |
|---|---|---|---|---|---|---|---|
| Rate 62 g/ha Postemergence | 49 | 51 | 52 | 53 | 54 | 56 | 57 |
| B. signalgrass | 3 | — | — | — | — | 2 | 1 |
| Barnyardgrass | 5 | 0 | 4 | 0 | 1 | 6 | 2 |
| Blackgrass | 5 | 2 | 5 | 1 | 3 | 3 | 2 |
| Cocklebur | 9 | 4 | 5 | 3 | 6 | 6 | 6 |
| Corn | 3 | 2 | 3 | 0 | 1 | 3 | 2 |
| Crabgrass | 9 | 2 | 4 | 0 | 2 | 3 | 3 |
| Ducksalad | 6 | 0 | 0 | 0 | 0 | 8 | 3 |
| Galium | 9 | 8 | 8 | 7 | 8 | 9 | 8 |
| Giant foxtail | 8 | 1 | 5 | 1 | 1 | 7 | 4 |
| Morningglory | 8 | 3 | 6 | 1 | 6 | 9 | 9 |
| Nutsedge | 2 | 0 | 0 | 0 | 0 | 0 | 0 |
| Rape | 8 | 7 | 7 | 0 | 4 | 9 | 8 |
| Redroot pigweed | 9 | 9 | 9 | 5 | 6 | 9 | 9 |
| Rice | 4 | 0 | 3 | 0 | 0 | 7 | 3 |
| S. Flatsedge | 8 | 0 | 5 | 2 | 5 | 9 | 8 |
| Soybean | 8 | 4 | 5 | 0 | 4 | 5 | 2 |
| Sugarbeets | 9 | 7 | 9 | 6 | 9 | 9 | 9 |
| Velvetleaf | 9 | 3 | 6 | 2 | 6 | 6 | 7 |
| Wheat | 2 | 2 | 3 | 0 | 1 | 0 | 1 |
| Wild oats | 5 | 2 | 4 | 0 | 2 | 3 | 1 |

| | COMPOUND | | | | | | | | | | | | | | | | | | | | | | | | | |
|---|---|---|---|---|---|---|---|---|---|---|---|---|---|---|---|---|---|---|---|---|---|---|---|---|---|---|
| Rate 62 g/ha Pre-emergence | 12 | 13 | 14 | 15 | 16 | 17 | 19 | 20 | 21 | 22 | 23 | 24 | 25 | 27 | 28 | 29 | 30 | 31 | 34 | 35 | 36 | 37 | 38 | 40 | 41 | 44 | 45 | 46 | 49 |
| B. signalgrass | — | 9 | — | 0 | 9 | 5 | 5 | — | — | — | 7 | 9 | 9 | 6 | 9 | 9 | 7 | 0 | 7 | 3 | — | — | 0 | 8 | 4 | 5 | 8 | 5 | 10 |
| Blackgrass | 7 | 7 | 6 | 0 | 6 | 3 | 2 | 4 | 2 | 3 | 6 | 6 | 8 | 3 | 6 | 5 | 1 | 0 | 3 | 3 | 9 | 10 | 0 | 5 | 3 | 2 | 3 | 3 | 10 |
| Cocklebur | 2 | 5 | 1 | 0 | 1 | 3 | 0 | 3 | 0 | 0 | 5 | 1 | 7 | 0 | — | 1 | — | 0 | 0 | 1 | 2 | 3 | 0 | 6 | 0 | 0 | 0 | 1 | 1 |
| Corn | 1 | 1 | 0 | 0 | 1 | 0 | 0 | 0 | 0 | 0 | 1 | 1 | 1 | 0 | 1 | 1 | 0 | 0 | 1 | 1 | 1 | 1 | 0 | 1 | 0 | 0 | 0 | 0 | 2 |
| Crabgrass | 10 | 10 | 9 | 1 | 10 | 9 | 8 | 8 | 2 | 10 | 9 | 10 | 9 | 4 | 8 | 10 | 8 | 2 | 9 | 9 | 10 | 10 | 1 | 9 | 8 | 9 | 8 | 7 | 10 |
| Galium | 6 | 7 | 8 | 3 | 10 | 9 | — | 8 | 0 | 7 | 8 | 7 | 8 | 5 | 3 | 8 | 6 | 0 | 6 | 7 | 8 | 8 | 0 | 8 | 6 | 3 | 0 | 2 | 9 |
| Giant foxtail | 10 | 10 | 9 | 1 | 10 | 9 | 7 | 8 | 9 | 10 | 9 | 10 | 10 | 7 | 10 | 10 | 9 | 4 | 9 | 8 | 10 | 10 | 2 | 9 | 9 | 9 | 4 | 9 | 10 |
| Morningglory | 7 | 10 | 8 | 0 | 10 | 6 | 9 | 8 | 1 | 4 | 4 | 10 | 8 | 5 | 10 | 9 | 7 | 5 | 4 | 5 | 8 | 8 | 0 | 8 | 3 | 8 | 3 | 3 | 10 |
| Nutsedge | 0 | 0 | 0 | 0 | 0 | 0 | 0 | 0 | 0 | 0 | 0 | 0 | 1 | — | 0 | 0 | 0 | 0 | — | 0 | — | 0 | 0 | 0 | 0 | 0 | 0 | 0 | 0 |
| Rape | 9 | 10 | 8 | 0 | 10 | 10 | 4 | 9 | 8 | 8 | 10 | 10 | 7 | 5 | 8 | 7 | 3 | 1 | 8 | 8 | 9 | 8 | 0 | 9 | 2 | 8 | 0 | 5 | 10 |
| Redroot pigweed | 10 | 10 | 9 | 1 | 10 | 10 | 9 | 10 | 10 | 8 | 10 | 9 | 3 | 9 | 10 | 8 | 2 | 8 | 10 | 10 | 10 | 0 | 8 | 9 | 9 | 9 | 9 | 10 | |
| Soybean | 3 | 1 | 1 | 0 | 1 | 1 | 0 | 1 | 0 | 1 | 1 | 2 | 1 | 1 | 1 | 1 | 0 | 0 | 1 | 1 | 1 | 0 | 1 | 0 | 1 | 0 | 0 | 1 | |
| Sugarbeets | 10 | 10 | 6 | 2 | 10 | 10 | 10 | 10 | 6 | 8 | 10 | 10 | 10 | 9 | 9 | 9 | 8 | 3 | 9 | 8 | 9 | 10 | 0 | 10 | 5 | 10 | 9 | 9 | 10 |
| Velvetleaf | 9 | 8 | 7 | 0 | 10 | 8 | 3 | 10 | 1 | 5 | — | 10 | 9 | 2 | 9 | 10 | 4 | 4 | 8 | 5 | 10 | 7 | 0 | 10 | 0 | 10 | 0 | 8 | 10 |
| Wheat | 2 | 1 | 1 | 0 | 2 | 2 | 0 | 1 | 0 | 2 | 1 | 2 | 1 | 0 | 1 | 1 | 0 | 1 | 1 | 1 | 2 | 0 | 3 | 1 | 2 | 0 | 3 | 1 | |
| Wild oats | 9 | 9 | 8 | 0 | 10 | 7 | 2 | 5 | 5 | 8 | 5 | 9 | 9 | 5 | 8 | 8 | 6 | 0 | 6 | 4 | 10 | 8 | 0 | 8 | 4 | 4 | 9 | 5 | 10 |

| | COMPOUND | | | | | |
|---|---|---|---|---|---|---|
| Rate 62 g/ha Preemergence | 51 | 52 | 53 | 54 | 56 | 57 |
| B. signalgrass | — | — | — | — | 6 | 3 |
| Blackgrass | 1 | 1 | 0 | 1 | 2 | 1 |
| Cocklebur | 1 | 1 | 0 | 0 | 0 | 0 |
| Corn | 0 | 3 | 0 | 0 | 2 | 0 |
| Crabgrass | 6 | 9 | 0 | 4 | 9 | 8 |
| Galium | 4 | 5 | 3 | 4 | 8 | 6 |
| Giant foxtail | 7 | 10 | 0 | 1 | 10 | 9 |
| Morningglory | 4 | 3 | 0 | 3 | 9 | 3 |
| Nutsedge | 0 | 0 | 0 | 0 | 0 | 0 |
| Rape | 7 | 6 | 0 | 0 | 10 | 8 |
| Redroot pigweed | 7 | 9 | 2 | 1 | 10 | 8 |
| Soybean | 0 | 0 | 0 | 0 | 0 | 0 |
| Sugarbeets | 9 | 10 | 2 | 9 | 10 | 7 |
| Velvetleaf | 5 | 5 | 0 | 2 | 9 | 2 |
| Wheat | 0 | 1 | 0 | 0 | 1 | 0 |
| Wild oats | 0 | 4 | 0 | 1 | 10 | 4 |

TABLE B-continued

| | COMPOUND | | | | | | | | | | | | | | | | | | | | | | | | | | |
|---|---|---|---|---|---|---|---|---|---|---|---|---|---|---|---|---|---|---|---|---|---|---|---|---|---|---|---|
| Rate 31 g/ha Post-emergence | 12 | 13 | 14 | 16 | 17 | 19 | 22 | 23 | 24 | 25 | 27 | 28 | 34 | 35 | 36 | 37 | 38 | 39 | 40 | 41 | 44 | 45 | 46 | 49 | 51 | 52 | 53 | 54 | 56 |
| B. signalgrass | — | 2 | 2 | 2 | 1 | 1 | — | 2 | 3 | 3 | 2 | 4 | 2 | 2 | 4 | 4 | 1 | 2 | 3 | 1 | 3 | 3 | 5 | 3 | — | — | — | — | 2 |
| Barnyardgrass | 4 | 3 | 3 | 4 | 2 | 2 | 3 | 2 | 2 | 4 | 1 | 3 | 3 | 3 | 5 | 4 | 0 | 4 | 1 | 2 | 3 | 2 | 3 | 4 | 0 | 3 | 0 | 1 | 6 |
| Blackgrass | 2 | 3 | 2 | 3 | 2 | 1 | 3 | 2 | 2 | 4 | 3 | 3 | 2 | 1 | 4 | 3 | 0 | 2 | 4 | 1 | 3 | 2 | 2 | 4 | 2 | 4 | 0 | 2 | 2 |
| Cocklebur | 8 | 8 | 7 | 5 | 7 | 6 | 3 | 6 | 6 | 9 | 7 | 6 | 7 | 9 | 8 | 8 | 2 | 8 | 8 | — | 8 | 4 | 8 | 9 | 4 | 5 | 3 | 6 | 5 |
| Corn | 1 | 2 | 2 | 2 | 1 | 1 | 1 | 1 | 2 | 3 | 1 | 2 | 2 | 1 | 3 | 3 | 1 | 1 | 3 | 0 | 3 | 3 | 2 | 2 | 2 | 2 | 0 | 1 | 1 |
| Crabgrass | 6 | 5 | 4 | 8 | 3 | 2 | 3 | 2 | 7 | 3 | 2 | 3 | 3 | 3 | 7 | 5 | 0 | 3 | 3 | 3 | 2 | 2 | 2 | 8 | 2 | 3 | 0 | 1 | 3 |
| Ducksalad | 2 | 0 | 0 | 7 | 2 | 0 | 0 | 1 | 1 | 4 | 2 | 1 | 0 | 1 | 3 | 2 | 0 | 2 | 1 | 1 | 3 | 2 | 0 | 3 | 0 | 0 | 0 | 0 | 7 |
| Galium | 8 | 8 | 8 | — | — | 7 | 5 | 9 | 7 | 9 | 8 | 8 | 9 | — | 8 | 8 | 0 | 10 | — | 7 | 7 | 4 | 7 | 9 | 8 | 2 | 8 | 9 |  |
| Giant foxtail | 2 | 5 | 2 | 8 | 4 | 2 | 2 | 3 | 6 | 3 | 2 | 3 | 4 | 2 | 6 | 3 | 1 | 5 | 4 | 2 | 3 | 2 | 2 | 5 | 0 | 3 | 0 | 1 | 7 |
| Morningglory | 10 | — | 10 | 4 | 8 | 2 | 8 | 3 | — | 9 | 2 | — | — | 7 | 8 | 7 | 1 | 7 | 8 | 2 | 8 | 7 | 3 | 6 | 3 | 6 | 1 | 6 | 8 |
| Nutsedge | 1 | 0 | 0 | 0 | 0 | 0 | 0 | 0 | — | 0 | 0 | — | 0 | — | 0 | 0 | 0 | 0 | 0 | 0 | 0 | 2 | 0 | 0 | 0 | 0 | O |  |  |
| Rape | 9 | 8 | 8 | 9 | 7 | 6 | 9 | 7 | — | 8 | 9 | 9 | 9 | 9 | 8 | 9 | 2 | 10 | 10 | 1 | 7 | 7 | 8 | 8 | 7 | 7 | 0 | 2 | 9 |
| Redroot pigweed | 9 | 9 | 8 | 9 | 9 | 8 | 8 | 9 | 10 | 9 | 9 | 9 | 9 | 9 | 6 | 8 | 2 | 9 | 9 | 6 | 8 | 9 | 9 | 9 | 9 | 8 | 4 | 6 | 8 |
| Rice | 4 | 2 | 3 | 5 | 2 | 1 | 0 | 1 | 4 | 2 | 0 | 3 | 1 | 0 | 4 | 4 | 0 | 4 | 2 | 1 | 3 | 0 | 2 | 3 | 0 | 1 | 0 | 0 | 6 |
| S. Flatsedge | 8 | 5 | 1 | 9 | 8 | 7 | 1 | 6 | 7 | 6 | 2 | 8 | 1 | 3 | 9 | 6 | 2 | 8 | 4 | 7 | 8 | 8 | 2 | 7 | 0 | 5 | 2 | 1 | 9 |
| Soybean | 5 | 6 | 7 | 6 | 6 | 4 | 6 | 3 | 4 | 7 | 6 | 8 | 7 | 7 | 7 | 9 | 1 | 7 | 6 | 0 | 5 | 8 | 6 | 8 | 4 | 5 | 0 | 3 | 5 |
| Sugarbeets | 7 | 9 | 7 | 8 | 9 | 8 | 9 | 9 | 10 | 8 | 9 | 9 | 9 | 9 | 9 | 8 | 3 | 9 | 9 | 6 | 9 | 9 | 9 | 9 | 7 | 9 | 5 | 8 | 9 |
| Velvetleaf | 8 | 9 | 7 | 6 | 3 | 8 | 6 | 8 | 8 | 7 | 8 | 7 | 8 | 8 | 9 | 7 | 1 | 6 | 7 | 0 | 6 | 6 | 7 | 8 | 3 | 4 | 0 | 6 | 6 |
| Wheat | 1 | 1 | 1 | 1 | 1 | 1 | 1 | 1 | 1 | 3 | 1 | 2 | 1 | 1 | 3 | 3 | 0 | 2 | 3 | 1 | 2 | 0 | 3 | 2 | 1 | 2 | 0 | 0 | 0 |
| Wild oats | 2 | 2 | 3 | 2 | 2 | 1 | 3 | 2 | 2 | 4 | 2 | 3 | 1 | 1 | 4 | 4 | 0 | 2 | 3 | 1 | 1 | 2 | 2 | 4 | 1 | 3 | 0 | 0 | 2 |

| | COMPOUND |
|---|---|
| Rate 31 g/ha Postemergence | 57 |
| B. signalgrass | 1 |
| Barnyardgrass | 1 |
| Blackgrass | 1 |
| Cocklebur | 6 |
| Corn | 1 |
| Crabgrass | 2 |
| Ducksalad | 2 |
| Galium | 8 |
| Giant foxtail | 3 |
| Morningglory | 9 |
| Nutsedge | 0 |
| Rape | 8 |
| Redroot pigweed | 9 |
| Rice | 3 |
| S. Flatsedge | 6 |
| Soybean | 2 |
| Sugarbeets | 8 |
| Velvetleaf | 6 |
| Wheat | 1 |
| Wild oats | 1 |

| | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|
| Rate 31 g/ha Pre-emergence | 12 | 13 | 14 | 16 | 17 | 19 | 22 | 23 | 24 | 25 | 27 | 28 | 34 | 35 | 36 | 37 | 38 | 39 | 40 | 41 | 44 | 45 | 46 | 49 | 51 | 52 | 53 | 54 | 56 |
| B. signalgrass | — | 9 | — | 8 | 4 | 2 | — | 3 | 9 | 8 | 5 | 9 | 3 | 2 | — | — | 0 | 6 | 8 | 3 | 4 | 5 | 4 | 9 | — | — | — | — | 4 |
| Blackgrass | 3 | 6 | 3 | 3 | 2 | 2 | 1 | 2 | 4 | 4 | 1 | 5 | 2 | 2 | 5 | 8 | 0 | 3 | 4 | 3 | 2 | 3 | 1 | 9 | 0 | 1 | 0 | 0 | 2 |
| Cocklebur | 1 | 1 | 1 | 1 | 1 | 0 | 0 | 2 | 0 | 6 | 0 | — | 0 | 0 | 1 | 1 | 1 | 0 | 1 | — | 0 | 0 | — | 1 | 0 | 0 | 0 | 0 | 0 |
| Corn | 1 | 0 | 0 | 0 | 0 | 0 | 0 | 0 | 1 | 0 | 0 | 0 | 0 | 0 | 1 | 1 | 0 | 0 | 0 | 0 | 0 | 0 | 1 | 0 | 3 | 0 | 0 | 1 |  |
| Crabgrass | 9 | 9 | 7 | 10 | 9 | 6 | 6 | 8 | 9 | 5 | 3 | 7 | 7 | 8 | 10 | 9 | 1 | 9 | 9 | 3 | 5 | 0 | 1 | 10 | 2 | 8 | 0 | 1 | 9 |
| Galium | 6 | 6 | 3 | 7 | 6 | 2 | 3 | 8 | 6 | 8 | — | 1 | 2 | 3 | 7 | 8 | 0 | 3 | 6 | 1 | 2 | 0 | 2 | 9 | — | 3 | 0 | 1 | 7 |
| Giant foxtail | 9 | 9 | 9 | 10 | 9 | 5 | 8 | 9 | 8 | 5 | 8 | 8 | 6 | 10 | 10 | 1 | 10 | 9 | 6 | 8 | 2 | 5 | 10 | 1 | 10 | 0 | 0 | 10 |  |
| Morning- | 7 | 9 | 4 | 10 | 3 | 8 | 2 | 4 | 10 | 6 | 2 | 8 | 2 | 2 | 3 | 7 | 0 | 2 | 7 | 2 | 2 | 1 | 7 | 4 | 2 | 0 | 3 | 3 |  |

TABLE B-continued

| | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| glory | | | | | | | | | | | | | | | | | | | | | | | | | | | | | |
| Nutsedge | 0 | 0 | 0 | — | 0 | 0 | 0 | 0 | 0 | 0 | 0 | 0 | 0 | 0 | 0 | — | 0 | 0 | 0 | 0 | 0 | 0 | 0 | 0 | 0 | 0 | 0 | 0 | |
| Rape | 6 | 9 | 5 | 10 | 10 | 4 | 3 | 9 | 10 | 5 | 2 | 7 | 4 | 3 | 8 | 4 | 0 | 3 | 8 | 0 | 2 | 0 | 3 | 9 | 4 | 5 | 0 | 0 | 9 |
| Redroot pigweed | 10 | 10 | 8 | 10 | 3 | 9 | 5 | 8 | 9 | 6 | 3 | 8 | 3 | 7 | 8 | 10 | 0 | 4 | 8 | 2 | 8 | 5 | 8 | 10 | 7 | 6 | 0 | 1 | 10 |
| Soybean | 1 | 1 | 0 | 1 | 1 | 0 | 1 | 1 | 2 | 1 | 0 | 1 | 0 | 1 | 0 | 1 | 0 | 2 | 0 | 0 | 0 | 0 | 1 | 0 | 0 | 0 | 0 | 0 | |
| Sugarbeets | 10 | 10 | 6 | 10 | 9 | 10 | 7 | 10 | 10 | 9 | 9 | 9 | 9 | 3 | 9 | 9 | 0 | 8 | 9 | 1 | 9 | 2 | 8 | 10 | 6 | 9 | 0 | 9 | 10 |
| Velvetleaf | 8 | 8 | 5 | 8 | 7 | 2 | 4 | 6 | 10 | 7 | 2 | 2 | 6 | 5 | 7 | 5 | 0 | 3 | 7 | 0 | 3 | 0 | 2 | 10 | 1 | 2 | 0 | 0 | 5 |
| Wheat | 1 | 1 | 1 | 1 | 1 | 0 | 1 | 1 | 1 | 0 | 0 | 0 | 0 | 0 | 1 | 1 | 0 | 0 | 1 | 0 | 0 | 0 | 1 | 1 | 0 | 0 | 0 | 0 | |
| Wild oats | 8 | 7 | 8 | 9 | 6 | 0 | 6 | 4 | 7 | 7 | 3 | 7 | 3 | 2 | 8 | 4 | 0 | 3 | 6 | 2 | 0 | 6 | 3 | 10 | 0 | 3 | 0 | 0 | 9 |

| | COMPOUND | | COMPOUND |
|---|---|---|---|
| Rate 31 g/ha Preemergence | 57 | Rate 16 g/ha Postemergence | 44 |
| B. signalgrass | 2 | B. signalgrass | 3 |
| Blackgrass | 1 | Barnyardgrass | — |
| Cocklebur | 0 | Blackgrass | 2 |
| Corn | 0 | Cocklebur | 8 |
| Crabgrass | 3 | Corn | 3 |
| Galium | 2 | Crabgrass | 2 |
| Giant foxtail | 8 | Ducksalad | — |
| Morningglory | 2 | Galium | 7 |
| Nutsedge | 0 | Giant foxtail | 2 |
| Rape | 7 | Morningglory | 8 |
| Redroot pigweed | 5 | Nutsedge | 0 |
| Soybean | 0 | Rape | 7 |
| Sugarbeets | 4 | Redroot pigweed | 8 |
| Velvetleaf | 2 | Rice | — |
| Wheat | 0 | S. Flatsedge | — |
| Wild oats | 3 | Soybean | 3 |
| | | Sugarbeets | 9 |
| | | Velvetleaf | 6 |
| | | Wheat | 1 |
| | | Wild oats | 1 |
| | COMPOUND | Morningglory | 1 |
| Rate 16 g/ha Preemergence | 44 | Nutsedge | 0 |
| | | Rape | 0 |
| B. signalgrass | 2 | Redroot pigweed | 7 |
| Blackgrass | 1 | Soybean | 0 |
| Cocklebur | 0 | Sugarbeets | 7 |
| Corn | 0 | Velvetleaf | 0 |
| Crabgrass | 3 | Wheat | 0 |
| Galium | 1 | Wild oats | 0 |
| Giant foxtail | 3 | | |

Test C

The compounds evaluated in this test were formulated in a non-phytoxic solvent mixture which included a surfactant and applied to the soil surface before plant seedlings emerged (preemergence application), to water that covered the soil surface (flood application), and to plants that were in the one-to-four leaf stage (postemergence application). A sandy loam soil was used for the preemergence and postemergence tests, while a silt loam soil was used in the flood application. Water depth was approximately 2.5 cm for the flood application and was maintained at this level for the duration of the test.

Plant species in the preemergence and postemergence tests consisted of barnyardgrass (*Echinochloa crus-galli*), winter barley (*Hordeum vulgare*), bedstraw (*Galium aparine*), blackgrass (*Alopecurus myosuroides*), chickweed (*Stellaria media*), cocklebur (*Xanthiutn strumarium*), corn 1 (*Zea mays*), cotton (*Gossypium hirsutum*), crabgrass (*Digitaria sanguinalis*), downy brome (*Bromus tectorum*), giant foxtail (*Setaria faberii*), johnsongrass (*Sorghum halpense*), lambsquarters (*Chenopodium album*), morningglory (*Ipomoea hederacea*), pigweed (*Amaranthus retroflexus*), rape (*Brassica napus*), Italian ryegrass (*Lolium multiflonum*), soybean (*Glycine max*), speedwell (*Veronica persica*), sugar beet (*Beta vulgaris*), velvetleaf (*Abutilon theophrasti*), wheat (*Triticum aestivum*), wild buckwheat (*Polygonum convolvulus*), and wild oat (*Avena fatua*). All plant species were planted one day before application of the compound for the preemergence portion of this test. Plantings of these species were adjusted to produce plants of appropriate size for the postemergence portion of the test. Plant species in the flood test consisted of rice (*Oryza sativa*), umbrella sedge (*Cyperus difformis*), duck salad (*Heteranthera limosa*) and barnyardgrass 1 (*Echinochloa crus-galli*) to the 2 leaf stage for testing.

All plant species were grown using normal greenhouse practices. Visual evaluations of injury expressed on treated plants, when compared to untreated controls, were recorded approximately fourteen to twenty one days after application of the test compound. Plant response to the test compound is summarized in Table C, recorded on a 0 to 100 scale where 0 is no effect and 100 is complete control. A dash (-) response means no test result.

TABLE C

| Rate 500 g/ha POSTEMERGENCE | COMPOUND 6 | Rate 500 g/ha PREEMERGENCE | COMPOUND 6 | Rate 250 g/ha POSTEMERGENCE | COMPOUND 6 |
|---|---|---|---|---|---|
| Barley (winter) | 40 | Barley (winter) | 10 | Barley (winter) | 30 |
| Barnyardgrass | 60 | Barnyardgrass | 85 | Barnyardgrass | 40 |
| Barnyardgrass 1 | 80 | Bedstraw | 80 | Barnyardgrass 1 | 50 |
| Bedstraw | 95 | Blackgrass | 100 | Bedstraw | 90 |
| Blackgrass | 40 | Chickweed | 95 | Blackgrass | 35 |
| Chickweed | 90 | Cocklebur | 0 | Chickweed | 90 |
| Cocklebur | 80 | Corn 1 | 0 | Cocklebur | 70 |
| Corn 1 | 30 | Cotton | 0 | Corn 1 | 30 |
| Cotton | 100 | Crabgrass | 100 | Cotton | 70 |
| Crabgrass | 80 | Downy brome | 70 | Crabgrass | 70 |
| Downy brome | 30 | Giant foxtail | 100 | Downy brome | 20 |
| Ducksalad | 50 | Italn. ryegrass | 50 | Ducksalad | 30 |
| Giant foxtail | 50 | Johnsongrass | 100 | Giant foxtail | 30 |
| Italn. ryegrass | 35 | Lambsquarter | 90 | Italn. ryegrass | 25 |
| Johnsongrass | 70 | Morningglory | 100 | Johnsongrass | 50 |
| Lambsquarter | 100 | Rape | 100 | Lambsquarter | 90 |
| Morningglory | 90 | Redroot pigweed | 100 | Morningglory | 90 |
| Rape | 100 | Soybean | 0 | Rape | 100 |
| Redroot pigweed | 90 | Speedwell | 100 | Redroot pigweed | 90 |
| Rice japonica | 20 | Sugar beet | 100 | Rice japonica | 10 |
| Soybean | 80 | Velvetleaf | 40 | Soybean | 70 |
| Speedwell | 100 | Wheat | 0 | Speedwell | 100 |
| Sugar beet | 90 | Wild buckwheat | 70 | Sugar beet | 90 |
| Umbrella sedge | 80 | Wild oat | 95 | Umbrella sedge | 80 |
| Velvetleaf | 70 | | | Velvetleaf | 50 |
| Wheat | 25 | | | Wheat | 25 |
| Wild buckwheat | 95 | | | Wild buckwheat | 90 |
| Wild oat | 60 | | | Wild oat | 50 |

| Rate 250 g/ha PREEMERGENCE | COMPOUND 6 | Rate 125 g/ha POSTEMERGENCE | COMPOUND 6 | Rate 125 g/ha PREEMERGENCE | COMPOUND 6 |
|---|---|---|---|---|---|
| Barley (winter) | 0 | Barley (winter) | 25 | Barley (winter) | 0 |
| Barnyardgrass | 35 | Barnyardgrass | 20 | Barnyardgrass | 20 |
| Bedstraw | 70 | Barnyardgrass 1 | 30 | Bedstraw | 30 |
| Blackgrass | 80 | Bedstraw | 90 | Blackgrass | 70 |
| Chickweed | 95 | Blackgrass | 30 | Chickweed | 70 |
| Cocklebur | 0 | Chickweed | 90 | Cocklebur | 0 |
| Corn 1 | 0 | Cocklebur | 70 | Corn 1 | 0 |
| Cotton | 0 | Corn 1 | 25 | Cotton | 0 |
| Crabgrass | 100 | Cotton | 70 | Crabgrass | 90 |
| Downy brome | 20 | Crabgrass | 60 | Downy brome | 10 |
| Giant foxtail | 100 | Downy brome | 10 | Giant foxtail | 95 |
| Italn. ryegrass | 30 | Ducksalad | 20 | Italn. ryegrass | 20 |
| Johnsongrass | 80 | Giant foxtail | 30 | Johnsongrass | 80 |
| Lambsquarter | 90 | Italn. ryegrass | 20 | Lambsquarter | 70 |
| Morningglory | 70 | Johnsongrass | 40 | Morningglory | 35 |
| Rape | 80 | Lambsquarter | 90 | Rape | 40 |
| Redroot pigweed | 100 | Morningglory | 80 | Redroot pigweed | 100 |
| Soybean | 0 | Rape | 100 | Soybean | 0 |
| Speedwell | 100 | Redroot pigweed | 90 | Speedwell | 90 |
| Sugar beet | 100 | Rice japonica | 0 | Sugar beet | 80 |
| Velvetleaf | 20 | Soybean | 60 | Velvetleaf | 10 |
| Wheat | 0 | Speedwell | 100 | Wheat | 0 |
| Wild buckwheat | 70 | Sugar beet | 90 | Wild buckwheat | 40 |
| Wild oat | 80 | Umbrella sedge | 70 | Wild oat | 50 |
| | | Velvetleaf | 40 | | |
| | | Wheat | 15 | | |
| | | Wild buckwheat | 80 | | |
| | | Wild oat | 40 | | |

| Rate 62 g/ha POSTEMERGENCE | COMPOUND 6 | Rate 62 g/ha PREEMERGENCE | COMPOUND 6 |
|---|---|---|---|
| Barley (winter) | 25 | Barley (winter) | 0 |
| Barnyardgrass | 15 | Barnyardgrass | 0 |
| Barnyardgrass 1 | 20 | Bedstraw | 20 |
| Bedstraw | 70 | Blackgrass | 35 |
| Blackgrass | 20 | Chickweed | 50 |
| Chickweed | 70 | Cocklebur | 0 |
| Cocklebur | 60 | Corn 1 | 0 |
| Corn 1 | 25 | Cotton | 0 |
| Cotton | 30 | Crabgrass | 35 |

TABLE C-continued

| | | | |
|---|---|---|---|
| Crabgrass | 40 | Downy brome | 0 |
| Downybrome | 0 | Giant foxtail | 90 |
| Ducksalad | 0 | Italn. ryegrass | 10 |
| Giant foxtail | 20 | Johnsongrass | 20 |
| Italn. ryegrass | 15 | Lambsquarter | 40 |
| Johnsongrass | 40 | Morningglory | 0 |
| Lambsquarter | 90 | Rape | 0 |
| Morningglory | 80 | Redroot pigweed | 100 |
| Rape | 90 | Soybean | 0 |
| Redroot pigweed | 90 | Speedwell | 80 |
| Rice japonica | 0 | Sugar beet | 80 |
| Soybean | 50 | Velvetleaf | 10 |
| Speedwell | 100 | Wheat | 0 |
| Sugar beet | 90 | Wild buckwheat | 20 |
| Umbrella sedge | 50 | Wild oat | 10 |
| Velvetleaf | 30 | | |
| Wheat | 10 | | |
| Wild buckwheat | 80 | | |
| Wild oat | 40 | | |

Test D

Compounds evaluated in this test were formulated in a non-phytotoxic solvent mixture which included a surfactant and applied to plants that were grown for various periods of time before treatment (postemergence application). A mixture of sandy loam soil and greenhouse potting mix in a 60:40 ratio was used for the postemergence test.

Plantings of these crops and weed species were adjusted to produce plants of appropriate size for the postemergence test. All plant species were grown using normal greenhouse practices. Crop and weed species include arrowleaf sida (*Sida rhombifolia*), barnyardgrass (*Echinochloa crus-galli*), cocklebur (*Xanthium strumarium*), common ragweed (*Ambrosia elatior*), corn 1 (*Zea mays*), cotton (*Gossypium hirsutum*), eastern black nightshade (*Solanum ptycanthum*), fall panicum (*Panicum dichotomiflorum*), field bindweed (*Convolvulus arvensis*), giant foxtail (*Setaria faberii*), hairy beggarticks (*Bidens pilosa*), ivyleaf morningglory (*Ipomoea hederacea*), johnsongrass (*Sorghum halepense*), ladysthumb smartweed (*Polygonum persicaria*), lambsquarters (*Chenopodium album*), large crabgrass (*Digitaria sanguinalis*), purple nutsedge (*Cyperus rotundus*), redroot pigweed (*Amaranthus retroflexus*), soybean 1 (*Glycine max*), surinam grass (*Brachiaria decumbens*), velvetleaf (*Abutilon theophrasti*) and wild poinsettia (*Euphorbia heterophylla*).

Treated plants and untreated controls were maintained in a greenhouse for approximately 14 to 21 days, after which all treated plants were compared to untreated controls and visually evaluated. Plant response ratings, summarized in Table D, were based upon a 0 to 100 scale where 0 was no effect and 100 was complete control. A dash response (-) means no test result.

TABLE D

| | COMPOUND | | | | | | | | | | |
|---|---|---|---|---|---|---|---|---|---|---|---|
| Rate 280 g/ha PREEMERGENCE | 12 | 13 | 14 | 20 | 22 | 25 | 34 | 35 | 49 | 56 | 57 |
| Arrowleaf sida | 100 | 100 | 100 | 100 | 100 | 100 | 95 | 100 | 100 | 100 | 95 |
| Barnyardgrass | 100 | 60 | 10 | 80 | 5 | 30 | 100 | 90 | 100 | 40 | 20 |
| Cocklebur | 20 | 80 | 30 | 50 | 0 | 50 | 35 | 70 | 40 | 25 | 10 |
| Common ragweed | 100 | 100 | 100 | 100 | 80 | 100 | 100 | 100 | 100 | 100 | — |
| Corn 1 | 5 | 5 | 5 | 5 | 0 | 10 | 15 | 10 | 5 | 50 | 10 |
| Cotton | 100 | 100 | 80 | 30 | 20 | 30 | 75 | 80 | 60 | 50 | 65 |
| E. blacknightsh | 100 | 100 | 100 | 100 | 100 | 100 | 95 | 100 | 100 | 100 | 100 |
| Fall panicum | 100 | 100 | 100 | 100 | 100 | 100 | 100 | 100 | 100 | 100 | 85 |
| Field bindweed | 100 | 100 | 100 | 100 | 80 | 100 | 100 | 100 | 100 | 100 | 100 |
| Giant foxtail | 100 | 100 | 100 | 100 | 100 | 100 | 100 | 100 | 100 | 70 | 100 |
| H. beggarticks | 100 | 100 | 100 | 100 | 70 | 10 | 100 | 95 | 90 | 95 | 65 |
| I. morningglory | 100 | 100 | 80 | 100 | 5 | 100 | 60 | 100 | 100 | 100 | 80 |
| Johnsongrass | 100 | 50 | 50 | 70 | 50 | 20 | 65 | 75 | 100 | 25 | 15 |
| Ladysthumb | 100 | — | 100 | — | — | 100 | 100 | 100 | — | 100 | 100 |
| Lambsquarters | 100 | 100 | 100 | 100 | 100 | 100 | 100 | 100 | 100 | 100 | 100 |
| Large crabgrass | 100 | 100 | 100 | 100 | 100 | 100 | 100 | 100 | 100 | 100 | 100 |
| Purple nutsedge | 0 | 10 | 0 | 5 | 0 | 0 | 0 | 0 | 5 | 20 | 0 |
| Redroot pigweed | 100 | 100 | 100 | 100 | 100 | 100 | 100 | 100 | 100 | 100 | 100 |
| Soybean 1 | 60 | 50 | 15 | 25 | 20 | 10 | 30 | 20 | 30 | 30 | 0 |
| Surinam grass | 100 | 85 | 70 | 100 | 55 | 95 | 90 | 85 | 100 | 60 | 40 |
| Velvetleaf | 100 | 90 | 90 | 100 | 70 | 100 | 100 | 100 | 100 | 100 | 100 |
| Wild poinsettia | 100 | 100 | 80 | 90 | 50 | 50 | 75 | 100 | 90 | 100 | 75 |

| | COMPOUND | | | | | | | | | | | | | | | |
|---|---|---|---|---|---|---|---|---|---|---|---|---|---|---|---|---|
| Rate 140 g/ha | 12 | 13 | 14 | 16 | 17 | 20 | 22 | 25 | 29 | 34 | 35 | 36 | 37 | 40 | 49 | 56 | 57 |

TABLE D-continued

| PREEMERGENCE | | | | | | | | | | | | | | | | |
|---|---|---|---|---|---|---|---|---|---|---|---|---|---|---|---|---|
| Arrowleaf sida | 100 | 100 | 100 | 100 | 90 | 100 | 100 | 95 | 90 | 95 | 95 | 95 | 95 | 90 | 100 | 100 | 100 |
| Barnyardgrass | 100 | 40 | 5 | 20 | 20 | 10 | 5 | 10 | 35 | 40 | 25 | 20 | 40 | 70 | 70 | 40 | 20 |
| Cocklebur | 5 | 5 | 5 | 10 | — | 50 | 0 | 10 | — | 20 | 10 | 0 | 20 | — | 40 | 10 | 10 |
| Common ragweed | 85 | 100 | 100 | 20 | 25 | 100 | 55 | 95 | — | 100 | 60 | 95 | 90 | 100 | 100 | 100 | — |
| Corn 1 | 5 | 5 | 5 | 35 | 20 | 5 | 0 | 10 | 10 | 10 | 10 | 20 | 10 | 0 | 5 | 35 | 10 |
| Cotton | 75 | 80 | 40 | 15 | 15 | 95 | — | 20 | 70 | 50 | 40 | 60 | 100 | 0 | 55 | 20 | 40 |
| E. blacknightsh | 100 | 100 | 100 | 95 | 100 | 100 | 70 | 80 | 95 | 90 | 95 | 100 | 100 | 90 | 100 | 100 | 100 |
| Fall panicum | 100 | 100 | 100 | 100 | 70 | 100 | 90 | 95 | 95 | 100 | 95 | 100 | 100 | 100 | 100 | 90 | 70 |
| Field bindweed | 100 | 100 | 100 | 90 | 95 | 100 | — | 100 | 100 | 100 | 100 | 100 | 100 | 95 | 100 | 100 | 75 |
| Giant foxtail | 100 | 100 | 100 | 50 | 100 | 100 | 90 | 85 | 100 | 100 | 60 | 100 | 100 | 25 | 100 | 100 | 95 |
| H. beggarticks | 80 | 100 | 85 | 10 | 90 | 100 | — | 10 | 35 | 95 | 95 | 95 | 95 | 20 | 50 | 10 | 65 |
| I. morningglory | 100 | 100 | 80 | 60 | 25 | 100 | 5 | 50 | — | 60 | 30 | 40 | 75 | 20 | 100 | 85 | 75 |
| Johnsongrass | 100 | 50 | 10 | 20 | 50 | 30 | 20 | 10 | 85 | 40 | 25 | 20 | 40 | 50 | 55 | 10 | 10 |
| Ladysthumb | 100 | — | 100 | — | — | 100 | — | 100 | 100 | 95 | 100 | 100 | 100 | — | — | 80 | 100 |
| Lambsquarters | 100 | 100 | 100 | 95 | 95 | 100 | 80 | 100 | 100 | 100 | 100 | 100 | 100 | 100 | 100 | 100 | 100 |
| Large crabgrass | 100 | 100 | 100 | 100 | 100 | 100 | 100 | 100 | 100 | 100 | 100 | 100 | 100 | 100 | 100 | 50 | 95 |
| Purple nutsedge | 0 | 0 | 0 | — | 0 | 5 | 0 | 0 | — | 0 | 0 | 0 | 0 | 0 | 0 | 0 | 0 |
| Redroot pigweed | 100 | 100 | 100 | 100 | 100 | 100 | 100 | 100 | 100 | 100 | 100 | 100 | 100 | 100 | 100 | 100 | 100 |
| Soybean 1 | 50 | 20 | 5 | 0 | 0 | 15 | 5 | 10 | 10 | 15 | 15 | 50 | 15 | 0 | 30 | 15 | 0 |
| Surinam grass | 100 | 80 | 70 | 30 | 75 | 70 | 20 | 70 | 95 | 80 | 35 | 80 | 100 | 25 | 100 | 50 | 40 |
| Velvetleaf | 100 | 90 | 90 | 50 | 90 | 70 | 50 | 80 | 95 | 100 | 100 | 100 | 100 | 85 | 100 | 100 | 100 |
| Wild poinsettia | 50 | 80 | 10 | 100 | 60 | 60 | 30 | 40 | 65 | 75 | 90 | 100 | 70 | 60 | 80 | 100 | 40 |

| | COMPOUND | | | | | | | | | | | | | | | |
|---|---|---|---|---|---|---|---|---|---|---|---|---|---|---|---|---|
| Rate 10 g/ha PREEMERGENCE | 12 | 13 | 14 | 16 | 17 | 20 | 22 | 25 | 29 | 34 | 35 | 36 | 37 | 40 | 49 | 56 | 57 |
| Arrowleaf sida | 100 | 100 | 100 | 90 | 85 | 100 | 95 | 100 | 75 | 90 | 80 | 90 | 95 | 90 | 100 | 100 | 95 |
| Barnyardgrass | 5 | 5 | 5 | 10 | 10 | 5 | 0 | 10 | 10 | 20 | 20 | 20 | 20 | 25 | 10 | 20 | 10 |
| Cocklebur | 0 | 5 | 0 | 10 | 10 | 5 | 0 | 0 | 0 | 10 | 0 | — | 20 | 0 | 0 | 0 | 0 |
| Common ragweed | 85 | 100 | 95 | 10 | 10 | 80 | 5 | 70 | — | 60 | 50 | 100 | 100 | 95 | 60 | 20 | — |
| Corn 1 | 0 | 5 | 0 | 10 | 0 | 5 | 0 | 5 | 10 | 10 | 10 | 15 | 0 | 0 | 5 | 25 | 5 |
| Cotton | 5 | 5 | 40 | 10 | — | 5 | 0 | 20 | 40 | 25 | — | 40 | 20 | 0 | 55 | 10 | 15 |
| E. blacknightsh | 100 | 100 | 100 | 95 | 100 | 100 | 50 | 50 | 85 | 90 | 60 | 100 | 100 | 80 | 100 | 100 | 80 |
| Fall panicum | 100 | 100 | 100 | 95 | 60 | 100 | 5 | 80 | 30 | 100 | 100 | 100 | 100 | 100 | 100 | 70 | 25 |
| Field bindweed | 100 | 100 | 100 | 80 | 60 | 100 | 10 | 70 | 70 | 80 | 100 | 100 | 90 | 60 | 100 | 95 | 75 |
| Giant foxtail | 100 | 100 | 100 | 50 | 95 | 100 | 45 | 20 | 95 | 80 | 10 | 100 | 10 | 20 | 100 | 80 | 80 |
| H. beggarticks | 80 | 100 | 80 | 10 | 80 | 100 | 50 | 10 | 35 | 70 | 95 | 50 | 85 | 20 | 45 | — | 20 |
| I. morningglory | 80 | 5 | 10 | 50 | 10 | 80 | 5 | 25 | 50 | 35 | 30 | 25 | 50 | 20 | 30 | 40 | 50 |
| Johnsongrass | 50 | 30 | 10 | 20 | 25 | 10 | 5 | 10 | 20 | 15 | 10 | 20 | 25 | 20 | 50 | 0 | 10 |
| Ladysthumb | 100 | — | 100 | — | — | 60 | 40 | 50 | 100 | 70 | 100 | 100 | 70 | — | — | 80 | 50 |
| Lambsquarters | 100 | 100 | 100 | 80 | 90 | 100 | 80 | 95 | — | 100 | 100 | 100 | 100 | 100 | 100 | 100 | 80 |
| Large crabgrass | 100 | 100 | 100 | 75 | 100 | 100 | 40 | 60 | 100 | 100 | — | 75 | 100 | 80 | 100 | 40 | 75 |
| Purple nutsedge | 0 | 0 | 0 | 0 | 0 | 0 | 0 | 0 | 0 | 0 | 0 | 0 | 0 | 0 | 0 | 0 | 0 |
| Redroot pigweed | 100 | 100 | 100 | 100 | 100 | 100 | 100 | 100 | 100 | 95 | 100 | 100 | 100 | 100 | 100 | 100 | 100 |
| Soybean 1 | 5 | 5 | 5 | 0 | 0 | 5 | 0 | 0 | 5 | 10 | 5 | 20 | 10 | 0 | 5 | 0 | 0 |
| Surinam grass | 50 | 30 | 10 | 20 | 25 | 40 | 20 | 40 | 70 | 40 | 20 | 50 | 70 | 20 | 80 | 20 | 30 |
| Velvetleaf | 90 | 80 | 80 | 40 | 70 | 70 | 5 | 80 | 65 | 90 | 90 | 100 | 100 | 65 | 100 | 100 | 75 |
| Wild poinsettia | 20 | 60 | 10 | 40 | 10 | 50 | 5 | 25 | 20 | 40 | 100 | 90 | 50 | 10 | 50 | 20 | 10 |

| | COMPOUND | | | | | | | | | | | | | | | |
|---|---|---|---|---|---|---|---|---|---|---|---|---|---|---|---|---|
| Rate 35 g/ha PREEMERGENCE | 12 | 13 | 14 | 16 | 17 | 20 | 22 | 25 | 29 | 34 | 35 | 36 | 37 | 40 | 49 | 56 | 57 |
| Arrowleaf sida | 100 | 90 | 100 | 90 | 100 | 95 | 50 | 90 | 50 | 90 | 75 | 90 | 85 | 90 | 90 | 100 | 70 |
| Barnyardgrass | 0 | 0 | 0 | 10 | 10 | 5 | 0 | 10 | 10 | 10 | 10 | 10 | 10 | 20 | 5 | 10 | 0 |
| Cocklebur | 0 | 0 | 0 | — | — | 0 | 0 | — | 0 | 0 | 0 | — | 10 | 0 | 0 | 0 | — |
| Common ragweed | 50 | 70 | 40 | 10 | 10 | 30 | 5 | 10 | — | 20 | 10 | 100 | 50 | 10 | 50 | 0 | — |
| Corn 1 | 0 | 0 | 0 | 0 | 0 | 5 | 0 | 0 | 10 | 5 | 5 | 15 | 0 | 0 | 0 | 0 | 5 |
| Cotton | 5 | 5 | 10 | 5 | 0 | 60 | 0 | 10 | 20 | 15 | 10 | 15 | 10 | 0 | 10 | 10 | — |
| E. blacknightsh | 100 | 95 | 100 | 95 | 80 | 100 | 40 | 35 | 70 | 40 | 50 | 95 | — | 80 | 100 | 90 | 80 |
| Fall panicum | 100 | 40 | 50 | 50 | 25 | 10 | — | 35 | 20 | 70 | 90 | 90 | 80 | 65 | 80 | 20 | 0 |
| Field bindweed | 70 | 100 | 90 | 60 | 25 | 100 | 10 | 65 | 50 | 100 | 95 | 100 | 100 | 20 | 100 | 85 | 65 |
| Giant foxtail | 100 | 100 | 80 | 25 | 20 | 70 | 5 | 10 | 85 | 20 | 10 | 40 | 10 | 0 | 100 | 10 | 50 |
| H. beggarticks | 30 | 70 | 30 | 10 | 50 | 100 | 50 | 0 | 20 | 20 | 90 | 20 | 10 | 10 | 40 | 0 | 20 |
| I. morningglory | 10 | 5 | 5 | 50 | 10 | 60 | 0 | 20 | 10 | 20 | 30 | 20 | 20 | 10 | 10 | 20 | 20 |
| Johnsongrass | 5 | 10 | 0 | 10 | 10 | 10 | 0 | 10 | 10 | 10 | 10 | 10 | 10 | 20 | 5 | 0 | 5 |
| Ladysthumb | 100 | — | 100 | — | — | 60 | — | 40 | 65 | 60 | 100 | 90 | — | — | — | 20 | — |
| Lambsquarters | 100 | 100 | 100 | 20 | 80 | 100 | 60 | 85 | 95 | 95 | 95 | 100 | 100 | 20 | 100 | 100 | 20 |
| Large crabgrass | 100 | 100 | 100 | 50 | 75 | 100 | 40 | 50 | 85 | 100 | 100 | 50 | 25 | 50 | 80 | 30 | 25 |
| Purple nutsedge | 0 | 0 | 0 | 0 | 0 | 0 | 0 | 0 | 0 | 0 | 0 | 0 | 0 | 0 | 0 | 0 | 0 |
| Redroot pigweed | 100 | 100 | 100 | 50 | 100 | 100 | 50 | 80 | 100 | 90 | 50 | 90 | 100 | 80 | 100 | 95 | 95 |
| Soybean 1 | 5 | 0 | 5 | 0 | 0 | 5 | 0 | — | 0 | 5 | 0 | 10 | 5 | 0 | 5 | 0 | 0 |
| Surinam grass | 45 | 10 | 5 | 10 | 10 | 5 | 5 | 20 | 65 | 20 | 10 | 30 | 20 | 10 | 10 | 20 | 15 |
| Velvetleaf | 75 | 50 | 20 | 10 | 40 | 50 | 0 | 50 | 50 | 90 | 80 | 75 | 60 | 20 | 60 | 100 | 40 |

TABLE D-continued

| | | | | | | | | | | | | | | | | | |
|---|---|---|---|---|---|---|---|---|---|---|---|---|---|---|---|---|---|
| Wild poinsettia | 15 | 30 | 5 | 10 | — | 30 | 0 | 10 | 10 | 20 | 25 | 70 | 40 | 10 | 10 | 10 | 10 |

| | COMPOUND | | | | | | | |
|---|---|---|---|---|---|---|---|---|
| Rate 17 g/ha PREEMERGENCE | 12 | 16 | 17 | 20 | 29 | 36 | 37 | 40 |
| Arrowleaf sida | 90 | 80 | 90 | 25 | 25 | 80 | 80 | 70 |
| Barnyardgrass | 0 | 10 | 0 | 10 | 5 | 10 | 5 | 10 |
| Cocklebur | 0 | — | 0 | 0 | 0 | 0 | 0 | |
| Common ragweed | 10 | 10 | 0 | 25 | — | 30 | 10 | 10 |
| Corn 1 | 5 | 0 | 0 | 0 | 5 | 10 | 0 | 0 |
| Cotton | 10 | 0 | 0 | 10 | 20 | 5 | 10 | 0 |
| E. blacknightsh | 25 | 100 | 25 | 80 | 70 | 50 | 75 | 80 |
| Fall panicum | 20 | 25 | 10 | 20 | 10 | 70 | 50 | 50 |
| Field bindweed | 65 | 35 | 20 | 50 | 20 | 80 | 70 | 20 |
| Giant foxtail | 20 | 20 | 20 | 10 | 30 | 10 | 10 | 0 |
| H. beggarsticks | 0 | 0 | 10 | 10 | 10 | 0 | 10 | 0 |
| I. morningglory | 10 | 40 | 10 | 20 | 10 | 10 | 10 | 10 |
| Johnsongrass | 10 | 10 | 0 | 10 | 5 | 5 | 10 | 0 |
| Ladysthumb | 80 | — | — | 15 | 10 | 10 | 50 | — |
| Lambsquarters | 100 | — | 10 | 70 | 20 | 50 | 95 | 10 |
| Large crabgrass | 40 | 50 | 20 | 40 | 60 | 30 | 25 | 25 |
| Purple nutsedge | 0 | 0 | 0 | 0 | 0 | 0 | 0 | 0 |
| Redroot pigweed | 100 | — | 65 | 65 | 95 | 90 | 65 | 70 |
| Soybean 1 | 5 | 0 | 0 | 0 | 0 | 0 | 5 | 0 |
| Surinam grass | 20 | 10 | 10 | 10 | 25 | 10 | 10 | 10 |
| Velvetleaf | 30 | 0 | 10 | 50 | — | 50 | 50 | 10 |
| Wild poinsettia | 10 | 0 | 0 | 10 | 0 | 20 | 10 | 0 |

Test E

Compounds evaluated in this test were formulated in a non-phytotoxic solvent mixture which included a surfactant and applied to the soil surface before plant seedlings emerged (preemergence application) and to plants that were grown for various periods of time before treatment (postemergence application). A sandy loam soil was used for the preemergence test while a mixture of sandy loam soil and greenhouse potting mix in a 60:40 ratio was used for the postemergence test. Test compounds were applied within approximately one day after planting seeds for the preemergence test, and 13 days after the last postemergence planting.

Plantings of these crops and weed species were adjusted to produce plants of appropriate size for the postemergence test. All plant species were grown using normal greenhouse practices. Crop and weed species include alexandergrass (*Brachiaria plantaginea*), black nightshade (*Solanum americanum*), apple-of-Peru (*Nicandra physaloides*), arrowleaf sida (*Sida rhombzfolia*), Brazilian sicklepod (*Cassia tora* Brazilian), Brazilian signalgrass (*Brachiaria decumbens*), bristly starbur (*Acanthospermum hispidum*), capim-colchao (*Digitaria horizontalis*), corn (*Zea mays*), soybean 1 (*Glycine max* cv. Cristalina), hairy beggarticks (*Bidens pilosa*), slender amaranth (*Amaranthus viridis*), southern sandur (*Cenchrus echinatus*), tall morningglory (*Ipomoea purpurea*), tropical spiderwort (*Commelina benghalensis*), Soybean 2 (*Glycine max* cv. W20), Soybean 3 (*Glycine max* cv. W4-4) and wild pointsettia (*Eupohorbia heterophylla*).

Treated plants and untreated controls were maintained in a greenhouse for approximately 13 days, after which all treated plants were compared to untreated controls and visually evaluated. Plant response ratings, summarized in Table E, are based upon a 0 to 100 scale where 0 is no effect and 100 is complete control. A dash response (-) means no test result.

TABLE E

| | COMPOUND | | | | | |
|---|---|---|---|---|---|---|
| Rate 140 g/ha PREEMERGENCE | 12 | 13 | 14 | 20 | 22 | 49 |
| Alexandergrass | 80 | 70 | 60 | 85 | 60 | 10 |
| Apple-of-Peru | 100 | 100 | 90 | 100 | 90 | 5 |
| Arrowleaf sida | 100 | 100 | 100 | 100 | 90 | 80 |
| B. Signalgrass | 100 | 70 | 50 | 70 | 80 | 10 |
| Blk nightshade | 100 | 100 | 100 | 100 | 100 | 90 |
| Braz sicklepod | 50 | 80 | 70 | 90 | 60 | 0 |
| Bristly starbur | 100 | 60 | 90 | 100 | 100 | 0 |
| Capim-Colch | 100 | 100 | 90 | 100 | 60 | 70 |
| Corn | 10 | 5 | 5 | 5 | 5 | 20 |
| H. beggarticks | 0 | 100 | 90 | 100 | 100 | 0 |
| Morningglory | 80 | 70 | 70 | 40 | 60 | 40 |
| S. amaranth | 100 | 100 | 100 | 100 | 100 | 100 |
| S. sandbur | 80 | 75 | 50 | 50 | 60 | 5 |
| Soybean 1 | 70 | 40 | 35 | 25 | 60 | 5 |
| Soybean 2 | 50 | 10 | 10 | 60 | 45 | 5 |
| Soybean 3 | 80 | 20 | 10 | 10 | 70 | 10 |
| Tr. Spiderwort | 100 | 100 | 85 | 95 | 90 | 0 |
| Wild poinsettia | 100 | 90 | 50 | 60 | 70 | 100 |

| | COMPOUND | | | | | |
|---|---|---|---|---|---|---|
| Rate 70 g/ha PREEMERGENCE | 12 | 13 | 14 | 20 | 22 | 49 |
| Alexandergrass | 60 | 40 | 30 | 10 | 60 | 0 |
| Apple-of-Peru | 100 | 90 | 70 | 100 | 80 | 0 |
| Arrowleaf sida | 100 | 100 | 90 | 100 | — | 80 |
| B. Signalgrass | 60 | 40 | 20 | 50 | 40 | 0 |
| Blk nightshade | 100 | 100 | 100 | 100 | 90 | 80 |
| Braz sicklepod | 40 | 10 | 5 | 40 | — | 0 |
| Bristly starbur | 5 | — | 40 | 100 | 40 | 0 |
| Capim-Colch | 90 | 90 | 90 | 100 | 60 | 70 |
| Corn | 5 | 5 | 0 | 0 | 0 | 5 |
| H. beggarticks | 0 | 100 | 10 | 90 | 100 | 0 |
| Morningglory | 40 | 50 | 10 | 40 | 50 | 5 |
| S. amaranth | 100 | 100 | 100 | 100 | 100 | 100 |
| S. sandbur | 75 | 40 | 5 | 30 | — | 0 |
| Soybean 1 | 35 | 30 | 15 | 25 | 50 | 0 |

TABLE E-continued

| | | | | | | |
|---|---|---|---|---|---|---|
| Soybean 2 | 40 | 5 | 10 | 15 | 5 | 5 |
| Soybean 3 | 50 | 15 | 5 | 10 | 10 | 0 |
| Tr. Spiderwort | 80 | 100 | 60 | 95 | 90 | 0 |
| Wild poinsettia | 100 | 50 | 10 | 30 | — | 5 |

| COMPOUND | | | | | | |
|---|---|---|---|---|---|---|
| Rate 35 g/ha PREEMERGENCE | 12 | 13 | 14 | 20 | 22 | 49 |
| Alexandergrass | 60 | 30 | 20 | 10 | 0 | 0 |
| Apple-of-Peru | 10 | 80 | 5 | 90 | 80 | 0 |
| Arrowleaf sida | 90 | 80 | 85 | 90 | 80 | 0 |
| B. Signalgrass | 30 | 5 | 5 | 5 | 10 | 0 |
| Blk nightshade | 100 | 100 | 90 | 90 | 90 | 50 |
| Braz sicklepod | 0 | 0 | 0 | 5 | 20 | 0 |
| Bristly starbur | 5 | 0 | 0 | 90 | — | — |
| Capim-Colch | 90 | 80 | 50 | 90 | 10 | 60 |
| Corn | 0 | 0 | 0 | 0 | 0 | 0 |
| H. beggarticks | 0 | 50 | 0 | 100 | 0 | 0 |
| Morningglory | 5 | 50 | 5 | 10 | 50 | 0 |
| S. amaranth | 100 | 100 | 90 | 100 | 85 | 80 |
| S. sandbur | 20 | 5 | 0 | 10 | 0 | 0 |
| Soybean 1 | 10 | 10 | 5 | 10 | 10 | 0 |
| Soybean 2 | 5 | 5 | 5 | 15 | 5 | 0 |
| Soybean 3 | 10 | 10 | 5 | 5 | 5 | 0 |
| Tr. Spiderwort | 20 | 10 | 0 | 20 | 40 | 0 |
| Wild poinsettia | 5 | 5 | — | 30 | 40 | 0 |

| COMPOUND | | | | | | |
|---|---|---|---|---|---|---|
| Rate 17 g/ha PREEMERGENCE | 12 | 13 | 14 | 20 | 22 | 49 |
| Alexandergrass | 5 | 0 | 0 | 0 | 0 | 0 |
| Apple-of-Peru | — | 0 | 0 | 85 | 80 | 0 |
| Arrowleaf sida | 85 | 70 | 80 | 70 | 50 | 0 |
| B. Signalgrass | 5 | 0 | 0 | 0 | — | 0 |
| Blk nightshade | 85 | 85 | 80 | 90 | 80 | 10 |
| Braz sicklepod | — | 0 | 0 | 5 | 20 | 0 |
| Bristly starbur | — | 0 | 0 | 85 | 20 | 0 |
| Capim-Colch | 50 | 40 | 20 | 80 | — | 0 |
| Corn | 0 | 0 | 0 | 0 | 0 | 0 |
| H. beggarticks | 0 | — | 0 | 0 | 0 | 0 |
| Morningglory | 0 | 0 | 0 | 5 | 5 | 0 |
| S. amaranth | 100 | 60 | 90 | 60 | 80 | 70 |
| S. sandbur | 0 | 0 | 0 | 0 | 0 | 0 |
| Soybean 1 | 5 | 5 | 0 | 10 | 10 | 0 |
| Soybean 2 | 5 | 5 | 0 | 5 | 5 | 0 |
| Soybean 3 | 0 | 10 | 0 | 5 | 5 | 0 |
| Tr. Spiderwort | 5 | 0 | 0 | 0 | — | 0 |
| Wild poinsettia | 5 | 5 | 5 | 10 | 40 | 0 |

TEST F

Seeds, tubers, or plant parts of alexandergrass (*Brachiaria plantaginea*), broadleaf signalgrass (*Brachiaria decumbens*), bermudagrass (*Cynodon dactylon*), common purslane (*Portulaca oleracea*), common ragweed (*Ambrosia elatior*), common groundsel (*Senecio vulgaris*), dallisgrass (*Paspalum dilatatum*), goosegrass (*Eleusine indica*), guineagrass (*Panicum maximum*), itchgrass (*Rottboellia exaltata*), johnson grass (*Sorghum halepense*), large crabgrass (*Digitaria sanguinalis*), pitted morningglory (*Ipomoea lacunosa*), peanuts (*Arachis hypogaea*), purple nutsedge (*Cyperus rotundus*), sandbur (*Cenchrus echinatus*), sourgrass (*Trichachne insularis*), Spanishneedles (*Bidens bipinnata*), sugarcane (*Sacchanim officinarum*), surinam grass (*Brachiaria decumbens*) and tall mallow (*Malva sylvestris*) were planted into greenhouse pots of flats containing greenhouse planting medium. Plant species were grown grown in separate pots or individual compartments. Preemergence applications were made within one day of planting the seed or plant part. Postemergence applications were applied when the plants were in the two to four leaf stage (three to twenty cm).

Test chemicals were formulated in a non-phytotoxic solvent mixture which included a surfactant and applied preemergence and postemergeilce to the plants. Untreated control plants and treated plants were placed in the greenhouse and visually evaluated for injury 13 to 21 days after herbicide application. Plant response ratings, summarized in Table F, are based on a 0 to 100 scale where 0 is no injury and 100 is complete control. A dash (-) response means no test result.

TABLE F

| | COMPOUND | | | | COMPOUND | | | |
|---|---|---|---|---|---|---|---|---|
| Rate 1000 g/ha POST DIRECTED | 13 | | | | Rate 500 g/ha PREEMERGENCE | 12 | 13 | 19 | 20 |
| Citrus | 0 | | | | A. bluegrass | — | — | — | — |
| | | | | | Alexandergrass | 100 | — | 100 | 100 |
| | | | | | Arrowleaf sida | — | — | — | — |
| | COMPOUND | | | | B. signalgrass | — | — | — | — |
| Rate 500 g/ha POSTEMERGENCE | 12 | 13 | 19 | 20 | Barnyardgrass | — | — | — | — |
| | | | | | Bermudagrass | 100 | — | 100 | 100 |
| Alexandergrass | 100 | — | 100 | 90 | C. purslane | 100 | — | 100 | 100 |
| B. signalgrass | — | — | — | — | C. ragweed | 100 | — | 100 | 100 |
| Bermudagrass | 50 | — | 10 | 40 | Com. chickweed | — | — | — | — |
| C. purslane | 75 | — | 75 | 70 | Com. groundsel | 100 | — | 100 | 100 |
| C. ragweed | 100 | — | 75 | 90 | Cotton | — | — | — | — |
| Com. groundsel | 40 | — | 30 | 100 | Dallisgrass | 100 | — | 100 | 100 |
| Dallisgrass | — | — | 65 | 85 | Goosegrass | 100 | — | 100 | 100 |
| Goosegrass | 90 | — | 75 | 90 | Green foxtail | — | — | — | — |
| Guineagrass | 95 | — | 70 | 85 | Guineagrass | — | — | — | — |
| Itchgrass | 90 | — | 65 | 75 | Itchgrass | 98 | — | 90 | 100 |
| Johnsongrass | 90 | — | 75 | 90 | Johnsongrass | 100 | — | 70 | 100 |
| Large crabgrass | 80 | — | 70 | 85 | Kochia | — | — | — | — |
| P. morninglory | 90 | — | 75 | 90 | Large crabgrass | 100 | — | 100 | 100 |
| Peanuts | — | — | — | — | Leafy spurge | — | — | — | — |

TABLE F-continued

| | | | | | | | | | |
|---|---|---|---|---|---|---|---|---|---|
| Purple nutsedge | 0 | — | 0 | 5 | P. morninglory | 100 | — | 80 | 100 |
| Sandbur | — | — | 10 | 70 | Peanuts | — | — | — | — |
| Sourgrass | 40 | — | 75 | 60 | Purple nutsedge | 10 | — | 0 | 0 |
| Spanishneedles | 20 | — | 30 | 50 | Quackgrass | — | — | — | — |
| Sugarcane | — | 20 | — | — | Sandbur | 100 | — | 50 | 100 |
| Surinam grass | 90 | — | 75 | 80 | Sourgrass | 100 | — | 100 | 100 |
| Tall Mallow | 100 | — | 95 | 100 | Spanishneedles | 100 | — | 100 | 100 |
| | | | | | Sugarcane | — | 100 | — | — |
| | | | | | Surinam grass | 100 | — | 98 | 100 |
| | | | | | Tall Mallow | 100 | — | 100 | 100 |

COMPOUND

| Rate 250 g/ha POSTEMERGENCE | 12 | 13 | 16 | 17 | 19 | 20 | 23 | 25 | 35 | 36 | 37 | 49 | 50 | 56 |
|---|---|---|---|---|---|---|---|---|---|---|---|---|---|---|
| Alexandergrass | 90 | 75 | 85 | 40 | 30 | 50 | 25 | 80 | 30 | 95 | 90 | 10 | 20 | 80 |
| B. signalgrass | — | 80 | — | — | — | — | — | — | 30 | 40 | 40 | — | — | 10 |
| Bermudagrass | 40 | 10 | 20 | 10 | 10 | 40 | 10 | 30 | 30 | 40 | 40 | 0 | 20 | 10 |
| C. purslane | 75 | 100 | 30 | 20 | 75 | 70 | 25 | 75 | 70 | 65 | 70 | 10 | 25 | 75 |
| C. ragweed | 75 | 65 | 80 | 75 | — | 70 | 30 | 50 | 100 | 65 | 50 | 70 | 45 | 40 |
| Com. groundsel | 40 | — | 80 | 100 | 0 | 90 | 70 | 80 | 60 | 80 | 85 | 10 | 70 | 95 |
| Dallisgrass | 90 | 10 | 80 | 90 | 65 | 75 | 65 | 80 | 95 | 80 | 95 | 30 | 80 | 75 |
| Goosegrass | 90 | 20 | 80 | 90 | — | 90 | 10 | 90 | 95 | 90 | 90 | 10 | 30 | 80 |
| Guineagrass | 80 | 95 | 70 | 70 | 20 | 75 | 75 | 65 | 40 | 80 | 80 | 50 | 40 | 30 |
| Itchgrass | 90 | 40 | 85 | 80 | 20 | 65 | 10 | 40 | 75 | 65 | 60 | 60 | 85 | 40 |
| Johnsongrass | 85 | 40 | 85 | 30 | 75 | 75 | 10 | 35 | 65 | 40 | 75 | 20 | 65 | 20 |
| Large crabgrass | 80 | 95 | 85 | 85 | 35 | 75 | 60 | 80 | 75 | 90 | 85 | 40 | 20 | 70 |
| P. morninglory | 95 | 95 | 85 | 80 | 65 | 80 | 40 | 85 | 90 | 90 | 90 | 50 | 75 | 80 |
| Peanuts | — | 75 | — | — | — | — | — | — | — | — | — | — | — | — |
| Purple nutsedge | 0 | 20 | 40 | 10 | 0 | 5 | 5 | 5 | 0 | 10 | 5 | 0 | 20 | 40 |
| Sandbur | 60 | 20 | 0 | 40 | 5 | 30 | 10 | 20 | 20 | 20 | 65 | 0 | 0 | 0 |
| Sourgrass | 40 | 35 | 20 | 10 | 30 | 60 | 10 | 30 | 20 | 60 | 30 | 40 | 10 | 40 |
| Spanishneedles | 20 | — | 20 | 20 | 10 | 40 | 10 | 60 | 35 | 70 | 65 | 10 | 10 | 40 |
| Sugarcane | — | 25 | — | — | — | — | — | — | — | — | — | — | — | — |
| Surinam grass | 75 | 85 | 70 | 40 | 75 | 50 | 10 | 30 | — | 40 | 75 | 10 | 10 | 20 |
| Tall Mallow | 100 | — | 85 | 85 | 98 | 100 | 45 | 90 | 100 | 90 | 85 | 65 | 75 | 85 |

COMPOUND

| Rate 250 g/ha PREEMERGENCE | 12 | 13 | 16 | 17 | 19 | 20 | 23 | 25 | 35 | 36 | 37 | 49 | 50 | 56 |
|---|---|---|---|---|---|---|---|---|---|---|---|---|---|---|
| A. bluegrass | 100 | — | — | — | — | 100 | — | — | — | 100 | 100 | — | — | 100 |
| Alexandergrass | 100 | 100 | 100 | 80 | 65 | 100 | 95 | 100 | 100 | 100 | 100 | 30 | 30 | — |
| Arrowleaf sida | 100 | 100 | — | — | — | 100 | — | — | — | 100 | 100 | — | — | 100 |
| B. signalgrass | 100 | 100 | — | — | — | 100 | — | — | — | 100 | 100 | 20 | — | 100 |
| Barnyardgrass | 100 | 98 | — | — | — | 100 | — | — | — | 100 | 100 | — | — | 90 |
| Bermudagrass | 100 | 100 | 100 | 100 | 100 | 100 | 100 | 100 | 100 | 100 | 100 | 98 | 100 | — |
| C. purslane | 100 | 100 | 100 | 100 | 100 | 100 | 100 | 100 | 100 | 100 | 100 | 100 | 100 | 100 |
| C. ragweed | 100 | 100 | 100 | 100 | 100 | 100 | 100 | 100 | 100 | 100 | 100 | 95 | 100 | — |
| Com. chickweed | 100 | 100 | — | — | — | 100 | — | — | — | 100 | 100 | — | — | 100 |
| Com. groundsel | 100 | 100 | 100 | 100 | 75 | 100 | 100 | 100 | 100 | 100 | 100 | 0 | 100 | — |
| Cotton | — | 90 | — | — | — | — | — | — | — | — | — | 0 | — | — |
| Dallisgrass | 100 | 100 | 100 | 100 | 95 | 100 | 100 | 100 | 100 | 100 | 100 | 70 | 95 | — |
| Goosegrass | 100 | 100 | 100 | 100 | 100 | 100 | 100 | 100 | 100 | 100 | 100 | 98 | 100 | 100 |
| Green foxtail | 100 | 100 | — | — | — | 100 | — | — | — | 100 | 100 | — | — | 100 |
| Guineagrass | — | 100 | 100 | 100 | — | — | 100 | 100 | — | 100 | 100 | 100 | 50 | — |
| Itchgrass | 100 | 60 | 90 | 60 | 80 | 100 | 75 | 75 | 95 | 85 | 95 | 30 | 65 | — |
| Johnsongrass | 100 | 70 | 80 | 100 | 50 | 98 | 65 | 15 | 100 | 100 | 100 | 20 | 60 | — |
| Kochia | 100 | 100 | — | — | — | 100 | — | — | — | 100 | 100 | — | — | 100 |
| Large crabgrass | 100 | 100 | 100 | 100 | 100 | 100 | 100 | 100 | 100 | 100 | 100 | 98 | 90 | 100 |
| Leafy spurge | 100 | 100 | — | — | — | 100 | — | — | — | 100 | 100 | — | — | 100 |
| P. morninglory | 100 | 95 | 100 | 90 | 80 | 100 | 90 | 100 | 100 | 98 | 98 | 10 | 100 | 100 |
| Peanuts | — | 10 | — | — | — | — | — | — | — | — | — | 0 | — | — |
| Purple nutsedge | 0 | 20 | 20 | 0 | 10 | 0 | 0 | 20 | 0 | 0 | 0 | 0 | 20 | 75 |
| Quackgrass | 100 | 98 | — | — | — | 100 | — | — | — | 100 | 100 | — | — | 100 |
| Sandbur | 100 | 80 | 100 | 50 | 30 | 160 | 65 | 50 | 90 | 100 | 100 | 0 | 20 | 80 |
| Sourgrass | 100 | 100 | 100 | 100 | 100 | 100 | 100 | 100 | 100 | 100 | 100 | 100 | 100 | — |
| Spanishneedles | 100 | 100 | 90 | 100 | 50 | 100 | 100 | 100 | 100 | 100 | 100 | 30 | 100 | — |
| Sugarcane | — | 15 | — | — | — | — | — | — | — | — | — | — | — | — |
| Surinam grass | 100 | 100 | 100 | 98 | 90 | 100 | 85 | 100 | 100 | 100 | 100 | 10 | 20 | 75 |
| Tall Mallow | 100 | 100 | 100 | 100 | 100 | 100 | 100 | 100 | 100 | 100 | 100 | 100 | 98 | — |

COMPOUND

| Rate 125 g/ha POSTEMERGENCE | 12 | 13 | 19 | 20 | 25 | 35 | 36 | 37 | 49 | 56 |
|---|---|---|---|---|---|---|---|---|---|---|

TABLE F-continued

| | | | | | | | | | | | | | |
|---|---|---|---|---|---|---|---|---|---|---|---|---|---|
| Alexandergrass | 80 | 20 | 30 | 20 | 20 | 30 | 30 | 50 | 40 | 30 | | | |
| B. signalgrass | — | 50 | — | — | — | — | — | — | 20 | | | | |
| Bermudagrass | 30 | 10 | 10 | 30 | 10 | 30 | 20 | 20 | 10 | 10 | | | |
| C. purslane | 65 | 90 | 75 | 70 | 60 | 70 | 65 | 60 | 100 | 60 | | | |
| C. ragweed | 75 | 100 | 40 | 70 | 50 | 65 | 35 | 35 | 100 | 30 | | | |
| Com. groundsel | 35 | — | 0 | 80 | 30 | 60 | 75 | 75 | — | 80 | | | |
| Dallisgrass | 80 | 10 | 65 | 40 | 20 | 50 | 75 | 75 | 0 | 70 | | | |
| Goosegrass | 90 | 0 | — | 75 | 90 | 65 | 60 | 85 | 30 | 70 | | | |
| Guineagrass | 80 | 30 | 10 | 30 | 40 | 20 | 80 | 75 | 50 | 40 | | | |
| Itchgrass | 60 | 20 | 20 | 65 | 10 | 75 | 35 | 35 | 20 | 10 | | | |
| Johnsongrass | 75 | 35 | 40 | 75 | 10 | 65 | 35 | 40 | 35 | 10 | | | |
| Large crabgrass | 80 | 60 | 35 | 75 | 80 | 30 | 30 | 75 | 65 | 70 | | | |
| P. morninglory | 95 | 100 | 50 | 80 | 85 | 90 | 85 | 85 | 85 | 85 | | | |
| Peanuts | — | 50 | — | — | — | — | — | — | 70 | — | | | |
| Purple nutsedge | 0 | 10 | 0 | 0 | 0 | 0 | 0 | 5 | 0 | 0 | | | |
| Sandbur | 40 | 0 | 0 | 20 | 20 | 10 | 5 | 40 | 0 | 0 | | | |
| Sourgrass | 20 | 20 | 30 | 35 | 30 | 20 | 35 | 30 | 20 | 35 | | | |
| Spanishneedles | 20 | — | 10 | 40 | 40 | 5 | 40 | 50 | — | 30 | | | |
| Sugarcane | — | 20 | — | — | — | — | — | — | — | — | | | |
| Surinam grass | 65 | 65 | 30 | 35 | 30 | 70 | 35 | 35 | 65 | 10 | | | |
| Tall Mallow | 100 | — | 98 | 100 | 80 | 100 | 90 | 85 | — | 98 | | | |

| | COMPOUND | | | | | | | | | | | | |
|---|---|---|---|---|---|---|---|---|---|---|---|---|---|
| Rate 125 g/ha PREEMERGENCE | 12 | 13 | 16 | 17 | 19 | 20 | 23 | 25 | 35 | 36 | 37 | 49 | 50 | 56 |
| A. bluegrass | 100 | — | — | — | — | 100 | — | — | — | 100 | 100 | — | — | 100 |
| Alexandergrass | 100 | 75 | 100 | 50 | 0 | 100 | 75 | 80 | 100 | 100 | 100 | 90 | 10 | — |
| Arrowleaf sida | 100 | 95 | — | — | — | 100 | — | — | — | 100 | 100 | — | — | 100 |
| B. signalgrass | 100 | 90 | — | — | — | 100 | — | — | — | 100 | 100 | 100 | — | 100 |
| Barnyardgrass | 90 | 80 | — | — | — | 95 | — | — | — | 100 | 100 | — | — | 80 |
| Bermudagrass | 100 | 100 | 100 | 100 | 98 | 100 | 100 | 100 | 100 | 100 | 100 | 100 | 100 | — |
| C. purslane | 100 | 100 | 100 | 100 | 100 | 100 | 100 | 100 | 100 | 100 | 100 | 100 | 100 | 100 |
| C. ragweed | 100 | 100 | 100 | 100 | 65 | 100 | 100 | 100 | 100 | 100 | 100 | 100 | 100 | — |
| Com. chickweed | 100 | 100 | — | — | — | 100 | — | — | — | 100 | 100 | — | — | 100 |
| Com. groundsel | 100 | 100 | 98 | 100 | 75 | 100 | 100 | 100 | 100 | 100 | 100 | 0 | 100 | — |
| Cotton | — | 40 | — | — | — | — | — | — | — | — | — | 40 | — | — |
| Dallisgrass | 100 | 100 | 100 | 100 | 80 | 100 | 100 | 100 | 100 | 100 | 100 | 100 | 70 | — |
| Goosegrass | 100 | 100 | 100 | 100 | 100 | 100 | 100 | 100 | 100 | 100 | 100 | 100 | 100 | 100 |
| Green foxtail | 100 | 100 | — | — | — | 100 | — | — | — | 100 | 100 | — | — | 100 |
| Guineagrass | — | 100 | 100 | 98 | — | — | 100 | 100 | — | 100 | 100 | 100 | 20 | — |
| Itchgrass | 95 | 20 | 60 | 40 | 30 | 100 | 40 | 5 | 70 | 75 | 80 | 65 | 40 | — |
| Johnsongrass | 100 | 0 | 40 | 100 | 20 | 80 | 30 | 5 | 50 | 30 | 100 | 50 | 30 | — |
| Kochia | 100 | 100 | — | — | — | 100 | — | — | — | 100 | 100 | — | — | 100 |
| Large crabgrass | 100 | 100 | 100 | 100 | 100 | 100 | 100 | 100 | 100 | 100 | 100 | 100 | 90 | 100 |
| Leafy spurge | 100 | 100 | — | — | — | 100 | — | — | — | 100 | 100 | — | — | 100 |
| P. morninglory | 100 | 75 | 100 | 90 | 80 | 100 | 98 | 100 | 100 | 100 | 98 | 80 | 80 | 100 |
| Peanuts | — | 10 | — | — | — | — | — | — | — | — | — | 0 | — | — |
| Purple nutsedge | 0 | 0 | 20 | 0 | 10 | 0 | 0 | 0 | 0 | 0 | 0 | 30 | — | 10 |
| Quackgrass | 100 | 95 | — | — | — | 100 | — | — | — | 100 | 100 | — | — | 100 |
| Sandbur | 100 | 10 | 100 | 10 | 10 | 100 | 40 | 10 | 75 | 90 | 60 | 40 | 0 | 60 |
| Sourgrass | 100 | 100 | 100 | 100 | 100 | 100 | 100 | 100 | 100 | 100 | 100 | 100 | 100 | — |
| Spanishneedles | 90 | 100 | 70 | 80 | 30 | 100 | 80 | 100 | 100 | 100 | 100 | 0 | 50 | — |
| Sugarcane | — | 15 | — | — | — | — | — | — | — | — | — | — | — | — |
| Surinam grass | 100 | 75 | 100 | 40 | 10 | 100 | 85 | 100 | 95 | 100 | 100 | 100 | 0 | 65 |
| Tall Mallow | 100 | 100 | 100 | 100 | 100 | 100 | 100 | 100 | 100 | 100 | 100 | 100 | 100 | — |

| | COMPOUND | | | | | |
|---|---|---|---|---|---|---|
| Rate 64 g/ha POSTEMERGENCE | 12 | 13 | 19 | 20 | 35 | 49 |
| Alexandergrass | 90 | 20 | 20 | — | 10 | 10 |
| B. signalgrass | — | 20 | — | — | — | 10 |
| Bermudagrass | 20 | 10 | 10 | 20 | 20 | 10 |
| C. purslane | 65 | 90 | 50 | 70 | 70 | 100 |
| C. ragweed | 50 | 100 | 30 | 50 | — | 10 |
| Com. groundsel | 20 | — | 0 | 65 | — | — |
| Dallisgrass | 35 | 10 | 20 | 20 | 20 | 0 |
| Goosegrass | 80 | 0 | 75 | 75 | 65 | 30 |
| Guineagrass | 30 | 10 | 10 | 30 | — | 35 |
| Itchgrass | 40 | 10 | 10 | 20 | 75 | 20 |
| Johnsongrass | 40 | 5 | 20 | 65 | 35 | 35 |
| Large crabgrass | 50 | 30 | 10 | 50 | 20 | 20 |
| P. morninglory | 90 | 95 | 60 | 80 | 80 | 85 |
| Peanuts | — | 65 | — | — | — | 50 |
| Purple nutsedge | 0 | 10 | 0 | 0 | 0 | 0 |
| Sandbur | 0 | 0 | 0 | 10 | 0 | 0 |

TABLE F-continued

| | | | | | | |
|---|---|---|---|---|---|---|
| Sourgrass | 10 | 10 | 30 | 20 | — | 20 |
| Spanishneedles | 5 | — | 10 | 50 | 5 | — |
| Sugarcane | — | 20 | — | — | — | — |
| Surinam grass | 65 | 0 | 30 | 35 | 70 | 35 |
| Tall Mallow | 100 | — | 95 | 100 | 100 | — |

| | COMPOUND | | | | | | | | | | | | |
|---|---|---|---|---|---|---|---|---|---|---|---|---|---|
| Rate 64 g/ha PREEMERGENCE | 12 | 13 | 16 | 17 | 19 | 20 | 23 | 25 | 35 | 36 | 37 | 49 | 50 | 56 |
| A. bluegrass | 100 | — | — | — | — | 95 | — | — | — | 100 | 100 | — | — | 98 |
| Alexandergrass | 100 | 70 | 80 | 10 | 0 | 100 | 30 | 50 | 65 | 100 | 80 | 75 | 0 | 100 |
| Arrowleaf sida | 100 | 95 | — | — | — | 100 | — | — | — | 100 | 100 | — | — | 100 |
| B. signalgrass | 100 | 65 | — | — | — | 98 | — | — | — | 100 | 100 | 90 | — | 85 |
| Barnyardgrass | 35 | 65 | — | — | — | 25 | — | — | — | 80 | 98 | — | — | 40 |
| Bermudagrass | 100 | 98 | 100 | 100 | 90 | 100 | 100 | 100 | 100 | 100 | 100 | 100 | 95 | 100 |
| C. purslane | 100 | 100 | 100 | 100 | 100 | 100 | 100 | 100 | 100 | 100 | 100 | 100 | 100 | 100 |
| C. ragweed | 100 | 100 | 98 | 95 | 0 | 98 | 98 | 100 | 100 | 100 | 100 | 100 | 100 | 100 |
| Com. chickweed | 100 | 100 | — | — | — | 100 | — | — | — | 98 | 100 | — | — | 100 |
| Com. groundsel | 100 | 100 | 100 | 100 | 0 | 100 | 100 | 100 | 100 | 100 | 100 | 0 | 95 | 95 |
| Cotton | — | 40 | — | — | — | — | — | — | — | — | — | 15 | — | — |
| Dallisgrass | 100 | 90 | 100 | 60 | 20 | 100 | 80 | — | 100 | 100 | 100 | 98 | 50 | 100 |
| Goosegrass | 100 | 100 | 100 | 90 | 100 | 100 | 100 | 100 | 100 | 100 | 100 | 100 | 95 | 100 |
| Green foxtail | 100 | 100 | — | — | — | 100 | — | — | 100 | 100 | — | — | 100 | |
| Guineagrass | — | 100 | 100 | 90 | — | — | 80 | 80 | — | 100 | 100 | 100 | 20 | 100 |
| Itchgrass | 100 | 35 | 35 | 10 | — | 75 | 20 | 5 | 5 | 10 | 80 | 50 | 20 | 10 |
| Johnsongrass | 40 | 20 | 10 | 100 | 0 | 40 | 30 | 5 | 20 | 5 | 10 | 35 | 10 | 5 |
| Kochia | 100 | 100 | — | — | — | 100 | — | — | — | 100 | 100 | — | — | 100 |
| Large crabgrass | 100 | 100 | 100 | 90 | 100 | 100 | 100 | 100 | 100 | 100 | 100 | 100 | 30 | 100 |
| Leafy spurge | 100 | 100 | — | — | — | 100 | — | — | — | 100 | 100 | — | — | 100 |
| P. morninglory | 95 | 60 | 100 | 80 | 35 | 100 | 60 | 90 | 100 | 95 | 100 | 70 | 80 | 100 |
| Peanuts | — | 5 | — | — | — | — | — | — | — | — | — | 0 | — | — |
| Purple nutsedge | 0 | 20 | 0 | 0 | 0 | 0 | 0 | 0 | 0 | 0 | 0 | 35 | 0 | 20 |
| Quackgrass | 98 | 50 | — | — | — | 100 | — | — | — | 100 | 100 | — | — | 90 |
| Sandbur | 35 | 20 | 50 | 10 | 0 | 75 | 20 | 5 | 20 | 30 | 60 | 35 | 0 | 10 |
| Sourgrass | 100 | 100 | 100 | 95 | 0 | 100 | 100 | 100 | 100 | 100 | 100 | 100 | 98 | 100 |
| Spanishneedles | 75 | 60 | 50 | 70 | 30 | 100 | 70 | 100 | 100 | 100 | 100 | 0 | 20 | 80 |
| Sugarcane | — | 10 | — | — | — | — | — | — | — | — | — | — | — | — |
| Surinam grass | 85 | 75 | 90 | 65 | 10 | 90 | 20 | 80 | 60 | 100 | 100 | 80 | 0 | 0 |
| Tall Mallow | 100 | 100 | 100 | 100 | 100 | 100 | 98 | 100 | 100 | 100 | 100 | 100 | 100 | 100 |

| | COMPOUND | | | | COMPOUND | | |
|---|---|---|---|---|---|---|---|
| Rate 32 g/ha POSTEMERGENCE | 12 | 19 | 20 | Rate 32 g/ha POSTEMERGENCE | 12 | 19 | 20 |
| Alexandergrass | 40 | 0 | 20 | Johnsongrass | 20 | 20 | 65 |
| B. signalgrass | — | — | — | Large crabgrass | 20 | 10 | 40 |
| Bermudagrass | 10 | 0 | 20 | P. morninglory | 65 | 60 | 80 |
| C. purslane | 65 | 50 | 70 | Peanuts | — | — | — |
| C. ragweed | 50 | 30 | 50 | Purpie nutsedge | 0 | 0 | 0 |
| Com. groundsel | 20 | 0 | 0 | Sandbur | 0 | 0 | 5 |
| Dallisgrass | 35 | 20 | 10 | Sourgrass | 10 | 20 | 20 |
| Goosegrass | 75 | 70 | 75 | Spanishneedles | 5 | 10 | 35 |
| Guineagrass | 20 | 0 | 10 | Sugarcane | — | — | — |
| Itchgrass | 20 | 5 | 20 | Surinam grass | 65 | 30 | 20 |
| | | | | Tall Mallow | 90 | 75 | 80 |

| | COMPOUND | | | | | | | | | | | | |
|---|---|---|---|---|---|---|---|---|---|---|---|---|---|
| Rate 32 g/ha PREEMERGENCE | 12 | 13 | 16 | 17 | 19 | 20 | 23 | 25 | 36 | 37 | 49 | 50 | 56 |
| A. bluegrass | 98 | — | — | — | — | 100 | — | — | 100 | 80 | — | — | 80 |
| Alexandergrass | 75 | 10 | 30 | 0 | 0 | 50 | 10 | 35 | 75 | — | 0 | 0 | 35 |
| Arrowleaf sida | 100 | 90 | — | — | — | 100 | — | — | 100 | 100 | — | — | 100 |
| B. signalgrass | 85 | 0 | — | — | — | 80 | — | — | 100 | 100 | 0 | — | 75 |
| Barnyardgrass | 5 | 20 | — | — | — | 10 | — | — | 30 | 20 | — | — | 35 |
| Bermudagrass | 100 | 60 | 100 | 90 | 60 | 100 | 100 | 100 | 100 | 100 | 10 | 75 | 100 |
| C. purslane | 100 | 100 | 100 | 100 | 100 | 100 | 100 | 100 | 100 | 100 | 80 | 100 | 100 |
| C. ragweed | 100 | 60 | 90 | 90 | 0 | 98 | 98 | 90 | 75 | 100 | 90 | 98 | 90 |
| Com. chickweed | 95 | 65 | — | — | — | 100 | — | — | 100 | 98 | — | — | 100 |
| Com. groundsel | 98 | 100 | 75 | 100 | 0 | 100 | 100 | 100 | 100 | 100 | 0 | 75 | 50 |
| Cotton | — | 0 | — | — | — | — | — | — | — | — | 0 | — | — |
| Dallisgrass | 80 | 60 | 100 | 70 | 0 | 98 | 30 | 80 | 90 | 100 | 0 | 20 | 65 |
| Goosegrass | 100 | 98 | 100 | 80 | 0 | 100 | 100 | 100 | 100 | 100 | 80 | 50 | 100 |
| Green foxtail | 100 | 100 | — | — | — | 100 | — | — | 100 | 100 | — | — | 100 |
| Guineagrass | — | 80 | 90 | 60 | — | — | 70 | 70 | 75 | 100 | 20 | — | 85 |

TABLE F-continued

| | | | | | | | | | | | | |
|---|---|---|---|---|---|---|---|---|---|---|---|---|
| Itchgrass | 40 | 0 | 20 | 20 | — | 75 | 20 | 5 | 0 | 65 | 0 | 20 | — |
| Johnsongrass | 30 | 0 | 10 | 100 | 0 | — | 10 | 5 | 5 | 10 | 0 | 10 | 5 |
| Kochia | 100 | 98 | — | — | — | 100 | — | — | 100 | 100 | — | — | 100 |
| Large crabgrass | 100 | 30 | 100 | 80 | 0 | 100 | 35 | 80 | 100 | 100 | 0 | 20 | 85 |
| Leafy spurge | 100 | 75 | — | — | — | 100 | — | — | 100 | 100 | — | — | 100 |
| P. morninglory | 100 | 10 | 80 | 0 | 35 | 100 | 40 | 100 | 25 | 100 | 0 | 65 | 70 |
| Peanuts | — | 0 | — | — | — | — | — | — | — | — | 0 | — | — |
| Purple nutsedge | 0 | 0 | 0 | 0 | 0 | 0 | 0 | 0 | 0 | 0 | 0 | 0 | 0 |
| Quackgrass | 50 | 0 | — | — | — | 35 | — | — | 95 | 90 | — | — | 65 |
| Sandbur | 35 | 0 | 10 | 0 | 0 | 0 | 0 | 0 | 0 | 60 | 0 | 0 | 0 |
| Sourgrass | 98 | 98 | 100 | 90 | 0 | 100 | 90 | 100 | 100 | 100 | 40 | 98 | 100 |
| Spanishneedles | 60 | 0 | 50 | 70 | 20 | 100 | 70 | 40 | 100 | 100 | 0 | 0 | 5 |
| Sugarcane | — | 10 | — | — | — | — | — | — | — | — | — | — | — |
| Surinam grass | 75 | 10 | 35 | 20 | 10 | 50 | 10 | 40 | 10 | 100 | 0 | 0 | 0 |
| Tall Mallow | 100 | 98 | 100 | 100 | 100 | 100 | 98 | 100 | 98 | 100 | 98 | 98 | 100 |

| COMPOUND | | | | | | | | | | | | |
|---|---|---|---|---|---|---|---|---|---|---|---|---|
| Rate 16 g/ha PREEMERGENCE | 12 | 13 | 16 | 17 | 20 | 23 | 25 | 36 | 37 | 49 | 50 | 56 |
| A. bluegrass | 35 | — | — | — | 50 | — | — | 80 | 80 | — | — | 20 |
| Alexandergrass | — | 0 | 0 | 0 | — | 0 | 10 | — | — | 0 | 0 | 0 |
| Arrowleaf sida | 95 | 75 | — | — | 100 | — | — | 98 | 98 | — | — | 95 |
| B. signalgrass | 20 | 0 | — | — | 20 | — | — | 90 | 90 | 0 | — | 5 |
| Barnyardgrass | 5 | 20 | — | — | 0 | — | — | 20 | 10 | — | — | 5 |
| Bermudagrass | — | 40 | 100 | 75 | — | 80 | 10 | — | — | 0 | 70 | 98 |
| C. purslane | 100 | 98 | 100 | 100 | 100 | 100 | 100 | 100 | 100 | 40 | 95 | 100 |
| C. ragweed | — | — | 65 | — | — | 90 | 0 | — | — | 25 | 0 | 95 |
| Com. chickweed | 95 | 20 | — | — | 80 | — | — | 98 | 80 | — | — | 80 |
| Com. groundsel | — | 100 | 50 | 95 | — | 100 | 95 | — | — | 0 | 20 | 0 |
| Cotton | — | 0 | — | — | — | — | — | — | — | 0 | — | — |
| Dallisgrass | — | 40 | 0 | 10 | — | 20 | 10 | — | — | 0 | 0 | 5 |
| Goosegrass | 100 | 60 | 100 | 5 | 100 | 40 | 75 | 100 | 100 | 0 | 10 | 80 |
| Green foxtail | 100 | 80 | — | — | 80 | — | — | 100 | 75 | — | — | 25 |
| Guineagrass | — | 60 | 90 | 40 | — | 30 | 0 | — | — | 0 | 0 | 100 |
| Itchgrass | — | 0 | 10 | 20 | — | 20 | 0 | — | — | 0 | 0 | 10 |
| Johnsongrass | — | 0 | 0 | 50 | — | 0 | 0 | — | — | 0 | 10 | 5 |
| Kochia | 90 | 98 | — | — | 98 | — | — | 100 | 100 | — | — | 100 |
| Large crabgrass | 90 | 30 | 70 | 5 | 75 | 5 | 35 | 100 | 50 | 0 | 0 | 35 |
| Leafy spurge | 80 | 75 | — | — | 90 | — | — | 90 | 100 | — | — | 100 |
| P. morninglory | 20 | 0 | 50 | 0 | 20 | 20 | 60 | 60 | 30 | 0 | 30 | 70 |
| Peanuts | — | — | — | — | — | — | — | — | — | 0 | — | — |
| Purple nutsedge | 0 | 0 | 0 | 0 | 0 | 0 | 0 | 0 | 0 | 0 | 0 | 0 |
| Quackgrass | 10 | 0 | — | — | 10 | — | — | 80 | 50 | — | — | 0 |
| Sandbur | 0 | 0 | 0 | 0 | 0 | 0 | 0 | 5 | 20 | 0 | 0 | 0 |
| Sourgrass | — | 30 | 100 | 0 | — | 70 | 85 | — | — | 0 | 50 | 100 |
| Spanishneedles | — | 0 | 0 | 20 | — | 0 | 30 | — | — | 0 | 0 | 5 |
| Sugarcane | — | — | — | — | — | — | — | — | — | — | — | — |
| Surinam grass | 30 | 10 | 35 | — | 30 | 0 | 5 | 10 | 70 | 0 | 0 | 0 |
| Tall Mallow | — | 98 | 100 | 90 | — | 80 | 95 | — | — | 0 | 98 | 98 |

| COMPOUND | | | | | | COMPOUND | | | | | |
|---|---|---|---|---|---|---|---|---|---|---|---|
| Rate 8 g/ha PREEMERGENCE | 12 | 20 | 36 | 37 | 56 | Rate 8 g/ha PREEMERGENCE | 12 | 20 | 36 | 37 | 56 |
| A. bluegrass | 0 | 40 | 40 | 80 | 20 | Itchgrass | — | — | — | — | 0 |
| Alexandergrass | — | — | — | — | 0 | Johnsongrass | — | — | — | — | 0 |
| Arrowleaf sida | 0 | 85 | 95 | 90 | 95 | Kochia | 65 | 100 | 98 | 100 | 90 |
| B. signalgrass | 10 | 0 | 35 | 70 | 5 | Large crabgrass | 30 | 0 | 65 | 50 | 35 |
| Barnyardgrass | 0 | 0 | 20 | 10 | 0 | Leafy spurge | 65 | 75 | 70 | 80 | 80 |
| Bermudagrass | — | — | — | — | 25 | P. morninglory | 0 | 20 | 60 | — | 30 |
| C. purslane | 75 | 100 | 100 | 100 | 85 | Peanuts | — | — | — | — | — |
| C. ragweed | — | — | — | — | 75 | Purple nutsedge | 0 | 0 | 0 | 0 | 0 |
| Com. chickweed | 20 | 60 | 20 | 70 | 0 | Quackgrass | 10 | 0 | 55 | 10 | 0 |
| Com. groundsel | — | — | — | — | — | Sandbur | 0 | 0 | 0 | 0 | 0 |
| Cotton | — | — | — | — | — | Sourgrass | — | — | — | — | 50 |
| Dallisgrass | — | — | — | — | 0 | Spanishneedles | — | — | — | — | 0 |
| Goosegrass | 65 | 10 | — | 100 | 65 | Sugarcane | — | — | — | — | — |
| Green foxtail | 95 | 50 | 85 | — | — | Surinam grass | 0 | 0 | 10 | 65 | 0 |
| Guineagrass | — | — | — | — | 60 | Tall Mallow | — | — | — | — | 100 |

Test G

Compounds evaluated in this test were formulated in a non-phytotoxic solvent mixture which included a surfactant and applied to plants that were in the 1- to 4-leaf stage (postemergence application). A mixture of sandy loam soil and greenhouse potting mix in a 60:40 ratio was used for the postemergence test.

Plantings of these crops and weed species were adjusted to produce plants of appropriate size for the postemergence test. All plant species were grown using normal greenhouse practices. Crop and weed species include alfalfa (*Medicago sativa*), annual bluegrass (*Poa annua*), blackgrass 2 (*Alopecurus myosuroides*), black nightshade (*Solanum nigra*), chickweed (*Stellaria media*), common poppy (*Papaver rhoeas*), deadnettle (*Lantium amplexicaule*), downy brome (*Bromus tectorum*), field violet (*Viola arvensis*), galium 2 (*Galium aparine*), green foxtail (*Setaria viridis*), ryegrass (*Lolium multiflorum*), jointed goatgrass (*Aegilops cylindrica*), kochia (*Kochia scoparia*), larfibsquarters (*Chlenopoditim album*), lentil (*Lens culinaris*), littleseed canarygrass (*Phialaris minor*), pea (*Pisuni salivum*), potato (*Solanum tuberosum*), rape I (*Brassica napus*), redroot pigweed (*Amaranthus retroflexus*), Russian thistle (*Salsola kali*), scentless chamomile (*Matricaria inodora*), spring barley (*Hordeum vulgare*), sugar beet (*Beta vulgaris*), sunflower (*Helianithus annuus*), ivyleaf speedwell (*Veronica hederaefolia*), spring wheat (*Triticum aestivum*), winter wheat (*Triticum aestivum*), wild buckwheat (*Polygonum convolvulus*), wild mustard (*Sinapis arvensis*), wild oat 1 (*Avena fatua*), windgrass (*Apera spicaventi*) and winter barley (*Hordeum vulgare*). Treated plants and untreated controls were maintained in a greenhouse for approximately 21 to 28 days, after which all treated plants were compared to untreated controls and visually evaluated. Plant response ratings, summarized in Table G, are based upon a 0 to 100 scale where 0 is no effect and 100 is complete control. A dash response (-) means no test result.

TABLE G

| | COMPOUND | | | COMPOUND | | | | | |
|---|---|---|---|---|---|---|---|---|---|
| Rate 250 g/ha POSTEMERGENCE | 20 | 24 | Rate 250 g/ha PREEMERGENCE | 20 | 25 | 29 | 36 | 37 | 57 |
| Annual bluegras | 60 | 50 | Alfalfa | — | — | — | — | — | — |
| Barley (winter) | 50 | 10 | Annual bluegras | 100 | 90 | 85 | 85 | 100 | 75 |
| Blackgrass (2) | 30 | 30 | Barley (winter) | 30 | 10 | 30 | 20 | 10 | 5 |
| Blk nightshade | 95 | 100 | Blackgrass (2) | 90 | 70 | 50 | 100 | 70 | 30 |
| Chickweed | 90 | 65 | Blk nightshade | 100 | 100 | 100 | 100 | 100 | 100 |
| Common poppy | 100 | 70 | Chickweed | 85 | 85 | 100 | 100 | 100 | 70 |
| Deadnettle | 95 | 70 | Common poppy | 100 | 100 | 100 | 100 | 100 | 100 |
| Downy brome | 40 | 20 | Deadnettle | 70 | 70 | 100 | 85 | 70 | — |
| Field violet | 100 | 100 | Downy brome | 100 | 85 | 20 | 100 | 100 | 30 |
| Galium (2) | 60 | 65 | Field violet | 100 | 100 | 85 | 50 | 100 | 60 |
| Green foxtail | 85 | 95 | Galium (2) | 100 | 100 | 85 | 100 | 100 | 100 |
| I. Ryegrass | 20 | 20 | Green foxtail | 100 | 100 | 100 | 100 | 100 | 100 |
| Jointed goatgrass | 30 | 30 | I. Ryegrass | 75 | 65 | 65 | 100 | 100 | 10 |
| Kochia | 75 | 70 | Jointed goatgra | 65 | 40 | 20 | 90 | 65 | 10 |
| Lambsquarters | 100 | 75 | Kochia | 85 | 100 | 100 | 100 | 100 | 100 |
| LS canarygrass | 65 | 30 | Lambsquarters | 75 | 85 | 70 | 85 | 70 | 70 |
| Rape (1) | 100 | 100 | Lentil | — | — | — | — | — | — |
| Redroot pigweed | 75 | 70 | LS canarygrass | 100 | 65 | 85 | 75 | 70 | 70 |
| Russian thistle | 80 | 65 | Pea | — | — | — | — | — | — |
| Scentless chamo | 100 | 75 | Potato | — | — | — | — | — | — |
| Spring Barley | 30 | 10 | Rape (1) | 90 | 100 | 85 | 85 | 75 | 100 |
| Sugar beet | 100 | 100 | Redroot pigweed | 100 | 85 | 100 | 100 | 85 | 75 |
| Sunflower | 60 | 60 | Russian thistle | 100 | 85 | 100 | 100 | 100 | 60 |
| Veronica hedera | — | 70 | Scentless chamo | 85 | 70 | 85 | 85 | 70 | 75 |
| Wheat (spring) | 30 | 15 | Sorghum | — | — | — | — | — | — |
| Wheat (winter) | 20 | 10 | Spring Barley | 20 | 10 | 10 | 20 | 20 | 10 |
| Wild buckwheat | 55 | 70 | Sugar beet | 100 | 100 | 100 | 100 | 100 | 70 |
| Wild mustard | 100 | 100 | Sunflower | 30 | 80 | 35 | 60 | 80 | 10 |
| Wild oat (1) | 45 | 30 | Veronica hedera | 100 | 100 | 100 | 100 | 100 | — |
| Windgrass | 60 | 60 | Wheat (spring) | 30 | 10 | 10 | 40 | 30 | 10 |
| | | | Wheat (winter) | 20 | 10 | 10 | 20 | 30 | 5 |
| | | | Wild buckwheat | 100 | 90 | 100 | 100 | 100 | 100 |
| | | | Wiid mustard | 100 | 100 | 100 | 100 | 100 | 100 |
| | | | Wild oat (1) | 90 | 60 | 75 | 85 | 90 | 20 |
| | | | Windgrass | 100 | 100 | 85 | 100 | 70 | 100 |

| | COMPOUND | | | | | | | | |
|---|---|---|---|---|---|---|---|---|---|
| Rate 125 g/ha POSTEMERGENCE | 6 | 13 | 14 | 20 | 21 | 22 | 49 | 51 | 56 |
| Annual bluegras | 20 | 50 | 60 | 40 | 50 | 70 | 50 | 30 | 65 |
| Barley (winter) | 10 | 10 | 20 | 40 | 20 | 65 | 10 | 60 | 10 |
| Blackgrass (2) | 10 | 10 | 20 | 20 | 20 | 60 | 25 | 20 | 20 |
| Blk nightshade | 80 | 100 | 100 | 100 | 75 | 90 | 100 | 70 | 100 |
| Chickweed | 30 | 65 | 60 | 85 | 50 | 70 | 100 | 60 | 70 |
| Common poppy | 50 | 85 | 100 | 100 | 70 | 100 | 100 | 70 | 100 |
| Deadnettle | 30 | 85 | 100 | 100 | 45 | 100 | 100 | 60 | 80 |
| Downy brome | 10 | 20 | 20 | 30 | 10 | 70 | 20 | 10 | 30 |
| Field violet | 100 | 100 | 100 | 100 | 50 | 95 | 100 | 80 | 90 |
| Galium (2) | 30 | 80 | 55 | 60 | 50 | 80 | 85 | 70 | 65 |
| Green foxtail | 55 | 70 | 60 | 60 | 15 | 70 | 65 | 30 | 50 |
| I. Ryegrass | 10 | 10 | 30 | 20 | 5 | 70 | 20 | 20 | 20 |
| Jointed goatgra | 15 | 20 | 20 | 20 | 10 | 40 | 20 | 30 | 20 |

TABLE G-continued

| | | | | | | | | | |
|---|---|---|---|---|---|---|---|---|---|
| Kochia | 80 | 65 | 65 | 70 | 50 | 70 | 85 | 60 | 70 |
| Lambsquarters | 55 | 100 | 85 | 75 | 30 | 95 | 90 | 50 | 80 |
| LS canarygrass | 10 | 50 | 65 | 40 | 30 | 70 | 55 | 40 | 65 |
| Rape (1) | 70 | 100 | 100 | 100 | 95 | 90 | 100 | 50 | 85 |
| Redroot pigweed | 100 | 90 | 75 | 85 | 75 | 95 | 95 | 50 | 80 |
| Russian thistle | 55 | 80 | 70 | 75 | 50 | 60 | 75 | 40 | 75 |
| Scentless chamo | 10 | 70 | 60 | 100 | 70 | 95 | 100 | 30 | 50 |
| Spring Barley | 20 | 20 | 20 | 20 | 20 | 60 | 10 | 40 | 10 |
| Sugar beet | 100 | 100 | 100 | 100 | 60 | 95 | 100 | 70 | 100 |
| Sunflower | 10 | 30 | 30 | 45 | 30 | 60 | 35 | 50 | 20 |
| Veronica hedera | 55 | 98 | 90 | — | 80 | 100 | 100 | 70 | 70 |
| Wheat (spring) | 10 | 20 | 30 | 20 | 10 | 60 | 10 | 30 | 10 |
| Wheat (winter) | 10 | 10 | 10 | 20 | 10 | 50 | 10 | 30 | 10 |
| Wild buckwheat | 40 | 40 | 50 | 80 | 70 | 50 | 65 | 40 | 45 |
| Wild mustard | 100 | 98 | 100 | 80 | 75 | 100 | 100 | 100 | 85 |
| Wild oat (1) | 10 | 20 | 20 | 30 | 20 | 90 | 20 | 30 | 10 |
| Windgrass | 10 | 50 | 50 | 30 | 20 | 50 | 50 | 20 | 50 |

| | COMPOUND | | | | | | | | | | | | | | | |
|---|---|---|---|---|---|---|---|---|---|---|---|---|---|---|---|---|
| Rate 125 g/ha PREEMERGENCE | 6 | 12 | 13 | 14 | 16 | 20 | 21 | 22 | 24 | 25 | 29 | 36 | 37 | 49 | 51 | 56 | 57 |
| Alfalfa | — | 100 | — | — | — | — | — | — | — | — | — | — | — | — | — | — | — |
| Annual bluegras | 75 | 100 | 85 | 70 | 50 | 100 | 60 | 85 | 70 | 80 | 85 | 100 | 100 | 85 | 35 | 100 | 70 |
| Barley (winter) | 0 | 25 | 30 | 30 | 15 | 20 | 0 | 20 | 15 | 10 | 20 | 10 | 10 | 20 | 5 | 10 | 5 |
| Blackgrass (2) | 10 | 75 | 60 | 40 | 50 | 85 | 50 | 40 | 50 | 55 | 50 | 70 | 60 | 50 | 15 | 30 | 20 |
| Blk nightshade | 10 | 100 | 100 | 100 | 40 | 100 | 10 | 40 | 65 | 85 | 100 | 90 | 100 | 100 | 30 | 100 | 80 |
| Chickweed | 50 | 85 | 85 | 70 | 75 | 75 | 30 | 100 | 75 | 85 | 100 | 100 | 100 | 85 | 20 | 100 | 65 |
| Common poppy | — | — | 100 | 100 | 100 | 100 | 100 | 100 | 100 | 100 | 100 | 100 | 100 | 100 | 60 | 100 | 100 |
| Deadnettle | 85 | 85 | 70 | 70 | 70 | 85 | — | 75 | 70 | 70 | 75 | 70 | 90 | 100 | 40 | — | — |
| Downy brome | 10 | 100 | 50 | 60 | 40 | 80 | 10 | 30 | 55 | 65 | 10 | 100 | 100 | 50 | 0 | 10 | 20 |
| Field violet | 80 | 85 | 85 | 85 | 70 | 100 | 10 | 85 | 85 | 85 | 85 | 65 | 100 | 100 | 85 | 100 | 60 |
| Galium (2) | 30 | 100 | 100 | 100 | 100 | 100 | 30 | 70 | 100 | 100 | 100 | 100 | — | 70 | 100 | 100 | 100 |
| Green foxtail | 60 | 100 | 100 | 75 | 100 | 100 | 60 | 100 | 100 | 100 | 100 | 100 | 100 | 80 | 100 | 95 |
| I. Ryegrass | 20 | 100 | 50 | 50 | 50 | 75 | 45 | 15 | 20 | 30 | 30 | 100 | 70 | 30 | 10 | 20 | 10 |
| Jointed goatgra | 10 | 55 | 30 | 45 | 30 | 60 | 0 | 15 | 30 | 30 | 10 | 50 | 35 | 20 | 10 | 30 | 5 |
| Kochia | 85 | — | 85 | 75 | 65 | 75 | 5 | 60 | 90 | 70 | 70 | 100 | 100 | 70 | 60 | 70 | 100 |
| Lambsquarters | 10 | 70 | 85 | 70 | 75 | 75 | 50 | 85 | 70 | 70 | 70 | 75 | 70 | 70 | 70 | 70 | 70 |
| Lentil | — | 60 | — | — | — | — | — | — | — | — | — | — | — | — | — | — | — |
| LS canarygrass | 10 | 100 | 65 | 85 | 40 | 100 | 60 | 65 | 40 | 60 | 100 | 75 | 100 | 85 | 20 | 100 | 60 |
| Pea | — | 20 | — | — | — | — | — | — | — | — | — | — | — | — | — | — | — |
| Potato | — | 0 | — | — | — | — | — | — | — | — | — | — | — | — | — | — | — |
| Rape (1) | 10 | 85 | 90 | 85 | 70 | 85 | 10 | 60 | 65 | 85 | 85 | 85 | 85 | 100 | 20 | 100 | 90 |
| Redroot pigweed | 85 | 100 | 85 | 85 | 75 | 100 | 50 | 100 | 70 | 70 | 70 | 70 | 70 | 85 | 70 | 70 | 75 |
| Russian thistle | 0 | 100 | 50 | 50 | 40 | 80 | 0 | 20 | 60 | 65 | 60 | 100 | 100 | 100 | 10 | 100 | 50 |
| Scentless chamo | 55 | — | — | — | 100 | 100 | — | — | 70 | 70 | 70 | 70 | 70 | 85 | — | 75 | 70 |
| Sorghum | — | 30 | — | — | — | — | — | — | — | — | — | — | — | — | — | — | — |
| Spring Barley | 0 | 20 | 20 | 50 | 20 | 10 | 0 | 20 | 10 | 10 | 10 | 10 | 10 | 20 | 10 | 10 | 5 |
| Sugar beet | — | 100 | 100 | 85 | 100 | 100 | 40 | 100 | 100 | 100 | 100 | 100 | 100 | 100 | 60 | 85 | 75 |
| Sunflower | 0 | 30 | 20 | 20 | 20 | 25 | 0 | 20 | 30 | 60 | 50 | 50 | 60 | 15 | 10 | 10 | 10 |
| Veronica hedera | 60 | 100 | 100 | 100 | 100 | 100 | 60 | 100 | 100 | 100 | 100 | 100 | 100 | — | 100 | — | 5 |
| Wheat (spring) | 10 | 25 | 20 | 30 | 20 | 10 | 0 | 10 | 10 | 10 | 2 | 30 | 30 | 20 | 5 | 20 | 5 |
| Wheat (winter) | 0 | 20 | 20 | 40 | 10 | 10 | 0 | 20 | 10 | 0 | 2 | 20 | 10 | 10 | 10 | 10 | 2 |
| Wild buckwheat | 10 | 75 | 100 | 85 | 55 | 80 | 40 | 60 | 60 | 85 | 85 | 95 | 100 | 100 | 30 | 85 | 85 |
| Wild mustard | 50 | 100 | 100 | 100 | 100 | 100 | 80 | 85 | 100 | 100 | 100 | 100 | 100 | 100 | 100 | 85 | 85 |
| Wild oat (1) | 10 | 75 | 50 | 50 | 55 | 85 | 30 | 60 | 60 | 50 | 45 | 45 | 50 | 50 | 10 | 10 | 20 |
| Windgrass | 50 | 100 | 100 | 100 | 100 | 100 | 70 | 85 | 100 | 100 | 85 | 100 | 100 | 100 | 70 | 75 | 75 |

| | COMPOUND | | | | | | | | | | |
|---|---|---|---|---|---|---|---|---|---|---|---|
| Rate 62 g/ha POSTEMERGENCE | 12 | 13 | 14 | 20 | 21 | 22 | 49 | 50 | 51 | 52 | 56 | 57 |
| Annual bluegras | 30 | 20 | 30 | 20 | 20 | 50 | 30 | 50 | 20 | 50 | 60 | 60 |
| Barley (winter) | 10 | 10 | 10 | 30 | 30 | 60 | 10 | 40 | 50 | 50 | 10 | 10 |
| Blackgrass (2) | 10 | 10 | 10 | 20 | 10 | 40 | 20 | 30 | 20 | 40 | 20 | 20 |
| Blk nightshade | 100 | 85 | 100 | 100 | 75 | 90 | 100 | 60 | 90 | 80 | 100 | 90 |
| Chickweed | 55 | 60 | 60 | 70 | 30 | 75 | 70 | 30 | 40 | 60 | 60 | 50 |
| Common poppy | 100 | 60 | 100 | 85 | 40 | 100 | 100 | 70 | 30 | 80 | 100 | 50 |
| Deadnettle | 100 | 85 | 80 | 85 | 30 | 100 | 100 | 70 | 60 | 70 | 80 | 65 |
| Downy brome | 10 | 10 | 20 | 15 | 5 | 30 | 10 | 0 | 10 | 30 | 10 | 10 |
| Field violet | 100 | 100 | 100 | 100 | 30 | 90 | 100 | 90 | 30 | 70 | 100 | 80 |
| Galium (2) | 65 | 50 | 50 | 55 | 20 | 70 | 65 | 30 | 50 | 70 | 60 | 55 |
| Green foxtail | 65 | 50 | 40 | 60 | 10 | 50 | 50 | 20 | 20 | 60 | 65 | 50 |
| I. Ryegrass | 10 | 10 | 10 | 10 | 2 | 20 | 15 | 20 | 20 | 20 | 10 | 5 |
| Jointed goatgra | 10 | 10 | 10 | 10 | 5 | 40 | 10 | 20 | 20 | 30 | 10 | 10 |
| Kochia | 70 | 60 | 55 | 65 | 30 | 70 | 75 | 70 | 60 | 60 | 70 | 85 |
| Lambsquarters | 85 | 100 | 80 | 85 | 30 | 90 | 90 | 80 | 50 | 80 | 80 | 65 |

TABLE G-continued

| | | | | | | | | | | | | |
|---|---|---|---|---|---|---|---|---|---|---|---|---|
| LS canarygrass | 20 | 20 | 30 | 30 | 20 | 60 | 30 | 40 | 30 | 40 | 60 | 25 |
| Rape (1) | 100 | 85 | 80 | 100 | 100 | 80 | 95 | 60 | 50 | 50 | 100 | 80 |
| Redroot pigweed | 85 | 65 | 60 | 80 | 70 | 95 | 90 | 90 | 50 | 95 | 70 | 80 |
| Russian thistle | 70 | 70 | 60 | 75 | 30 | 50 | 75 | 30 | 40 | 40 | 70 | 65 |
| Scentless chamo | 55 | — | 30 | 65 | 50 | 80 | 60 | 80 | 30 | 30 | 30 | 30 |
| Spring Barley | 10 | 10 | 10 | 10 | 10 | 50 | 10 | 40 | 30 | 40 | 10 | 10 |
| Sugar beet | 100 | 90 | 100 | 100 | 50 | 90 | 100 | 80 | 50 | 80 | 100 | 80 |
| Sunflower | 20 | 20 | 20 | 50 | 30 | 60 | 30 | 70 | 40 | 50 | 10 | 40 |
| Veronica hedera | 100 | 98 | 100 | — | 75 | 100 | 100 | 100 | 80 | 95 | 75 | 60 |
| Wheat (spring) | 10 | 10 | 20 | 10 | 10 | 50 | 10 | 30 | 30 | 30 | 10 | 15 |
| Wheat (winter) | 10 | 10 | 10 | 10 | 10 | 40 | 10 | 30 | 20 | 30 | 10 | 10 |
| Wild buckwheat | 40 | 40 | 30 | 80 | 45 | 50 | 40 | 30 | 40 | 50 | 60 | 50 |
| Wild mustard | 100 | 80 | 100 | 70 | 75 | 100 | 100 | 60 | 100 | 90 | 100 | 95 |
| Wild oat (1) | 20 | 10 | 10 | 20 | 20 | 70 | 15 | 20 | 30 | 50 | 10 | 10 |
| Windgrass | 20 | 20 | 20 | 30 | 10 | 30 | 30 | 20 | 20 | 30 | 30 | 30 |

| | COMPOUND | | | | | | | | | | | | | | | |
|---|---|---|---|---|---|---|---|---|---|---|---|---|---|---|---|---|
| Rate 62 g/ha PREEMERGENCE | 12 | 13 | 14 | 20 | 21 | 22 | 24 | 25 | 29 | 36 | 37 | 49 | 50 | 51 | 52 | 56 | 57 |
| Alfalfa | 100 | — | — | — | — | — | — | — | — | — | — | — | — | — | — | — | — |
| Annual bluegras | 100 | 75 | 70 | 85 | 20 | 100 | 60 | 60 | 55 | 70 | 70 | 80 | 50 | 85 | 20 | 75 | 70 |
| Barley (winter) | 10 | 35 | 20 | 10 | 0 | 10 | 5 | 10 | 30 | 10 | 10 | 10 | 30 | 0 | 10 | 5 | 10 |
| Blackgrass (2) | 50 | 15 | 55 | 20 | 40 | 20 | 50 | 30 | 30 | 55 | 60 | 20 | 30 | 10 | 20 | 10 | 10 |
| Blk nightshade | 65 | 85 | 65 | 60 | 0 | 30 | 60 | 50 | 85 | 60 | 100 | 100 | 0 | 20 | 10 | 100 | 60 |
| Chickweed | 80 | 85 | 85 | 85 | 15 | 50 | 75 | 85 | 75 | 100 | 85 | 80 | 30 | 20 | 70 | 80 | 60 |
| Common poppy | — | 100 | 100 | 100 | 70 | 70 | 100 | 100 | 100 | 100 | 100 | 100 | 90 | — | 60 | 100 | 100 |
| Deadnettle | 75 | 70 | 85 | 100 | — | 85 | 60 | 55 | 70 | 85 | 85 | 100 | 100 | 30 | 10 | — | — |
| Downy brome | 65 | 30 | 50 | 55 | 20 | 20 | 30 | 50 | 40 | 85 | 50 | 25 | 50 | 5 | 5 | 20 | 5 |
| Field violet | 100 | 100 | 85 | 100 | 0 | 100 | 70 | 65 | 70 | 65 | 60 | 85 | 50 | 65 | 60 | 100 | 60 |
| Galium (2) | 100 | 100 | 100 | 100 | 0 | 60 | 100 | 100 | 100 | 100 | 100 | — | 40 | — | 40 | 100 | 100 |
| Green foxtail | 100 | 100 | 60 | 100 | 50 | 100 | 85 | 100 | 100 | 100 | 100 | 100 | 80 | 35 | 100 | 100 | 10 |
| I. Ryegrass | 10 | 30 | 30 | 50 | 10 | 10 | 20 | 30 | 20 | 85 | 65 | 55 | 0 | 10 | 10 | 10 | 5 |
| Jointed goatgra | 20 | 20 | 10 | — | 5 | — | 30 | 30 | 10 | 30 | 35 | 10 | 20 | 0 | 10 | 5 | 0 |
| Kochia | — | 70 | 40 | 70 | 5 | 50 | 55 | 100 | 65 | 100 | 100 | 60 | 30 | 30 | 60 | 60 | 50 |
| Lambsquarters | 70 | 65 | 65 | 70 | 30 | 65 | 70 | 70 | 70 | 70 | 70 | 70 | 80 | 60 | 85 | 100 | 70 |
| Lentil | 30 | — | — | — | — | — | — | — | — | — | — | — | — | — | — | — | — |
| LS canarygrass | 100 | 20 | 60 | 75 | 20 | 45 | 30 | 50 | 20 | 65 | 60 | 85 | 40 | 40 | 30 | 30 | 50 |
| Pea | 10 | — | — | — | — | — | — | — | — | — | — | — | — | — | — | — | — |
| Potato | 0 | — | — | — | — | — | — | — | — | — | — | — | — | — | — | — | — |
| Rape (1) | 80 | 100 | 65 | 80 | 10 | 55 | 65 | 75 | 80 | 85 | 85 | 85 | 30 | 10 | 40 | 100 | 100 |
| Redroot pigweed | 100 | 100 | 85 | 70 | 0 | 85 | 70 | 70 | 70 | 70 | — | 100 | 90 | — | 100 | 100 | 70 |
| Russian thistle | 100 | 20 | 20 | 60 | 0 | 10 | 30 | 30 | 70 | 100 | 50 | 35 | 20 | 5 | 0 | 50 | 30 |
| Scentless chamo | 70 | — | — | 80 | — | — | 70 | 70 | 70 | 70 | 70 | 60 | 90 | — | — | 70 | 70 |
| Sorghum | 10 | — | — | — | — | — | — | — | — | — | — | — | — | — | — | — | — |
| Spring Barley | 20 | 10 | 10 | 10 | 0 | 10 | 5 | 10 | 10 | 5 | 10 | 20 | 0 | 5 | 5 | 10 | 2 |
| Sugar beet | 100 | 100 | 85 | 100 | 50 | 50 | 100 | 100 | 85 | 100 | 100 | 100 | 30 | 55 | 60 | 30 | 85 |
| Sunflower | 50 | 20 | 10 | 15 | 10 | 10 | 20 | 55 | 50 | 35 | 60 | 20 | 30 | 5 | 10 | 5 | 0 |
| Veronica hedera | 100 | 100 | 100 | 100 | 50 | 70 | 100 | 100 | 100 | 100 | 100 | — | — | 100 | 100 | — | — |
| Wheat (spring) | 10 | 10 | 10 | 5 | 10 | 10 | 5 | 2 | 2 | 10 | 20 | 20 | 30 | 0 | 0 | 10 | 5 |
| Wheat (winter) | 10 | 20 | 30 | 10 | 5 | 10 | 5 | 0 | 5 | 20 | 20 | 10 | 10 | 0 | 5 | 5 | 0 |
| Wild buckwheat | 30 | 85 | 60 | 70 | 5 | 25 | 60 | 80 | 65 | 80 | 75 | 80 | 30 | 50 | 50 | 30 | 50 |
| Wild mustard | 100 | 100 | 70 | 100 | 55 | 80 | 85 | 100 | 85 | 100 | 100 | 100 | 80 | 60 | 70 | 85 | 70 |
| Wild oat (1) | 30 | 40 | 20 | 30 | 10 | 30 | 30 | 20 | 30 | 30 | 50 | 80 | 50 | 0 | 20 | 10 | 10 |
| Windgrass | 100 | 85 | 100 | 85 | 15 | 50 | 100 | 100 | 100 | 100 | 100 | 100 | 70 | 60 | 70 | 70 | 55 |

| | COMPOUND | | | | | | | | | | |
|---|---|---|---|---|---|---|---|---|---|---|---|
| Rate 31 g/ha POSTEMERGENCE | 13 | 14 | 20 | 21 | 22 | 49 | 50 | 51 | 52 | 56 | 57 |
| Annual bluegras | 10 | 20 | 15 | 20 | 30 | 20 | 50 | 10 | 30 | 50 | 50 |
| Barley (winter) | 10 | 10 | 20 | 10 | 60 | 10 | 40 | 50 | 50 | 10 | 10 |
| Blackgrass (2) | 10 | 10 | 10 | 10 | 20 | 10 | 30 | 10 | 30 | 10 | 10 |
| Blk nightshade | 100 | 75 | 100 | 70 | 90 | 100 | 60 | 70 | 90 | 75 | 80 |
| Chickweed | 50 | 50 | 55 | 45 | 70 | 60 | 10 | 40 | 60 | 60 | 50 |
| Common poppy | 50 | 85 | 85 | 30 | 100 | 100 | 50 | 20 | 60 | 85 | 50 |
| Deadnettle | 85 | 60 | 80 | 30 | 70 | 85 | 60 | 60 | 40 | 75 | 60 |
| Downy brome | 10 | 20 | 10 | 2 | 30 | 10 | 0 | 10 | 20 | 10 | 5 |
| Field violet | 100 | 100 | 100 | 10 | 80 | 100 | 60 | 30 | 50 | 70 | 70 |
| Galium (2) | 40 | 40 | 50 | 20 | 50 | 70 | 40 | 30 | 50 | 60 | 50 |
| Green foxtail | 30 | 10 | 30 | 10 | 30 | 10 | 0 | 20 | 30 | 30 | 60 |
| I. Ryegrass | 10 | 10 | 10 | 0 | 20 | 10 | 0 | 20 | 20 | 10 | 5 |
| Jointed goatgra | 10 | 10 | 10 | 2 | 30 | 10 | 20 | 20 | 30 | 10 | 10 |
| Kochia | 50 | 50 | 60 | 20 | 60 | 75 | 50 | 60 | 60 | 60 | 60 |
| Lambsquarters | 100 | 85 | 80 | 0 | 70 | 100 | 50 | 30 | 70 | 75 | 65 |
| LS canarygrass | 10 | 20 | 20 | 10 | 40 | 10 | 40 | 20 | 30 | 55 | 20 |
| Rape (1) | 85 | 55 | 100 | 60 | 60 | 75 | 60 | 20 | 50 | 70 | 65 |

TABLE G-continued

| | | | | | | | | | | | |
|---|---|---|---|---|---|---|---|---|---|---|---|
| Redroot pigweed | 55 | 50 | 70 | 60 | 90 | 85 | 50 | 20 | 80 | 70 | 70 |
| Russian thistle | 60 | 50 | 70 | 20 | 40 | 60 | 20 | 20 | 30 | 60 | 70 |
| Scentless chamo | 30 | 20 | 70 | 0 | 70 | 50 | 80 | 20 | 20 | 10 | 10 |
| Spring Barley | 10 | 10 | 15 | 5 | 40 | 10 | 50 | 30 | 40 | 10 | 10 |
| Sugar beet | 65 | 55 | 100 | 30 | 60 | 75 | 100 | 40 | 70 | 98 | 98 |
| Sunflower | 15 | 20 | 30 | 30 | 30 | 20 | 50 | 20 | 30 | 20 | 30 |
| Veronica hedera | 100 | 98 | — | 70 | 100 | 100 | 50 | 70 | 90 | 70 | 55 |
| Wheat (spring) | 10 | 10 | 10 | 5 | 40 | 10 | 20 | 10 | 20 | 10 | 10 |
| Wheat (winter) | 10 | 10 | 10 | 5 | 30 | 10 | 30 | 10 | 30 | 10 | 5 |
| Wild buckwheat | 30 | 20 | 30 | 30 | 50 | 40 | 45 | 20 | 50 | 40 | 55 |
| Wild mustard | 60 | 70 | 100 | 60 | 100 | 95 | 40 | 70 | 90 | 90 | 95 |
| Wild oat (1) | 10 | 10 | 10 | 30 | 60 | 10 | 0 | 20 | 40 | 20 | 10 |
| Windgrass | 10 | 10 | 20 | 10 | 30 | 20 | 20 | 10 | 20 | 20 | 20 |

| | COMPOUND | | | | | | | | | | | | | |
|---|---|---|---|---|---|---|---|---|---|---|---|---|---|---|
| Rate 31 g/ha PREEMERGENCE | 12 | 13 | 14 | 16 | 20 | 21 | 22 | 24 | 36 | 37 | 49 | 50 | 51 | 52 | 56 |
| Alfalfa | 60 | — | — | — | — | — | — | — | — | — | — | — | — | — |
| Annual bluegras | 100 | 55 | 60 | 30 | 60 | 10 | 50 | 50 | 50 | 60 | 75 | 40 | 10 | 10 | 40 |
| Barley (winter) | 10 | 10 | 10 | 5 | 5 | 10 | 5 | 5 | 10 | 0 | 20 | 0 | 0 | 5 | 2 |
| Blackgrass (2) | 30 | 10 | 10 | 20 | 10 | 30 | 10 | 30 | 20 | 50 | 10 | 30 | 5 | 10 | 10 |
| Blk nightshade | 35 | 60 | 50 | 20 | 50 | 0 | 20 | 50 | 60 | 50 | 60 | 0 | 10 | 5 | 60 |
| Chickweed | 75 | 85 | 70 | 70 | 60 | 10 | 20 | 70 | 85 | 70 | 85 | 0 | 30 | 30 | 85 |
| Common poppy | — | 85 | 100 | 100 | 100 | 65 | 60 | 100 | 100 | 100 | 100 | 90 | 25 | 20 | 100 |
| Deadnettle | 30 | 70 | 60 | 60 | 85 | — | 30 | 70 | 55 | 65 | 85 | 50 | 20 | 5 | — |
| Downy brome | 20 | 40 | 30 | 15 | 10 | 10 | 10 | 20 | 50 | 50 | 10 | 50 | 0 | 0 | 0 |
| Field violet | 50 | 70 | 70 | 70 | 70 | 50 | 50 | 60 | 10 | 50 | 60 | 30 | 70 | 65 | 30 |
| Galium (2) | 100 | 100 | 70 | 70 | 100 | 0 | 50 | 60 | 100 | 60 | — | 0 | 10 | 20 | 100 |
| Green foxtail | 100 | 55 | 50 | 100 | 100 | 30 | 50 | 100 | 100 | 100 | 100 | 40 | 10 | 55 | 60 |
| I. Ryegrass | 20 | 20 | 45 | 10 | 20 | 20 | 10 | 20 | 10 | 30 | 10 | 0 | 0 | 5 | 20 |
| Jointed goatgra | 10 | 10 | 20 | 10 | 10 | 0 | 0 | 10 | 20 | 20 | 5 | 20 | 0 | 5 | 10 |
| Kochia | — | 65 | 30 | 60 | 60 | 0 | 30 | 50 | 100 | 100 | 55 | 20 | 10 | 50 | 50 |
| Lambsquarters | 65 | 70 | 65 | 70 | 55 | 60 | 30 | 70 | 60 | 65 | 70 | 30 | 50 | 100 | 100 |
| Lentil | 20 | — | — | — | — | — | — | — | — | — | — | — | — | — | — |
| LS canarygrass | 100 | 20 | 30 | 20 | 20 | 10 | 15 | 20 | — | 60 | 75 | 50 | 5 | 20 | 20 |
| Pea | 10 | — | — | — | — | — | — | — | — | — | — | — | — | — | — |
| Potato | 10 | — | — | — | — | — | — | — | — | — | — | — | — | — | — |
| Rape (1) | 65 | 50 | 10 | 60 | 50 | 0 | 30 | 60 | 60 | 100 | 65 | 0 | 10 | 20 | 100 |
| Redroot pigweed | 80 | 70 | 85 | 70 | 75 | 30 | 60 | 70 | — | 65 | 100 | 90 | 50 | 65 | 100 |
| Russian thistle | 100 | 30 | 10 | 20 | 30 | 5 | 0 | 20 | 20 | 30 | 20 | 0 | 0 | 0 | 10 |
| Scentless chamo | — | — | — | 70 | 70 | — | — | 100 | 60 | 70 | 70 | 50 | — | — | 10 |
| Sorghum | 5 | — | — | — | — | — | — | — | — | — | — | — | — | — | — |
| Spring Barley | 10 | 10 | 10 | 2 | 5 | 0 | 10 | 2 | 10 | 10 | 10 | 0 | 2 | 5 | 5 |
| Sugar beet | 100 | 85 | 70 | 60 | 65 | 30 | 35 | 90 | 100 | 100 | 100 | 30 | 10 | 50 | 45 |
| Sunflower | 20 | 0 | 10 | 40 | 10 | 10 | 0 | 0 | 25 | 55 | 10 | 30 | 0 | 5 | 5 |
| Veronica hedera | 100 | 100 | 100 | 70 | 100 | 50 | 100 | 100 | 100 | 100 | — | — | 65 | 100 | — |
| Wheat (spring) | 5 | 5 | 20 | 10 | 0 | 0 | 5 | 2 | 10 | 10 | 10 | 10 | 0 | 0 | 10 |
| Wheat (winter) | 5 | 5 | 20 | 0 | 5 | 0 | 5 | 2 | 10 | 0 | 0 | 0 | 10 | 0 | 0 |
| Wild buckwheat | 20 | 65 | 55 | 30 | 60 | 0 | 10 | 35 | 60 | 65 | 50 | 30 | 20 | 10 | 40 |
| Wild mustard | 100 | 85 | 65 | 100 | 85 | 40 | 60 | 70 | 100 | 100 | 100 | 60 | 50 | 55 | 100 |
| Wild oat (1) | 20 | 20 | 30 | 20 | 10 | 20 | 10 | 20 | 20 | 20 | 30 | 50 | 0 | 10 | 10 |
| Windgrass | 100 | 50 | 100 | 100 | 55 | 50 | 45 | 80 | 100 | 100 | 100 | 50 | 30 | 60 | 50 |

| | COMPOUND | | COMPOUND | | | |
|---|---|---|---|---|---|---|
| Rate 16 g/ha POSTEMERGENCE | 52 | Rate 16 g/ha PREEMERGENCE | 12 | 52 | 56 | 57 |
| Annual bluegras | 20 | Alfalfa | 50 | — | — | — |
| Barley (winter) | 40 | Annual bluegras | 30 | 5 | 20 | 10 |
| Blackgrass (2) | 20 | Barley (winter) | 5 | 0 | 5 | 10 |
| Blk nightshade | 90 | Blackgrass (2) | 50 | 5 | 5 | 0 |
| Chickweed | 60 | Blk nightshade | 30 | 2 | 30 | 35 |
| Common poppy | 40 | Chickweed | 10 | 0 | 75 | 50 |
| Deadnettle | 20 | Common poppy | — | 65 | 60 | 100 |
| Downy brome | 10 | Deadnettle | 20 | 0 | 65 | 30 |
| Field violet | 30 | Downy brome | 10 | 10 | 5 | 5 |
| Galium (2) | 20 | Field violet | 20 | 10 | 5 | 0 |
| Green foxtail | 30 | Galium (2) | 60 | 10 | 40 | 30 |
| I. Ryegrass | 0 | Green foxtail | 60 | 50 | 60 | 30 |
| Jointed goatgra | 20 | I. Ryegrass | 10 | 0 | 5 | 5 |
| Kochia | 50 | Jointed goatgra | 5 | 0 | 10 | 0 |
| Lambsquarters | 30 | Kochia | — | 30 | 50 | 10 |
| LS canarygrass | 30 | Lambsquarters | 15 | 30 | 70 | 65 |
| Rape (1) | 30 | Lentil | 10 | — | — | — |
| Redroot pigweed | 30 | LS canarygrass | 10 | 5 | 20 | 5 |
| Russian thistle | 10 | Pea | 5 | — | — | — |

TABLE G-continued

| | | | | | | |
|---|---|---|---|---|---|---|
| Scentless chamo | 0 | Potato | 0 | — | — | — |
| Spring Barley | 30 | Rape (1) | 55 | 10 | 85 | 65 |
| Sugar beet | 50 | Redroot pigweed | 70 | 55 | 70 | 40 |
| Sunflower | 20 | Russian thistle | 85 | 0 | 50 | 10 |
| Veronica hedera | 80 | Scentless chamo | — | — | 0 | 20 |
| Wheat (spring) | 10 | Sorghum | 5 | — | — | — |
| Wheat (winter) | 30 | Spring Barley | 5 | 0 | 10 | 0 |
| Wild buckwheat | 60 | Sugar beet | 100 | 10 | 40 | 65 |
| Wild mustard | 70 | Sunflower | 10 | 0 | 10 | 10 |
| Wild oat (1) | 30 | Veronica hedera | 100 | 100 | 100 | 100 |
| Windgrass | 10 | Wheat (spring) | 5 | 0 | 0 | 0 |
| | | Wheat (winter) | 0 | 0 | 0 | 0 |
| | | Wild buckwheat | 10 | 0 | 30 | 20 |
| | | Wild mustard | 100 | 45 | 100 | 50 |
| | | Wild oat (1) | 10 | 15 | 5 | 0 |
| | | Windgrass | 101 | 45 | 10 | 10 |

| | COMPOUND | | COMPOUND | | COMPOUND | |
|---|---|---|---|---|---|---|
| Rate 8 g/ha | 12 | Rate 4 g/ha | 12 | Rate 2 g/ha | 12 |
| PREEMERGENCE | | PREEMERGENCE | | PREEMERGENCE | |
| Alfalfa | 50 | Alfalfa | 20 | Alfalfa | 30 |
| Annual bluegras | — | Annual bluegras | — | Annual bluegras | — |
| Barley (winter) | 5 | Barley (winter) | 0 | Barley (winter) | 0 |
| Blackgrass (2) | — | Blackgrass (2) | — | Blackgrass (2) | — |
| Blk nightshade | — | Blk nightshade | — | Blk nightshade | — |
| Chickweed | — | Chickweed | — | Chickweed | — |
| Common poppy | — | Common poppy | — | Common poppy | — |
| Deadnettle | — | Deadnettle | — | Deadnettle | — |
| Downy brome | — | Downy brome | — | Downy brome | — |
| Field violet | — | Field violet | — | Field violet | — |
| Galium (2) | — | Galium (2) | — | Galium (2) | — |
| Green foxtail | — | Green foxtail | — | Green foxtail | — |
| I. Ryegrass | — | I. Ryegrass | — | I. Ryegrass | — |
| Jointed goatgra | — | Jointed goatgra | — | Jointed goatgra | — |
| Kochia | — | Kochia | — | Kochia | — |
| Lambsquarters | — | Lambsquarters | — | Lambsquarters | — |
| Lentil | 5 | Lentil | 0 | Lentil | 0 |
| LS canarygrass | — | LS canarygrass | — | LS canarygrass | — |
| Pea | 5 | Pea | 10 | Pea | 0 |
| Potato | 0 | Potato | 0 | Potato | 0 |
| Rape (1) | 10 | Rape (1) | 20 | Rape (1) | 10 |
| Redroot pigweed | — | Redroot pigweed | — | Redroot pigweed | — |
| Russian thistle | — | Russian thistle | — | Russian thistle | — |
| Scentless chamo | — | Scentiess chamo | — | Scentless chamo | — |
| Sorghum | 2 | Sorghum | 0 | Sorghum | 0 |
| Sprlng Barley | 5 | Spring Barley | 0 | Spring Barley | 0 |
| Sugar beet | 10 | Sugar beet | 15 | Sugar beet | 0 |
| Sunflower | 0 | Sunflower | 0 | Sunflower | 0 |
| Veronica hedera | — | Veronica hedera | — | Veronica hedera | — |
| Wheat (sprlng) | 0 | Wheat (spring) | 0 | Wheat (spring) | 0 |
| Wheat (winter) | 0 | Wheat (winter) | 0 | Wheat (winter) | 0 |
| Wild buckwheat | — | Wild buckwheat | — | Wild buckwheat | — |
| Wild mustard | — | Wild mustard | — | Wild mustard | — |
| Wild oat (1) | — | Wild oat (1) | — | Wild oat (1) | — |
| Windgrass | — | Windgrass | — | Windgrass | — |

| | COMPOUND | | Lentil | 0 |
|---|---|---|---|---|
| Rate 1 g/ha | 12 | | LS canarygrass | — |
| PREEMERGENCE | | | Pea | 0 |
| Alfalfa | 5 | | Potato | 0 |
| Annual bluegras | — | | Rape (1) | 0 |
| Barley (winter) | 0 | | Redroot pigweed | — |
| Blackgrass (2) | — | | Russian thistle | — |
| Blk nightshade | — | | Scentless chamo | — |
| Chickweed | — | | Sorghum | 0 |
| Common poppy | — | | Spring Barley | 0 |
| Deadnettle | — | | Sugar beet | 0 |
| Downy brome | — | | Sunflower | 0 |
| Field violet | — | | Veronica hedera | — |
| Galium (2) | — | | Wheat (spring) | 0 |
| Green foxtail | — | | Wheat (winter) | 0 |
| I. Ryegrass | — | | Wild buckwheat | — |
| Jointed goatgra | — | | Wild mustard | — |
| Kochia | — | | Wild oat (1) | — |
| Lambsquarters | — | | Windgrass | — |

What is claimed is:

1. A compound selected from Formula I, geometric or stereoisomers thereof, N-oxides thereof, and agriculturally suitable salts thereof,

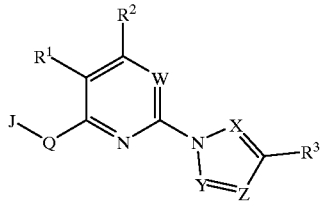

wherein J is

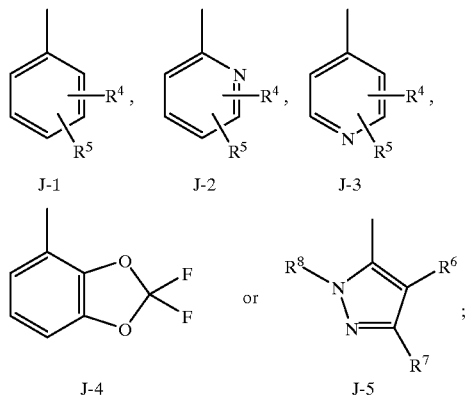

W is N or CR$^9$;

X, Y and Z are independently N, CH or CR$^9$, provided that only one of X, Y and Z is CR$^9$;

Q is O or S(O)$_n$;

R$^1$ and R$^2$ are independently H, halogen, cyano, C$_1$–C$_4$ alkoxy, C$_1$–C$_4$ haloalkoxy, C$_2$–C$_4$ alkoxyalkyl, C$_3$–C$_5$ dialkoxyalkyl, C$_1$–C$_4$ alkyl, C$_1$–C$_4$ haloalkyl, C$_2$–C$_4$ alkoxyalkyl, C$_3$–C$_4$ alkenyl, C$_3$–C$_4$ alkynyl, C$_3$–C$_4$ alkenyloxy, C$_3$–C$_4$ alkynyloxy, S(O)$_n$R$^8$, C$_2$–C$_4$ alkylthioalkyl, C$_2$–C$_4$ alkylsulfonylalkyl, C$_1$–C$_4$ alkylamino or C$_2$–C$_4$ dialkylamino;

R$^3$ is C$_1$–C$_4$ haloalkyl;

R$^4$ is halogen, cyano, SF$_5$, C$_1$–C$_4$ haloalkyl, C$_1$–C$_4$ alkoxy, C$_1$–C$_4$ haloalkoxy or S(O)$_n$R$^8$;

R$^5$ is H, halogen, cyano, SF$_5$, C$_1$–C$_4$ haloalkyl, C$_1$–C$_4$ alkoxy, C$_1$–C$_4$ haloalkoxy or S(O)$_n$R$^8$;

R$^6$ is H, halogen, cyano, SF$_5$, C$_1$–C$_4$ haloalkyl, C$_1$–C$_4$ alkoxy, C$_1$–C$_4$ haloalkoxy or S(O)$_n$R$^8$;

R$^7$ is halogen, cyano, SF$_5$, C$_1$–C$_4$ haloalkyl, C$_1$–C$_4$ alkoxy, C$_1$–C$_4$ haloalkoxy or S(O)$_n$R$^8$;

each R$^8$ is independently C$_1$–C$_4$ alkyl or C$_1$–C$_4$ haloalkyl;

each R$^9$ is independently halogen, cyano, C$_1$–C$_4$ alkoxy, C$_1$–C$_4$ haloalkoxy, C$_1$–C$_4$ alkyl, C$_1$–C$_4$ haloalkyl, C$_2$–C$_4$ alkoxyalkyl, C$_3$–C$_4$ alkenyl, C$_3$–C$_4$ alkynyl, C$_3$–C$_4$ alkenyloxy, C$_3$–C$_4$ alkynyloxy or S(O)$_n$R$^8$;

R$^{10}$ is H, C$_1$–C$_4$ alkyl or C$_1$–C$_4$ haloalkyl; and each n is independently 0, 1 or 2.

2. A compound of claim 1 wherein:

Q is O;

R$^1$ and R$^2$ are independently H, C$_1$–C$_4$ alkyl or C$_1$–C$_4$ alkoxy.

3. A compound of claim 2 wherein:

W is N;

Y is CR$^9$; and

R$^5$ is H.

4. A compound of claim 3 wherein:

R$^2$ is H; and each R$^4$ is independently halogen, C$_1$–C$_4$ haloalkyl, C$_1$–C$_4$ haloalkoxy or C$_1$–C$_4$ haloalkylthio.

5. The compound of claim 4 which is selected from the group:

(a) 5-methyl4-[3-(trifluoromethyl)phenoxy]-2-[3-(trifluoromethyl)-1H-pyrazol-1-yl]pyrimidine;

(b) 4-[3-(trifluoromethyl)phenoxy]-2-[3-(trifluoromethyl)-1H-pyrazol-1-yl]pyrimidine;

(c) 5-methyl-4-[3-(trifluoromethoxy)phenoxy]-2-[4-(trifluoromethyl)-1H-imidazol-1-yl]pyrimidine;

(d) 5-methyl-2-[3-(trifluoromethyl)-1H-pyrazol-1-yl]-4-[[6-(trifluoromethyl)-2-pyridinyl]oxy]pyrimidine;

(e) 5-methyl-4-[3-(trifluoromethyl)phenoxy]-2-[3-(trifluoromethyl)-1H-1,2,4-triazol-1-yl]pyrimidine;

(f) 5-methyl-2-[4-(trifluoromethyl)-1H-imidazol-1-yl]-4-[3-(trifluoromethyl)phenoxy]pyrimidine;

(g) 5-ethyl-4-[3-(trifluoromethyl)phenoxy]-2-[3-(trifluoromethyl)-1H-pyrazol-1-yl]pyrimidine;

(h) 5-ethyl-4-[3-(trifluoromethoxy)phenoxy]-2-[3-(trifluoromethyl)-1H-pyrazol-1-yl]pyrimidine;

(i) 5-ethyl-2-[4-(trifluoromethyl)-1H-imidazol-1-yl]-4-[3-(trifluoromethyl)phenoxy]pyrimidine; and (j) 5-ethyl-4-[3-(trifluoromethoxy)phenoxy]-2-[4-(trifluoromethyl)-1H-imidazol-1-yl]pyrimidine.

6. A compound selected from Formula 1a and agriculturally suitable salts thereof,

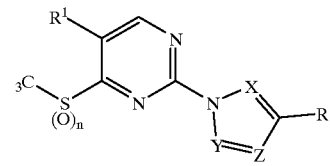

wherein

X, Y and Z are independently N, CH or CR$^9$, provided that only one of X, Y and Z is CR$^9$;

R$^1$ is H, C$_1$–C$_4$ alkyl or C$_1$–C$_4$ alkoxy;

R$^3$ is C$_1$–C$_4$ haloalkyl;

each R$^9$ is independently halogen or cyano; and n is 0, 1 or 2.

7. A compound of claim 6 wherein

R$^1$ is C$_1$–C$_4$ alkyl.

8. A herbicidal composition comprising a herbicidally effective amount of a compound of claim 1 and at least one of a surfactant, a solid diluent or a liquid diluent.

9. A method for controlling the growth of undesired vegetation comprising contacting the vegetation or its environment with a herbicidally effective amount of a compound of claim 1.

* * * * *